US011726051B2

(12) United States Patent
Smith et al.

(10) Patent No.: US 11,726,051 B2
(45) Date of Patent: Aug. 15, 2023

(54) APPARATUS FOR MONITORING A FLUID

(71) Applicant: 4T2 SENSORS LTD, Sutton Coldfield (GB)

(72) Inventors: Alexander Edward Smith, Sutton Coldfield (GB); Maxim Harry Joseph Swinbourne, Sutton Coldfield (GB)

(73) Assignee: 4T2 SENSORS LTD, Sutton Coldfield (GB)

( * ) Notice: Subject to any disclaimer, the term of this patent is extended or adjusted under 35 U.S.C. 154(b) by 167 days.

(21) Appl. No.: 17/287,929

(22) PCT Filed: Oct. 18, 2019

(86) PCT No.: PCT/GB2019/052979
§ 371 (c)(1),
(2) Date: Apr. 22, 2021

(87) PCT Pub. No.: WO2020/084281
PCT Pub. Date: Apr. 30, 2020

(65) Prior Publication Data
US 2021/0396698 A1 Dec. 23, 2021

(30) Foreign Application Priority Data

Oct. 24, 2018 (GB) .................................... 1817278
Dec. 3, 2018 (GB) .................................... 1819732

(51) Int. Cl.
*G01R 27/26* (2006.01)
*G01N 27/04* (2006.01)
(Continued)

(52) U.S. Cl.
CPC .......... *G01N 27/046* (2013.01); *G01N 27/06* (2013.01); *G01N 27/228* (2013.01); *G01N 33/14* (2013.01)

(58) Field of Classification Search
USPC ................ 324/639, 640, 664, 689, 694, 663
See application file for complete search history.

(56) References Cited

U.S. PATENT DOCUMENTS 3,691,841 A    9/1972  Lorenzino et al.
4,496,454 A    1/1985  Berger
(Continued)

FOREIGN PATENT DOCUMENTS

CN    205080193 U    3/2016
CN    106154048 A    11/2016
(Continued)

OTHER PUBLICATIONS

"International Search Report and Written Opinion of the International Searching Authority", International Application No. PCT/GB2019/052979, dated Jun. 2, 2020, 18 pp.
(Continued)

*Primary Examiner* — Vincent Q Nguyen
(74) *Attorney, Agent, or Firm* — Myers Bigel, P.A.

(57) ABSTRACT

A processing apparatus is configured to receive a sense signal from a capacitive fluid sensor having a first electrode and a second electrode with a sensing region between the electrodes. The processing apparatus is configured to receive an alternating drive signal applied to the capacitive fluid sensor. The processing apparatus is configured to determine a complex impedance of the fluid sensor based on the sense signal and the drive signal. The complex impedance includes an in-phase component indicative of a conductivity quantity of a fluid in the sensing region and a quadrature component indicative of a capacitance quantity of the fluid sensor. The processing apparatus is configured to determine a temperature of the fluid in dependence on at least the determined capacitance quantity of the fluid sensor.

18 Claims, 33 Drawing Sheets

(51) Int. Cl.
  *G01N 27/06* (2006.01)
  *G01N 27/22* (2006.01)
  *G01N 33/14* (2006.01)

(56) References Cited

U.S. PATENT DOCUMENTS

| | | | |
|---|---|---|---|
| 5,565,768 A | 10/1996 | Kadar | |
| 5,609,576 A | 3/1997 | Voss et al. | |
| 5,677,631 A | 10/1997 | Reittinger et al. | |
| 6,691,040 B2* | 2/2004 | Bosetto | A61M 1/1613 702/19 |
| 7,043,402 B2 | 5/2006 | Phillips et al. | |
| 2002/0125899 A1 | 9/2002 | Lvovich et al. | |
| 2004/0012399 A1 | 1/2004 | Lin et al. | |
| 2005/0264302 A1* | 12/2005 | Mohajer | G01N 22/00 324/639 |
| 2008/0116908 A1 | 5/2008 | Potyrailo et al. | |
| 2008/0197863 A1 | 8/2008 | Lin et al. | |
| 2009/0048786 A1* | 2/2009 | Nardo | G01N 33/146 702/25 |
| 2009/0107666 A1 | 4/2009 | Tchakarov et al. | |
| 2010/0188111 A1 | 7/2010 | Fougere | |
| 2010/0295565 A1 | 11/2010 | Drack | |
| 2010/0321036 A1 | 12/2010 | Camp | |
| 2012/0064567 A1 | 3/2012 | Stakenborg et al. | |
| 2012/0114089 A1 | 5/2012 | Potyrailo et al. | |
| 2012/0197566 A1 | 8/2012 | Habic et al. | |
| 2013/0346002 A1 | 12/2013 | Chung et al. | |
| 2014/0196522 A1 | 7/2014 | Borini et al. | |
| 2015/0002178 A1 | 1/2015 | Herb et al. | |
| 2015/0346129 A1 | 12/2015 | Kersey | |
| 2016/0115395 A1* | 4/2016 | Rustad | G05B 15/02 700/282 |
| 2018/0052133 A1* | 2/2018 | Godfrey | G01N 27/226 |
| 2019/0041880 A1* | 2/2019 | Grassi | G05D 21/02 |

FOREIGN PATENT DOCUMENTS

| | | |
|---|---|---|
| CN | 108152361 A | 6/2018 |
| DE | 2701197 A1 | 7/1978 |
| JP | H08210890 A | 8/1996 |
| KR | 20180038839 A | 4/2018 |
| WO | 03001167 A2 | 1/2003 |
| WO | 2008101161 A1 | 8/2008 |
| WO | 2012007347 A1 | 1/2012 |

OTHER PUBLICATIONS

"International Search Report and Written Opinion of the International Searching Authority, International Application No. PCT/GB2018/053316, dated Feb. 4, 2019, 14 pp."

"Invitation to Pay Additional Fees and, where Applicable, Protest Fee, International Application No. PCT/GB2019/052979, dated Feb. 19, 2020, 11 pp."

"Lyons, "A Quadrature Signals Tutorial: Complex, But Not Complicated", DSP Related.com, Apr. 12, 2013, 27 pp., available online from https://www.dsprelated.com/showarticle/192.php [accessed May 31, 2019]".

"Meettechniek.info, "Measuring capacitance & ESR", Jan. 20, 2014, 6 pp., available online from https://meettechniek.info/passive/capacitance.html [accessed May 31, 2019]".

"Patents Act 1977: Combined Search and Examination Report under Sections 17 and 18(3), UKIPO Application No. GB1718916.8, dated May 8, 2018, 5 pp.".

"Patents Act 1977: Combined Search and Examination Report under Sections 17 and 18(3), UKIPO Application No. GB1819732.7, dated Jun. 4, 2019, 11 pp.".

Fuchs, et al., "Capacitive Sensing In Process Instrumentation", Metrology and Measurements Systems, vol. XVI, No. 4, 2009, pp. 557-568.

Jaegle, et al., "Thermal-electrical impedance spectroscopy for fluid characterisation", Procedia Engineering (Special Issue: Proceedings of the 30th anniversary Eurosensors Conference—Eurosensors 2016, 4-7. Sep. 2016, Budapest, Hungary), vol. 168, pp. 770-773.

* cited by examiner

S201 measure conductivity $\sigma_{meas}$ and capacitance $C_{meas}$ of fluid flowing through cell 610

S203 Determine value of $\varepsilon_r$ using equation (1) and measured values of conductivity $\sigma_{meas}$ and capacitance $C_{meas}$.

S205 Determine current temperature $T_{curr}$ of fluid in cell 610 by inserting value of $\varepsilon_r$ calculated at step S203 into equation (2).

S207 Determine conductivity $\sigma_{town}$ of local town water at $T_{curr}$ by means of stored equation linking conductivity and temperature of local town water as delivered to the plant.

S209 Calculate the difference $\sigma_{diff}$ between measured conductivities $\sigma_{meas}$ and $\sigma_{town}$, $\sigma_{meas} - \sigma_{town} = \sigma_{diff}$.

S211 If $\sigma_{diff}$ is greater than a threshold difference $\sigma_{delta}$ then display message 'cleaning in progress' and move to step S201 else continue to step S213.

S213 display message 'cleaning complete'.

FIG. 21

S301 measure conductivity $\sigma_{meas}$ and capacitance $C_{meas}$ of fluid flowing through cell 610.

S303 Determine value of $\varepsilon_r$ using equation (1) and measured values of conductivity $\sigma_{meas}$ and capacitance $C_{meas}$.

S305 Determine current temperature $T_{curr}$ of fluid in cell 610 by inserting value of $\varepsilon_r$ calculated at step S303 into equation (2).

S307 Determine conductivity $\sigma_{flush}$ of flushing fluid at $T_{curr}$ by means of stored equation linking conductivity and temperature of flushing fluid as introduced to the plant.

S309 Calculate the magnitude of the difference $|\sigma_{diff}|$ between measured conductivities $\sigma_{meas}$ and $\sigma_{flush}$, $|\sigma_{meas} - \sigma_{flush}| = |\sigma_{diff}|$.

S311 Store the value of $|\sigma_{diff}|$ in a memory of the system 600. If the number of stored values in respect of current flushing operation exceeds 10, the system 600 moves to step S313 else it moves to step S301.

S313 If $|\sigma_{diff}|$ is greater than a threshold difference $\sigma_{delta}$ then continue at step S315 else continue at step S319.

S315 Display message 'cleaning in progress'. Calculate best-fit polynomial expression for $|\sigma_{diff}|$ as a function of time to obtain time to completion ($|\sigma_{diff}| \leq \sigma_{delta}$) and display "Time remaining before cleaning is complete: Xh :Ymins" Continue at step S301.

S317 displays the message 'cleaning complete' and generates an audible alert to inform an operator that cleaning is now complete.

FIG. 24 o = Fluid under test
x = Reference fluids 1-4

APPARATUS FOR MONITORING A FLUID

RELATED APPLICATIONS

This application is a 35 U.S.C. § national stage application of PCT Application No. PCT/GB2019/052979, filed on Oct. 18, 2019, which claims priority from Great Britain Patent Application No. 1819732.7, filed on Dec. 3, 2018 and from Great Britain Patent Application No. 1817278.3, filed Oct. 24, 2018, the contents of all of which are incorporated herein by reference in their entireties. The above-referenced PCT International Application was published in the English language as International Publication No. WO 2020/084281 A2 on Apr. 30, 2020.

TECHNICAL FIELD

The present invention relates to apparatus and a method for monitoring a fluid.

BACKGROUND

There are various applications where it is desirable to monitor a property of a fluid. One application is cleaning of debris and residue from internal surfaces in industrial processing plants which process liquids, such as plants processing chemicals, foodstuffs, beverages and other fluids. Such cleaning processes may be referred to as 'clean in place' (CIP) processes. Sodium hydroxide solution is often employed in CIP processes. An aqueous solution of sodium hydroxide is pumped through pipework of the plant to clean the internal surfaces.

There is a need to determine when it is safe to reuse the processing plant after cleaning. It is important to thoroughly cleanse the internal surfaces of sodium hydroxide (or other cleaning substance) following treatment so as to avoid contamination of liquids subsequently passed through the plant with sodium hydroxide. Removal of sodium hydroxide may be performed by flushing of the internal surfaces of the plant with local town water. Flushing with town water is typically performed until the concentration of sodium hydroxide in the town water that has been flushed through the plant is at a sufficiently low value to permit the plant to resume operations.

It is an aim of the present invention to address disadvantages associated with the prior art.

SUMMARY OF THE INVENTION

An aspect provides apparatus for measuring at least one property of a fluid, the apparatus comprising:
a processing apparatus configured to:
receive a sense signal from a capacitive fluid sensor comprising a first electrode and a second electrode with a sensing region between the electrodes;
receive an alternating drive signal applied to the capacitive fluid sensor;
determine a complex impedance of the fluid sensor based on the sense signal and the drive signal, the complex impedance comprising a real (in-phase) component indicative of a conductivity quantity of a fluid in the sensing region and an imaginary (quadrature) component indicative of a capacitance quantity of the fluid sensor;
determine a temperature of the fluid in dependence on at least the determined capacitance quantity of the fluid sensor.

Using the capacitive fluid sensor to determine temperature has an advantage that a single sensor is used. The exact same body of water is being sensed to determine both temperature and conductivity, i.e. the two measurements are physically co-located. Another advantage is speed of response. A conventional thermometer has to reach thermal equilibrium with the body being measured, which introduces a delay before an accurate temperature measurement can be read. Another advantage is high resolution measurements of temperature, such as <0.1K.

Optionally, the processing apparatus is configured to determine a temperature-adjusted conductivity quantity in dependence on the determined conductivity quantity and the determined temperature of the fluid.

Optionally, the processing apparatus is configured to determine a dielectric constant quantity indicative of a dielectric constant of the fluid in dependence on the determined capacitance quantity and the step of determining temperature of the fluid uses the determined dielectric constant quantity.

Optionally, the processing apparatus is configured to determine the temperature by one of: a look-up table; an equation linking temperature to dielectric constant.

Optionally, the processing apparatus is configured to correct the capacitance quantity for at least one parasitic effect.

Optionally, the at least one parasitic effect is at least one of: electrode polarisation; lead inductance; capacitance of an analog-to-digital converter.

Optionally, the processing apparatus is configured to calculate a corrected capacitance quantity, being an expected value of capacitance quantity if the at least one parasitic effect were eliminated, based at least in part on the conductivity quantity.

Optionally, the apparatus is configured to calculate, by extrapolation, a corrected capacitance value based on the measured capacitance quantity and conductivity quantity and data in respect of a relationship between capacitance quantity and conductivity quantity, the corrected capacitance value corresponding to the expected value if the fluid was of substantially zero conductivity.

Optionally, the processing apparatus is configured to compare a value corresponding to at least one property of the fluid determined by the apparatus with a reference value of the at least one property of the fluid and to provide an output in dependence on the comparison.

Optionally, the processing apparatus is configured to compare the at least one property of the fluid with a reference value of the at least one property of the fluid at the current temperature of the fluid.

Optionally, the at least one property includes at least one selected from amongst a conductivity of the fluid and a dielectric constant of the fluid.

Optionally, the at least one property is conductivity of a liquid comprising an aqueous solution of water and an ionic substance and the reference value is a conductivity value of the liquid indicative of a concentration of the ionic substance in the aqueous solution.

Optionally, the processing apparatus is configured to output:
an indication when the conductivity of the liquid has reached the reference value;
an indication of a time when the conductivity of the liquid will reach the reference value.

Optionally, the ionic substance is at least one of: sodium hydroxide; sodium chloride; calcium chloride; a cleaning solution.

Optionally, the processing apparatus is configured to use the sense signal and the drive signal in an algorithmic model of the apparatus to determine the complex impedance. It will be understood that the complex impedance may be determined in other ways.

Optionally, the processing apparatus is configured to:
determine a ratio of:
(i) an averaging filtered output of the sense signal multiplied with a digital oscillator, the filtered output having an in-phase sense signal component and a quadrature sense signal component;
(ii) an averaging filtered output of the drive signal multiplied with a digital oscillator, the filtered output having an in-phase drive signal component and a quadrature drive signal component;
use the determined ratio in an algorithmic model of the apparatus to determine the complex impedance of the fluid sensor.

The apparatus may further comprise: the capacitive fluid sensor; and an alternating signal source configured to apply the alternating drive signal to the capacitive fluid sensor.

An aspect provides a processing plant comprising:
a pipe or flow line;
a capacitive fluid sensor in the pipe or flow line;
an alternating signal source configured to apply the alternating drive signal to the capacitive fluid sensor apparatus;
a processing apparatus according to another aspect.

An aspect provides a method of measuring at least one property of a fluid comprising:
receiving a sense signal from a capacitive fluid sensor comprising a first electrode and a second electrode with a sensing region between the electrodes;
receiving an alternating drive signal applied to the capacitive fluid sensor;
determining a complex impedance of the fluid sensor based on the sense signal and the drive signal, the complex impedance comprising a real (in-phase) component indicative of a conductivity quantity of a fluid in the sensing region and an imaginary (quadrature) component indicative of a capacitance quantity of the fluid sensor;
determining a temperature of the fluid in dependence on at least the determined capacitance quantity of the fluid sensor.

An aspect provides apparatus for measuring at least one property of a fluid, the apparatus comprising:
a processing apparatus configured to:
receive a sense signal from a capacitive fluid sensor comprising a first electrode and a second electrode with a sensing region between the electrodes;
receive an alternating drive signal applied to the capacitive fluid sensor;
determine a complex impedance of the fluid sensor based on the sense signal and the drive signal, the complex impedance comprising a real (in-phase) component indicative of a conductivity quantity of a fluid in the sensing region and an imaginary (quadrature) component indicative of a capacitance quantity of the fluid sensor;
determine a value corresponding to a temperature of the fluid in dependence on at least the determined capacitance quantity of the fluid sensor, and/or generate a signal corresponding to a temperature of the fluid in dependence on at least the determined capacitance quantity of the fluid sensor.

An aspect provides a method of measuring at least one property of a fluid comprising:
receiving a sense signal from a capacitive fluid sensor comprising a first electrode and a second electrode with a sensing region between the electrodes;
receiving an alternating drive signal applied to the capacitive fluid sensor;
determining a complex impedance of the fluid sensor based on the sense signal and the drive signal, the complex impedance comprising a real (in-phase) component indicative of a conductivity quantity of a fluid in the sensing region and an imaginary (quadrature) component indicative of a capacitance quantity of the fluid sensor;
determining a value corresponding to a temperature of the fluid in dependence on at least the determined capacitance quantity of the fluid sensor, and/or generating a signal corresponding to a temperature of the fluid in dependence on at least the determined capacitance quantity of the fluid sensor.

An aspect provides an apparatus for monitoring a fluid under test, the apparatus comprising:
a processing apparatus comprising a processor and a memory configured to store data indicative of at least one reference fluid, wherein the stored data for the, or each, reference fluid comprises data indicative of a capacitance quantity and a conductivity quantity over a range of temperatures, the processing apparatus configured to:
receive a sense signal from a capacitive fluid sensor;
receive an alternating drive/reference signal;
determine a measured value indicative of a conductivity quantity of the fluid under test based on the sense signal and the drive/reference signal;
determine a measured value indicative of a capacitance quantity of the fluid sensor based on the sense signal and the drive/reference signal;
determine a measured temperature of the fluid under test;
determine if the fluid under test is similar to the reference fluid, or one of the plurality of reference fluids, based on:
(i) the measured value indicative of the conductivity quantity, the measured value indicative of the capacitance quantity; and
(ii) the stored data indicative of the conductivity quantity for the reference fluid(s) at the measured temperature and the stored data indicative of the capacitance quantity for the reference fluid(s) at the measured temperature.

The reference fluid may be any fluid which there is a need to identify. This arrangement can be used on a variety of fluids. One example is an aqueous solution with one or more additives. The reference fluids may be beverages with different compositions, e.g. different ingredients or similar ingredients in differing relative amounts. Another example is an oil-based liquid or solution or an emulsion of oil and water.

The data for the reference fluid(s) may be acquired using the same apparatus, or by a different apparatus. For example, data for the reference fluid(s) may be acquired in a laboratory by a first apparatus and the measured values and comparison may be performed by a second apparatus deployed in a factory, a business premises, a home or some other location where identification of a fluid is required.

The processing apparatus may be a single processing apparatus, or multiple processing apparatuses. For example, a first processing apparatus may determine the measured values and a second processing apparatus may determine if the fluid under test is similar to one of the reference fluid(s). For example, the first processing apparatus may be co-located with the fluid sensor and the second processing apparatus may be located separately or remotely from the fluid sensor, such as a server or cloud-based processing apparatus.

The measured value indicative of a conductivity quantity of the fluid under test may be a real (in-phase) output of a processing unit which determines a complex impedance of the fluid sensor. A real (in-phase) component of a complex impedance of the fluid sensor varies according to conductivity of the fluid under test. Therefore, the real (in-phase) output of complex impedance is indicative of the conductivity of the fluid under test.

The measured value indicative of a capacitance quantity of the fluid sensor may be an imaginary (quadrature) output of a processing unit which determines a complex impedance of the fluid sensor. An imaginary (quadrature) component of complex impedance of the fluid sensor varies according to a dielectric constant or relative permittivity of the fluid under test. Therefore, the imaginary (quadrature) output of complex impedance is indicative of the capacitance of the fluid sensor.

The measured temperature of the fluid under test may be obtained by means of a temperature sensor or detector such as an infra-red temperature sensor, a thermocouple-based temperature sensor, a resistance temperature detector, a thermistor or any other suitable sensor or detector.

Some optional features associated with aspects of the invention are set out in claims 24 to 31, 34 to 36 and 38.

An aspect provides an apparatus for measuring at least one property of a fluid under test, the apparatus comprising:
a processing apparatus comprising a processor and a memory configured to store data indicative of a relationship between an expected value indicative of a capacitance quantity and an expected value indicative of a conductivity quantity for a reference fluid over a range of temperatures, the processing apparatus configured to:
receive a sense signal from a capacitive fluid sensor;
receive an alternating drive/reference signal;
determine a measured value indicative of a conductivity quantity of the fluid based on the sense signal and the drive/reference signal;
determine a measured value indicative of a capacitance quantity of the fluid sensor based on the sense signal and the drive/reference signal; and
(i) determine an expected value indicative of the capacitance quantity of the fluid under test by using the measured value indicative of the conductivity quantity and the stored data; and determine a difference between the expected value indicative of the capacitance quantity and the measured value indicative of the capacitance quantity; or
(ii) determine an expected value indicative of the conductivity quantity of the fluid under test by using the measured value indicative of the capacitance quantity and the stored data; and determine a difference between the expected value indicative of the conductivity quantity and the measured value indicative of the conductivity quantity.

An advantage of this arrangement is that it allows a property of a fluid to be measured independently of temperature. That is, it allows a property of a fluid to be determined without a need to measure temperature. This can avoid the need for a separate temperature sensor, which can reduce cost of the apparatus. Temperature measurements can take an undesirably long time as it can require a temperature sensor to come into thermal equilibrium with a fluid under test. Temperature sensors can have a relatively low accuracy. Avoiding the need to make temperature measurements can allow an improved speed and/or accuracy of measuring the property of the fluid.

This arrangement can be used on a variety of fluids. One example is an aqueous solution with a contaminant (e.g. a cleaning agent), where the property to be measured is the concentration of the contaminant. Another example is a beverage where a measured value indicative of a capacitance quantity varies with an alcoholic content of the beverage. Another example is an oil-based liquid or solution or an emulsion of oil and water.

The processing apparatus may be a single processing apparatus, or multiple processing apparatuses. For example, a first processing apparatus may determine the measured values and a second processing apparatus may determine if the fluid under test is similar to one of the reference fluid(s). For example, the first processing apparatus may be co-located with the fluid sensor and the second processing apparatus may be located separately or remotely from the fluid sensor, such as a server or cloud-based processing apparatus.

The measured value indicative of a conductivity quantity of the fluid under test may be a real (in-phase) output of a processing unit which determines a complex impedance of the fluid sensor. A real (in-phase) component of a complex impedance of the fluid sensor varies according to conductivity of the fluid under test. Therefore, the real (in-phase) output of complex impedance is indicative of the conductivity of the fluid under test.

The measured value indicative of a capacitance quantity of the fluid sensor may be an imaginary (quadrature) output of a processing unit which determines a complex impedance of the fluid sensor. An imaginary (quadrature) component of complex impedance of the fluid sensor varies according to a dielectric constant or relative permittivity of the fluid under test. Therefore, the imaginary (quadrature) output of complex impedance is indicative of the capacitance of the fluid sensor.

Some optional features associated with aspects of the invention are set out in claims 40 to 47, 50 to 52 and 54.

The method may include steps corresponding to any of the functionality of the processing apparatus as defined above, or below.

An aspect provides apparatus for measuring at least one property of a fluid, the apparatus comprising:
a capacitive fluid sensor comprising a first electrode and a second electrode with a sensing region between the electrodes;
an alternating signal source configured to apply an alternating drive signal to the capacitive fluid sensor; and
a processing apparatus configured to:
receive a sense signal from the capacitive fluid sensor;
receive the alternating drive signal;
determine a complex difference signal comprising an in-phase difference component between the drive signal and the sense signal and a quadrature difference component between the drive signal and the sense signal;
determine the at least one property of the fluid based on both the in-phase phase difference component and the quadrature difference component of the difference signal by compensating for an effect on the complex difference signal due to at least one parasitic element of the apparatus.

It is to be understood that the complex difference signal may comprise a ratio, for example a ratio of two complex numbers, the ratio being indicative of a difference between the drive signal and the sense signal. It is to be understood that the ratio of two complex numbers may itself be a complex number. In the case that the two complex numbers represent signals such as the drive signal and the sense signal, the complex ratio may comprise an in-phase difference component between the drive signal and the sense signal and a quadrature difference component between the drive signal and the sense signal. Thus, the ratio may be considered to represent a complex difference signal between the drive signal and sense signal.

The complex difference signal may comprise a ratio of the sense signal and the drive/reference signal. The sense signal may be represented as a complex number with an in-phase component and a quadrature component. The drive signal may be represented as a complex number with an in-phase component and a quadrature component. The complex difference signal obtained by a ratio of the sense signal and the drive signal may also be represented as a complex number with an in-phase difference component and a quadrature difference component. The complex difference signal may represent (i) a phase difference between the sense signal and the drive/reference signal and (ii) a magnitude equal to a ratio of the magnitudes of the sense signal and the drive/reference signal.

Optionally, the processing apparatus is configured to determine an in-phase component of the sense signal and a quadrature component of the sense signal.

Optionally, the processing apparatus is configured to determine the in-phase component of the sense signal and the quadrature component of the sense signal by an averaging filtering operation performed over a plurality of cycles of the alternating drive signal.

Optionally, the processing apparatus is configured to determine an in-phase component of the drive signal and a quadrature component of the drive signal.

Optionally, the processing apparatus is configured to determine an in-phase component of the drive signal and a quadrature component of the drive signal by an averaging filtering operation performed over a plurality of cycles of the alternating drive signal.

Optionally, the processing apparatus is configured to:
determine the in-phase component of the sense signal and the quadrature component of the sense signal by an averaging filtering operation performed over a plurality of cycles of the alternating drive signal;
determine an in-phase component of the drive signal and a quadrature component of the drive signal by an averaging filtering operation performed over a plurality of cycles of the alternating drive signal;
determine the in-phase difference component based on the filtered in-phase component of the sense signal and the filtered in-phase component of the drive signal; and
determine the quadrature difference component based on the filtered quadrature component of the sense signal and the filtered quadrature component of the drive signal.

Optionally, the processing apparatus is configured to use the in-phase difference component and the quadrature difference component in an algorithmic model of the apparatus to determine the dielectric constant of the fluid, wherein the algorithmic model includes the at least one parasitic element of the apparatus.

It is to be understood that, herein, by the term 'dielectric constant' of a medium is meant the 'relative dielectric permittivity' of the medium.

Optionally, the processing apparatus is configured to use the in-phase difference component and the quadrature difference component in an algorithmic model of the apparatus to determine conductivity of the fluid, wherein the algorithmic model includes the at least one parasitic element of the apparatus.

Optionally, the processing apparatus is configured to compare the in-phase difference component and the quadrature difference component to a plurality of stored compensated data values to determine the dielectric constant of the fluid, wherein the stored compensated data values compensate for an effect of at least one parasitic element of the apparatus.

Optionally, the processing apparatus is configured to compare the in-phase difference component and the quadrature difference component to a plurality of stored compensated data values to determine conductivity of the fluid, wherein the stored compensated data values compensate for an effect of at least one parasitic element of the apparatus.

Optionally, the processing apparatus is configured to measure at least one property of a fluid with a conductivity of up to 200 mS/m.

Optionally, the processing apparatus is configured to sample the sense signal at a sampling frequency, and a frequency of the alternating current drive signal is higher than the sampling frequency.

Optionally, the processing apparatus is configured to:
provide a digital oscillator with an in-phase oscillator output and a quadrature oscillator output;
provide a phase-locked loop which is configured to use the in-phase oscillator output and the quadrature oscillator output to achieve synchronisation between the drive signal and the digital oscillator.

Optionally, the phase-locked loop is a Costas loop.

Optionally, the processing apparatus is configured to use the in-phase oscillator output and the quadrature oscillator output to process the sense signal when a locked synchronisation state has been achieved.

Optionally, the apparatus comprises an analogue-to-digital converter and the processing apparatus is configured to:
sample the sense signal at a first time and sample the drive signal at a second time which is offset from the first time; and
apply a correction factor to the sampled signals to correct for the offset times at which the signals were sampled.

Optionally, the parasitic element is lead inductance. The lead inductance is inductance of one or more of: a lead connecting the drive signal generator to the capacitive fluid sensor; a lead connecting the capacitive fluid sensor to the processing apparatus.

Optionally, the processing stage is a digital signal processing stage.

Optionally, the apparatus comprises a temperature sensor, and the processing apparatus is configured to:
determine temperature of the fluid;
determine conductivity using the determined temperature.

Optionally, the capacitive fluid sensor is configured to monitor a flowing fluid, wherein the first electrode and the second electrode define a fluid flow channel between the electrodes.

Optionally, the first electrode is a tubular electrode and the second electrode is located within the first electrode.

The processing apparatus may be configured to receive the alternating drive signal directly from the alternating signal source, or from some other node which is external to the capacitive fluid sensor. This provides the processing apparatus with a signal which is indicative of the drive signal. The processing apparatus can use the drive signal for comparison with the sense signal to determine the effect of the fluid on the capacitive fluid sensor.

Another aspect provides a processing apparatus for measuring at least one property of a fluid, the processing apparatus configured to:
  receive a sense signal from a capacitive fluid sensor;
  receive an alternating drive signal which has been applied to the capacitive fluid sensor;
  determine a complex difference signal comprising an in-phase difference component between the drive signal and the sense signal and a quadrature difference component between the drive signal and the sense signal;
  determine the at least one property of the fluid based on both the in-phase phase difference component and the quadrature difference component of the difference signal by compensating for an effect on the complex difference signal due to at least one parasitic element of the apparatus.

Another aspect provides a method of measuring at least one property of a fluid, the method comprising:
  receiving a sense signal from a capacitive fluid sensor;
  receiving an alternating drive signal which has been applied to the capacitive fluid sensor;
  determining a complex difference signal comprising an in-phase difference component between the drive signal and the sense signal and a quadrature difference component between the drive signal and the sense signal;
  determining the at least one property of the fluid based on both the in-phase phase difference component and the quadrature difference component of the difference signal by compensating for an effect on the complex difference signal due to at least one parasitic element of the apparatus.

Another aspect provides a computer program product comprising a machine-readable medium carrying instructions which, when executed by a processor, cause the processor to perform the method defined above or described herein.

Another aspect provides apparatus for measuring at least one property of a fluid, the apparatus comprising a processing apparatus configured to:
  receive a sense signal from a capacitive fluid sensor;
  receive an alternating drive signal which has been applied to the capacitive fluid sensor;
  determine a complex difference signal comprising an in-phase difference component between the drive signal and the sense signal and a quadrature difference component between the drive signal and the sense signal;
  determine the at least one property of the fluid based on both the in-phase phase difference component and the quadrature difference component of the difference signal by compensating for an effect on the complex difference signal due to at least one parasitic element of the apparatus.

An advantage of at least one example is that it is possible to measure dielectric constant for fluids with a high conductivity. Conventionally, it has not been possible to measure dielectric constant of a high conductivity fluid using a capacitive sensor as the effect of the fluid on a capacitive sensor has been considered too small to measure accurately. Also, parasitic elements of the apparatus can contribute to the measured signal, and can mask a signal contributed by the capacitive sensor. This makes it difficult to measure a contribution by the capacitive sensor.

The dielectric loss of the fluid is a function of its conductivity. Therefore, it is also possible to make high resolution measurements of conductivity without the need for platinum electrodes.

A relatively low radio frequency alternating frequency signal (e.g. <10 MHz), together with digital signal processing, allows measurements to be made using low cost readily available components.

An aspect provides apparatus for measuring at least one property of a fluid, the apparatus comprising:
  a capacitive fluid sensor comprising a first electrode and a second electrode with a sensing region between the electrodes;
  an alternating signal source configured to apply an alternating drive signal to the capacitive fluid sensor; and
  a processing apparatus configured to:
    receive a sense signal from the capacitive fluid sensor;
    receive the alternating drive signal;
    determine a complex ratio of the drive signal and sense signals comprising an in-phase difference component between the drive signal and the sense signal and a quadrature difference component between the drive signal and the sense signal;
    determine the at least one property of the fluid based on both the in-phase phase difference component and the quadrature difference component of the difference signal by compensating for an effect on the complex difference signal due to at least one parasitic element of the apparatus.

In a further aspect of the invention for which protection is sought there is provided apparatus for measuring at least one property of a fluid, the apparatus comprising:
  a processing apparatus configured to:
    receive a sense signal from a capacitive fluid sensor comprising a first electrode and a second electrode with a sensing region between the electrodes;
    receive an alternating drive signal applied to the capacitive fluid sensor;
    determine a signal comprising an in-phase difference component between the drive signal and the sense signal and a quadrature difference component between the drive signal and the sense signal;
    determine the at least one property of the fluid based on both the in-phase phase difference component and the quadrature difference component of the difference signal.

The at least one property may be a conductivity, a dielectric constant, a temperature or any other suitable property.

The signal determined by the apparatus may be a ratio of the sense signal and drive signal, the ratio being a complex quantity (i.e. having amplitude and phase). It is to be understood that the real and imaginary components of the ratio may be considered to represent, respectively, an in-phase difference component between the drive signal and the sense signal and a quadrature difference component between the drive signal and the sense signal. The ratio as a function of time may therefore be considered to represent a complex difference signal in respect of the sense and drive signals.

The apparatus may further comprise:
  the capacitive fluid sensor; and
  an alternating signal source configured to apply the alternating drive signal to the capacitive fluid sensor.

The apparatus may be configured to determine at least one of a capacitance quantity indicative of a capacitance of the capacitive fluid sensor and a conductivity quantity indicative of a conductivity of a fluid in the sensing region.

The capacitance quantity may be a value of capacitance (e.g. in units of Farads) or a quantity corresponding to the capacitance, for example a data value that may be converted to units of Farads by means of a suitable conversion factor. Similarly, the conductivity quantity may be a value of conductivity (e.g. in units of mS/m) or a quantity corresponding to the conductivity, for example a data value that may be converted to units of mS/m by means of a suitable conversion factor.

The apparatus may be configured to determine a capacitance quantity indicative of a capacitance of the capacitive fluid sensor and to correct the capacitance quantity for at least one parasitic effect.

The apparatus may be configured to determine the conductivity quantity indicative of a conductivity of the fluid and to calculate a corrected capacitance quantity, being an expected value of capacitance quantity if the at least one parasitic effect were eliminated, based at least in part on the conductivity quantity.

Optionally, the apparatus is configured to calculate, by extrapolation, a corrected capacitance value based on the measured capacitance quantity and conductivity quantity and data in respect of a relationship between capacitance quantity and conductivity quantity, the corrected capacitance value corresponding to the expected value if the fluid was of substantially zero conductivity.

This feature has the advantage that, in the case that the fluid is an aqueous solution, compensation for the effects of electrode polarisation may be performed.

Optionally, the apparatus is configured to determine a dielectric constant quantity indicative of a dielectric constant of the fluid in the sensing region.

The dielectric constant quantity may be a value of dielectric constant or a quantity corresponding to the dielectric constant.

Optionally, the apparatus is configured to calculate a temperature of the fluid in dependence on the dielectric constant quantity.

Temperature may for example be calculated by means of an equation equating temperature and dielectric constant.

The apparatus may be configured to compare a value corresponding to at least one property of the fluid determined by the apparatus with a reference value of the at least one property of the fluid and to provide an output in dependence on the comparison.

The apparatus may for example perform the comparison by calculating a difference between the value determined by the apparatus and the reference value. The apparatus may provide the output in dependence on the difference.

The apparatus may be further configured to calculate a current temperature of the fluid and to compare the at least one property of the fluid with a reference value of the at least one property of the fluid at the current temperature of the fluid.

The apparatus may for example employ an equation of look-up table (LUT) to determine the reference value of the at least one property (such as conductivity) at the current temperature. This may be particularly important in applications where a value of interest, such as dielectric constant, or conductivity, varies as a function of temperature, for examples in measurement so dielectric constant or conductivity of water, dilute aqueous solutions, or other liquids. In such cases it may be important to compare the measured value of dielectric constant of the fluid with a corresponding reference value of the fluid at the same temperature.

Optionally, the at least one property includes at least one selected from amongst a conductivity of the fluid and a dielectric constant of the fluid.

Apparatus for measuring temperature of a fluid at least one property of a fluid, the apparatus being configured to apply an alternating drive signal to a capacitive fluid sensor; and
   receive a sense signal from the capacitive fluid sensor,
      the apparatus being configured to determine the temperature of the fluid based at least in part on the drive signal and the sense signal.

The apparatus may be configured to determine a complex difference signal comprising an in-phase difference component between the drive signal and the sense signal and a quadrature difference component between the drive signal and the sense signal, and to determine the temperature of the fluid based at least in part on the difference signal.

Apparatus for measuring temperature of a fluid at least one property of a fluid, the apparatus being configured to apply an alternating drive signal to a capacitive fluid sensor; and
   receive a sense signal from the capacitive fluid sensor,
      the apparatus being configured to determine a complex difference signal comprising an in-phase difference component between the drive signal and the sense signal and a quadrature difference component between the drive signal and the sense signal;
   determine the temperature of the fluid based on the difference signal.

The apparatus may comprise a capacitive fluid sensor comprising a first electrode and a second electrode with a sensing region between the electrodes.

The apparatus may further comprise an alternating signal source configured to apply the alternating drive signal to the capacitive fluid sensor.

Apparatus for measuring temperature of a fluid at least one property of a fluid, the apparatus being configured to apply an alternating drive signal to a capacitive fluid sensor comprising first and second electrodes having a sensing region therebetween; and
   receive a sense signal from the capacitive fluid sensor,
      the apparatus being configured to determine a complex difference signal comprising an in-phase difference component between the drive signal and the sense signal and a quadrature difference component between the drive signal and the sense signal;
   determine the temperature of the fluid based on the difference signal.

The apparatus may be configured to determine the temperature of the fluid based on both the in-phase phase difference component and the quadrature difference component of the difference signal.

Apparatus for measuring temperature of a fluid, the apparatus being configured to obtain a measurement of a first parameter indicative of conductivity of the fluid and a second parameter indicative of capacitance of the fluid, and determine temperature of the fluid in dependence on the first and second parameters.

Apparatus for measuring temperature of a fluid, the apparatus being configured to obtain a measurement of a first parameter indicative of conductivity of the fluid and a second parameter indicative of dielectric constant of the fluid, the apparatus being configured to determine a value indicative of temperature of the fluid in dependence on the first and second parameters.

Apparatus for measuring temperature of a fluid, the apparatus being configured to obtain a measurement of a first parameter indicative of dielectric constant of the fluid and to determine a temperature of the fluid in dependence on the dielectric constant.

The apparatus may be configured to determine the temperature of the fluid by reference to at least one selected from amongst a look-up table and an algorithm relating temperature to dielectric constant.

Apparatus configured to provide an output in dependence on a concentration of a substance in a fluid, the apparatus being configured to receive a source signal from an alternating signal source and a sense signal being a signal across a capacitive fluid sensor when the source signal is applied thereto, the apparatus being configured to provide the output in dependence at least in part on the drive signal and the sense signal.

Embodiments of the present invention have the advantage that a signal indicative of concentration may be obtained in a relatively rapid, non-invasive manner and without a requirement to extract fluid from an environment in which the fluid is present, such as a pipe or vessel.

The apparatus may be configured to determine a complex difference signal comprising an in-phase difference component between the drive signal and the sense signal and a quadrature difference component between the drive signal and the sense signal, and to provide the output in dependence at least in part on the difference signal.

The apparatus may be configured to obtain a measured value indicative of at least one property of the fluid and to provide the output in dependence on a result of a comparison of the value with a stored reference value.

The stored reference value may for example be a value corresponding to that of a reference fluid, optionally the fluid with substantially none of the substance present in it or a baseline concentration of the substance present. The apparatus may then compare the measured value with the stored reference value and provide an output in dependence on the comparison. For example, the apparatus may provide an output indicative of when the measured value indicates that the concentration of the substance is below a threshold concentration. Alternatively, or in addition, the apparatus may provide an output indicative of when the measured value indicates that the concentration of the substance is above a threshold concentration. Alternatively, or in addition, the apparatus may provide an output indicative of when the measured value indicates that the concentration of the substance is substantially equal to a threshold concentration. The threshold concentration may correspond to an amount by which the concentration of the substance in the fluid exceeds that of the substance in the reference fluid. The amount of the substance in the reference fluid may thus be considered to be a 'substantially zero' amount although at least a trace amount may be present.

The fluid may for example be water and the substance may be an ionic substance such as sodium hydroxide, sodium chloride, calcium chloride or any other suitable substance. Thus, the fluid may comprise an aqueous solution of the substance, the substance being dissolved therein. The sample of fluid with substantially none of the substance present in it or a baseline concentration of the substance present may be water from a source such as a source of mains town water. The town water may have a certain amount of the substance therein. The apparatus may be configured to provide the output in dependence on the concentration of the substance in the fluid.

Thus, in the case that the apparatus is used to monitor the concentration of sodium hydroxide in tap water (town water) being used to flush a system that has been cleaned using sodium hydroxide, the critical factor may be to determine when the concentration of sodium hydroxide in tap water that has been flushed through the system is no more than a certain amount above that of the tap water being used to flush the system. Embodiments of the present invention may accomplish this task by comparing a measured value indicative of concentration of sodium hydroxide in the water that has been flushed through the system with a corresponding value for town water. The apparatus may then provide the output in dependence on the comparison.

The apparatus may take into account the temperature of the fluid. Temperature may be taken into account based on a measurement of dielectric constant of the fluid. The apparatus may be provided with means for determining temperature based on a measurement of dielectric constant, such as an equation linking dielectric constant with fluid temperature or a look-up table (LUT) linking dielectric constant with fluid temperature.

It is to be understood that, for aqueous solutions containing ionic substances such as sodium hydroxide, sodium chloride or any other ionic substance of interest, at relatively low concentrations of dissolved ions the dielectric constant $\varepsilon_r$ of the solution may be substantially the same as that of water with a substantially zero concentration of the ions therein. Since the dielectric constant $\varepsilon_r$ of water is known to be a function of temperature, measurements of the dielectric constant $\varepsilon_r$ of the liquid containing the (relatively low) concentration of dissolved ions is capable of providing a precise and accurate measurement of the temperature of the liquid.

Embodiments of the present invention permit measurements of dielectric constant based on measurements of capacitance of a capacitive fluid sensor and conductivity of the medium therebetween. It is to be understood that measurements of capacitance of the fluid sensor may be affected by electrode polarisation, which effect increases with increasing ion concentration. Consequently, the value of dielectric constant of the fluid calculated using measured values of capacitance provide erroneous results. Embodiments of the present invention permit the effects of electrode polarisation due to the dissolved ions to be compensated for. In one aspect, compensation is achieved by measuring the capacitance and conductivity of a liquid and determining what the capacitance of the liquid would be if the conductivity of the liquid was substantially zero. This may be done if the gradient of a plot of capacitance as a function of conductivity for the aqueous solution of interest is known, by extrapolation. The corresponding value of capacitance at substantially zero conductivity (i.e. a value of capacitance compensated for the effects of electrode polarisation) may then be used to calculate the dielectric constant $\varepsilon_r$ of the solution. This value of dielectric constant $\varepsilon_r$ can then be employed to obtain a value of temperature assuming that the dielectric constant $\varepsilon_r$ of the liquid so calculated is substantially equal to the of water at the same temperature.

Thus, given information in respect of the relationship between the dielectric constant $\varepsilon_r$ of water and temperature (such as an algorithm equating the two, a look up table or other form) it is possible to calculate the temperature of the liquid from the information. It is to be understood that electrical measurements of capacitance and conductivity may be made relatively quickly, permitting relatively rapid determination of the temperature of a liquid to very high precision. It is to be understood that embodiments of the present invention have the very significant advantage that the measurements are made directly on the liquid itself, and do not rely on thermal equilibration of the liquid with the sensor (such as a thermocouple) or a body in thermal contact with the liquid, the temperature of which is measured such as the housing of the sensor in the case that infra-red (IR) measurement techniques are employed.

Fluid monitoring apparatus comprising a processing apparatus configured to:
  receive a sense signal from a capacitive fluid sensor comprising a first electrode and a second electrode with a sensing region between the electrodes;
  receive an alternating drive signal applied to the capacitive fluid sensor;
  determine at least one property of the fluid based on a comparison of the sense signal and drive signal, the apparatus being configured to provide an output in dependence on at least one said at least one property.

The apparatus may be configured to apply the alternating drive signal to a capacitive fluid sensor.

The apparatus may be configured to determine a complex difference signal comprising an in-phase difference component between the drive signal and the sense signal and a quadrature difference component between the drive signal and the sense signal.

The apparatus may be configured to determine the at least one property at least in part based on the difference signal.

The apparatus may be configured to determine at least one of a capacitance quantity indicative of a capacitance of the capacitive fluid sensor and a conductivity quantity indicative of a conductivity of a fluid in the sensing region.

The capacitance quantity may be a value of capacitance (e.g. in units of Farads) or a quantity corresponding to the capacitance, for example a data value that may be converted to units of Farads by means of a suitable conversion factor. Similarly, the conductivity quantity may be a value of conductivity (e.g. in units of mS/m) or a quantity corresponding to the conductivity, for example a data value that may be converted to units of mS/m by means of a suitable conversion factor.

The apparatus may be configured to determine a capacitance quantity indicative of a capacitance of the capacitive fluid sensor and to correct the capacitance quantity for at least one parasitic effect.

The apparatus may be configured to determine the conductivity quantity indicative of a conductivity of the fluid and to calculate a corrected capacitance quantity, being an expected value of capacitance quantity if the at least one parasitic effect were eliminated, based at least in part on the conductivity quantity.

Optionally, the apparatus is configured to calculate, by extrapolation, a corrected capacitance value based on the measured capacitance quantity and conductivity quantity and data in respect of a relationship between capacitance quantity and conductivity quantity, the corrected capacitance value corresponding to the expected value if the fluid was of substantially zero conductivity.

This feature has the advantage that, in the case that the fluid is an aqueous solution, compensation for the effects of electrode polarisation may be performed.

Optionally, the apparatus is configured to determine a dielectric constant quantity indicative of a dielectric constant of the fluid in the sensing region.

The dielectric constant quantity may be a value of dielectric constant or a quantity corresponding to the dielectric constant.

Optionally, the apparatus may be configured to calculate a temperature of the fluid in dependence on the dielectric constant quantity.

Temperature may for example be calculated by means of an equation equating temperature and dielectric constant.

Optionally, the apparatus may be configured to compare a value corresponding to at least one property of the fluid determined by the apparatus with a reference value of the at least one property of the fluid and to provide an output in dependence on the comparison.

The apparatus may for example perform the comparison by calculating a difference between the value determined by the apparatus and the reference value. The apparatus may provide the output in dependence on the difference.

Optionally, the apparatus may be further configured to calculate a current temperature of the fluid and to compare the at least one property of the fluid with a reference value of the at least one property of the fluid at the current temperature of the fluid.

The apparatus may for example employ an equation of look-up table (LUT) to determine the reference value of the at least one property (such as conductivity) at the current temperature. This may be particularly important in applications where a value of interested, such as dielectric constant, or conductivity, varies as a function of temperature, for examples in measurement so dielectric constant or conductivity of water, dilute aqueous solutions, or other liquids. In such cases it may be important to compare the measured value of dielectric constant of the fluid with a corresponding reference value of the fluid at the same temperature.

Optionally, the at least one property includes at least one selected from amongst a conductivity of the fluid and a dielectric constant of the fluid.

An aspect provides apparatus for measuring at least one property of a fluid, the apparatus comprising:
  a processing apparatus configured to:
    receive a sense signal from a capacitive fluid sensor comprising a first electrode and a second electrode with a sensing region between the electrodes;
    receive an alternating drive signal applied to the capacitive fluid sensor;
    determine a complex impedance of the fluid sensor based on the sense signal and the drive signal, the complex impedance comprising a quadrature component indicative of a capacitance quantity of the fluid sensor;
    determine a temperature of the fluid in dependence on at least the determined capacitance quantity of the fluid sensor.

The functionality described here can be implemented in hardware, software executed by a processing apparatus, or by a combination of hardware and software. The processing apparatus can comprise a computer, a processor, a state machine, a logic array or any other suitable processing apparatus. The processing apparatus can be a general-purpose processor which executes software to cause the general-purpose processor to perform the required tasks, or the processing apparatus can be dedicated to perform the required functions. Another aspect of the invention provides machine-readable instructions (software) which, when executed by a processor, perform any of the described methods. The machine-readable instructions may be stored on an electronic memory device, hard disk, optical disk or other machine-readable storage medium. The machine-readable medium can be a non-transitory machine-readable medium. The term "non-transitory machine-readable medium" comprises all machine-readable media except for a transitory, propagating signal. The machine-readable instructions can be downloaded to the storage medium via a network connection.

Within the scope of this application it is envisaged that the various aspects, embodiments, examples and alternatives, and in particular the individual features thereof, set out in the preceding paragraphs, in the claims and/or in the following description and drawings, may be taken independently or in any combination. For example features described in connection with one embodiment are applicable to all embodiments, unless such features are incompatible.

For the avoidance of doubt, it is to be understood that features described with respect to one aspect of the invention may be included within any other aspect of the invention, alone or in appropriate combination with one or more other features.

BRIEF DESCRIPTION OF THE DRAWINGS

One or more embodiments of the invention will now be described, by way of example only, with reference to the accompanying figures in which:

FIG. 21 is a flow diagram of a process according to an embodiment of the present invention;

FIG. 24 is a flow diagram of a process according to an embodiment of the present invention;

DETAILED DESCRIPTION

Figure 1:
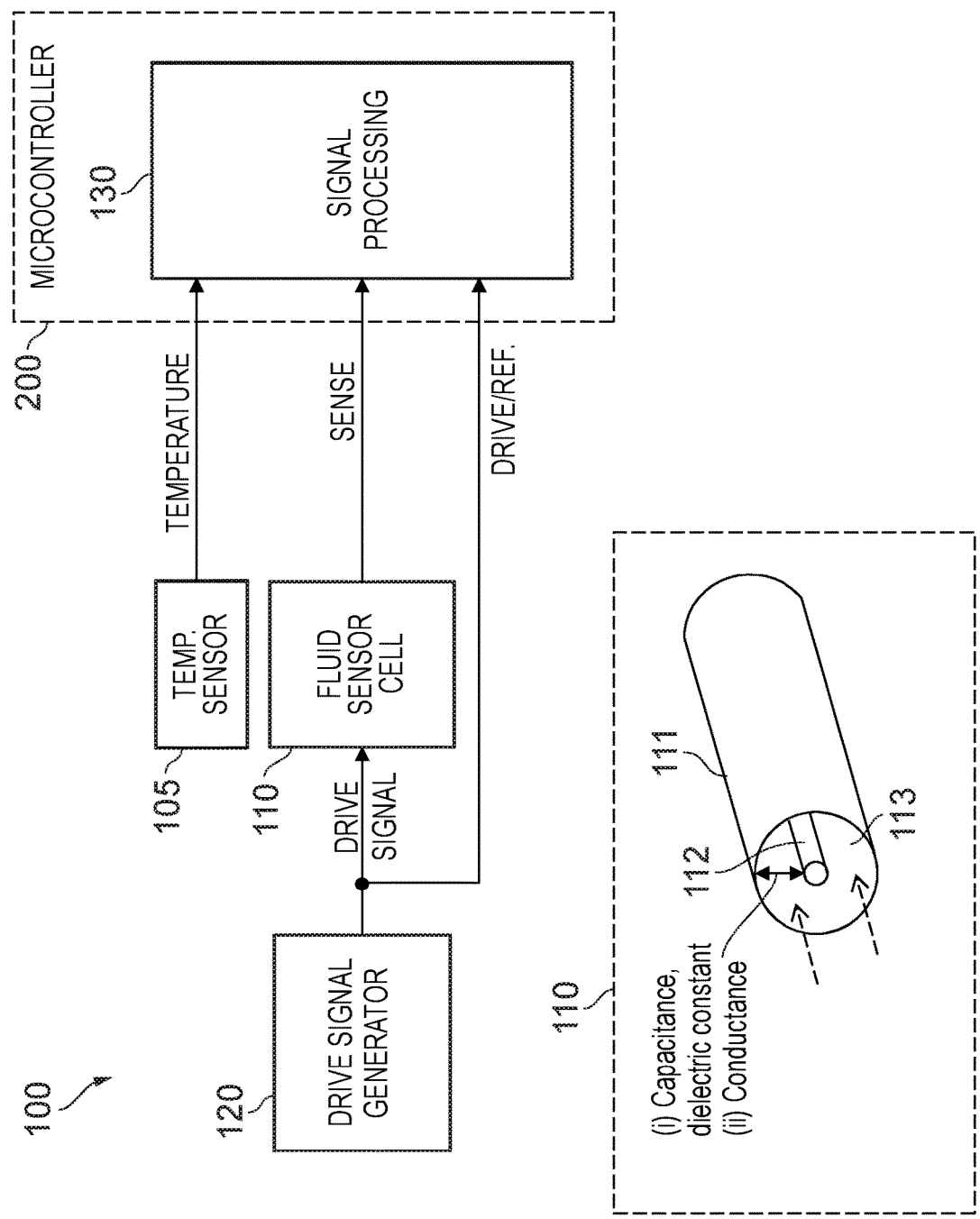
FIG. 1 shows a system for monitoring a fluid.

FIG. 1 shows a system 100 for monitoring a fluid, such as a liquid or a gas. The system 100 comprises a fluid sensor cell 110. FIG. 1 shows an example of a fluid sensor cell 110 which is configured for monitoring a flowing fluid. The fluid sensor cell 110 is a form of capacitive sensor. The sensor has a first, outer, electrode 111 and a second, inner, electrode 112. The outer electrode 111 is tubular. The inner electrode 112 is a cylindrical rod. The electrodes 111, 112 are coaxial. A fluid flow channel 113 is defined in the region between the electrodes 111, 112. Fluid can flow along the fluid flow channel 113. This allows measurements to be made without a need to interrupt a process which uses the fluid. For example, in the application of measuring a cutting fluid, the cutting fluid (or a portion of the cutting fluid) can be routed via the flow channel 113. The sensor cell 110 may have a different configuration. For example, a spaced-apart pair of linear electrodes (rods, plates or other shape). In a case of monitoring a static fluid, the sensor cell 110 does not have to include a flow channel.

The capacitive sensor 110 has two main properties: (i) capacitance; (ii) conductance. These properties will vary according to the type of fluid between the electrodes 111, 112. Capacitance of the sensor is the ability of the sensor to store electric charge. Capacitance varies according to the permittivity of the dielectric material between the electrodes 111, 112 of the capacitor. A dielectric material with a high dielectric constant (i.e. a good insulator) will increase the capacitance. Conductance is the flow of charge between the electrodes, through the dielectric material between the electrodes 111, 112. Conductance also depends on the properties of the dielectric material between the electrodes 111, 112 of the capacitor. A high impedance fluid will cause a small conductance between the electrodes 111, 112. A low impedance fluid will give a higher conductance between the electrodes 111, 112. For each of these properties, the dielectric material is the fluid between the electrodes 111, 112.

A drive signal generator 120 generates a drive signal. The drive signal is an alternating current electrical signal at a suitable frequency. The drive signal is applied to the fluid sensor cell 110. The drive signal may be applied to the inner electrode 112, with the outer electrode 111 connected to a reference ground. In an example of the present application the alternating current electrical signal has a frequency which is in the low radio frequency (RF) range, of less than 10 MHz, such as 5.05 MHz. The drive signal generator 120 can be implemented by a Direct Digital Synthesis integrated circuit feeding a wideband operational amplifier. Direct Digital Synthesis is a technique which generates a sinusoidal analogue signal using a sequence of digital values representing amplitude of the signal at points in time. The digital values are converted into an analogue signal by a digital-to-analogue converter. The digital values required to generate the signal may be stored, and retrieved from memory, or calculated on-the-fly using an algorithm.

A signal processing stage 130 is implemented, for example, by a microcontroller 200. The signal processing stage 130 receives an alternating electrical signal SENSE from the fluid sensor cell 110. The drive signal applied to the fluid sensor cell 110 will be modified by properties of the fluid in the fluid sensor cell 110. SENSE is indicative of the fluid. The signal processing stage 130 also receives the drive signal as a signal DRIVE or REF. It is possible to supply the drive signal by directly connecting an output of the drive signal generator 120 to the processing stage 130. Alternatively, the drive signal may be tapped from a different point, REF, in the system as described below.

Figure 2:
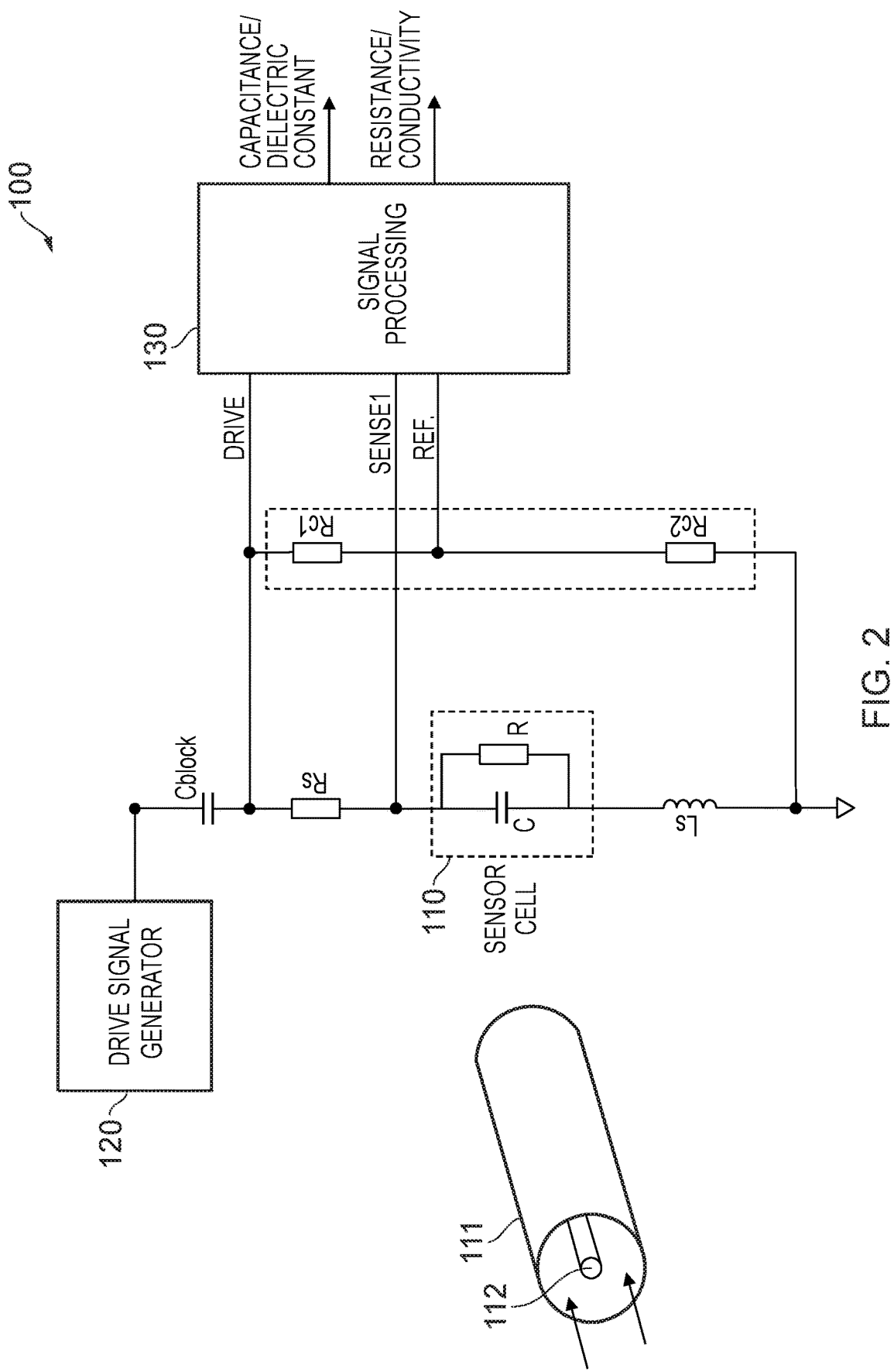
FIG. 2 shows a front-end of the system, showing analogue components.

FIG. 2 shows a schematic of the front-end of the system 100, showing analogue-domain components. The sensor cell 110 can be represented as an equivalent circuit network with a capacitance C in parallel with a resistance R. The value of C in this network is determined by the dielectric constant and R is a function of the conductivity of the fluid. $C_{block}$ is a DC blocking capacitor. $C_{block}$ is large (>10 nF) compared to the capacitance of the sensor cell 110 to ensure there is no DC bias on the fluid. A DC bias can cause unwanted electrolytic plating of the electrodes 111, 112.

The impedance of the sensor cell 110 equivalent circuit (R and C in parallel) can be expressed as:

$$Z = \left[\frac{1}{R} + j\omega C\right]^{-1}$$

where ω is 2π×the drive signal frequency.

$R_s$ and Z form a potential divider and the voltage across Z is the main sensor feedback signal SENSE. Z is a complex impedance. $L_s$ is lead inductance from the connections to the sensor cell 110. $L_s$ also contributes (significantly) to phase and amplitude of SENSE. $L_s$ is a parasitic element of the apparatus.

Figure 3A:
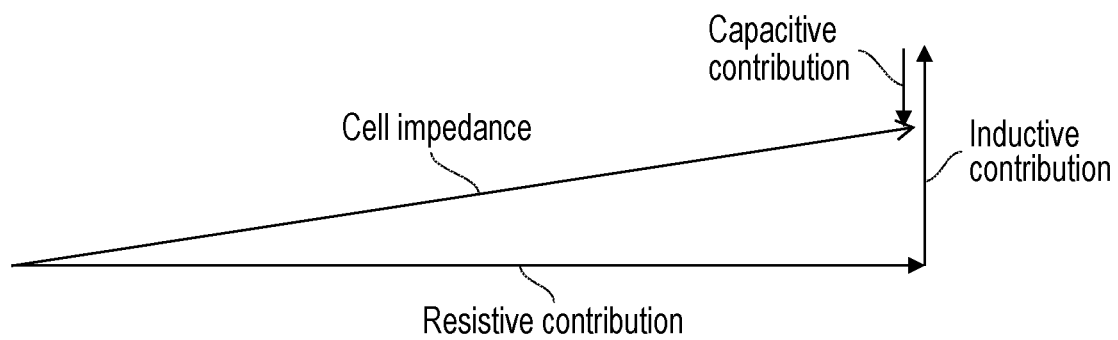
FIG. 3A shows impedance of the sensor cell and lead in the system of FIG. 1.
Figure 3B:
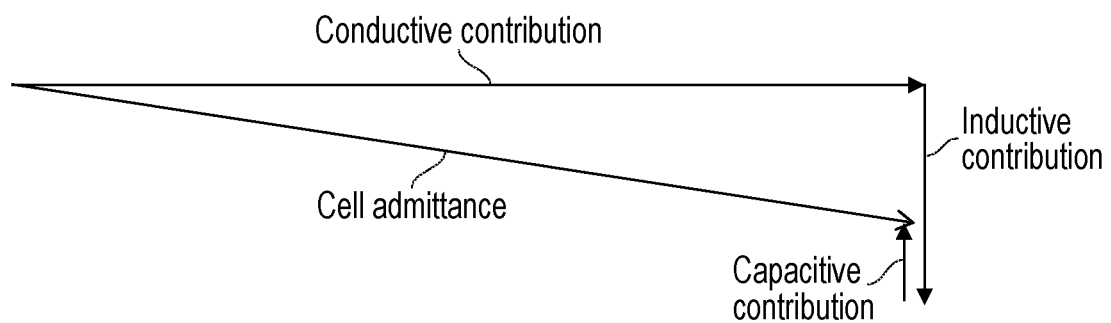
FIG. 3B shows admittance of the sensor cell and lead in the system of FIG. 1.

FIG. 3A shows a complex impedance of a combination of the sensor cell 110 and lead(s) when measuring fluids with high conductivities. This will be described in full detail below but, in summary, the complex impedance of the sensor cell 110 and lead has an in-phase/real component and a quadrature/imaginary component. The in-phase/real component is due to resistance of the sensor cell and lead. The quadrature/imaginary component is mainly due to capacitance of the sensor cell and inductance of the lead. FIG. 3B shows the corresponding complex admittance, where admittance is the reciprocal of the impedance, Y=1/Z. From FIG. 3A and FIG. 3B it can be seen that it is difficult to observe the contribution to the complex impedance made by the capacitive sensor cell C, which represents the fluid under test. The wanted capacitive contribution is masked by the unwanted parasitic inductive contribution. The main parasitic effects which need to be compensated for are lead inductance and input capacitance of the analogue-to-digital converter (ADC) used to measure the signals.

Figure 4:
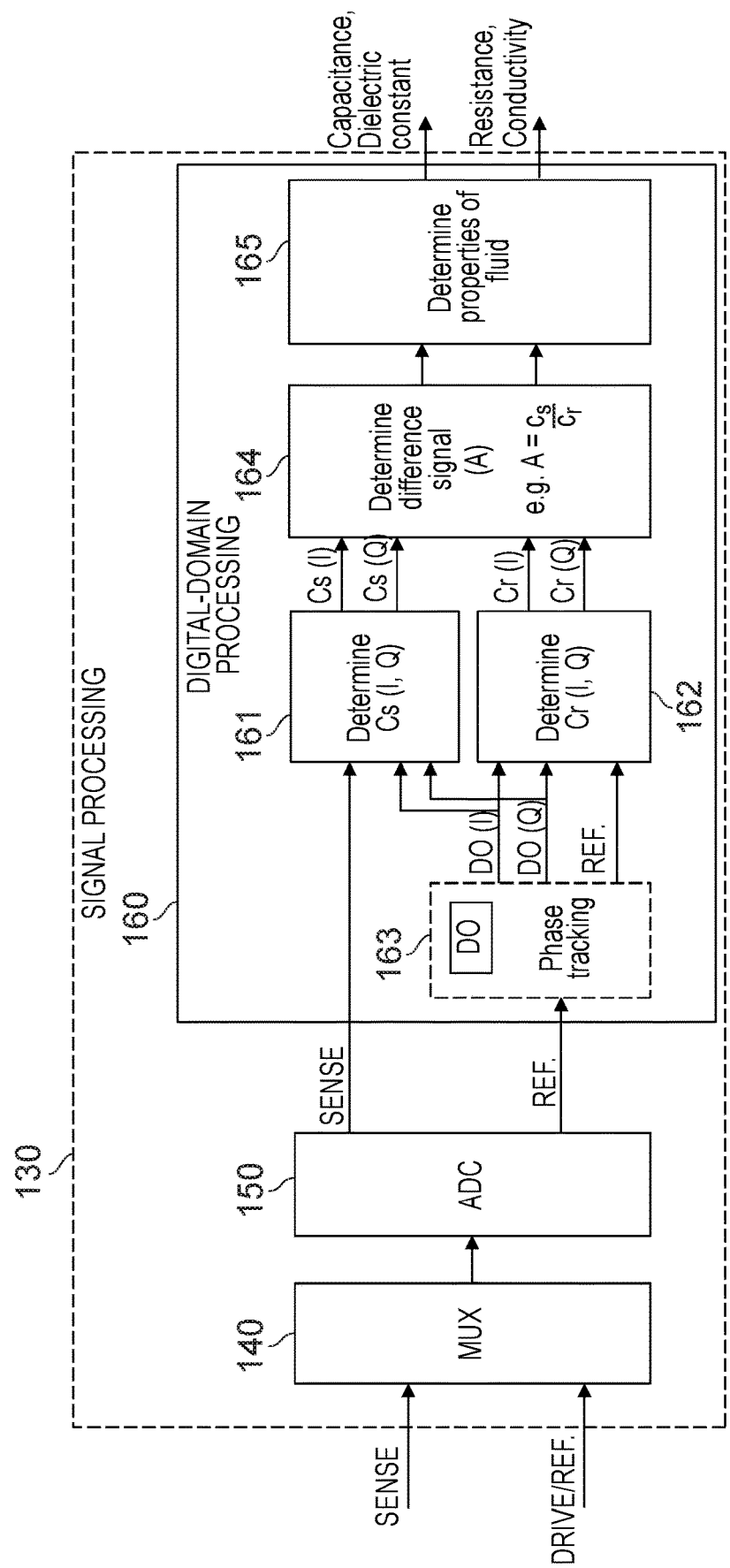
FIG. 4 shows signal processing in the system of FIG. 1.

FIG. 4 shows the signal processing stage 130. A multiplexer MUX 140 receives SENSE and DRIVE/REF as inputs and selectively outputs one of the input signals to an analogue-to-digital converter (ADC) 150. The ADC 150 outputs digital values. Outputs of the ADC 150 are applied to a digital-domain processing stage 160. A processing stage 161 determines in-phase (real) and quadrature (imaginary) components of the sense signal SENSE. These will be called Cs(I) and Cs(Q) respectively. A processing stage 162 determines in-phase (real) and quadrature (imaginary) components of the drive/reference signal. These will be called Cr(I) and Cr(Q) respectively. Processing stages 161, 162 perform Fourier analysis. Stage 163 includes a local digital oscillator, and acquires synchronisation between the local digital oscillator and the drive signal. Stage 163 outputs in-phase (I) and quadrature (Q) signals to stages 161 and 162. These outputs are labelled DO (I), DO (Q). A processing stage 164 determines in-phase (real) and quadrature (imaginary) components of a difference signal between the sense signal SENSE and the drive/reference signal. The difference signal represents a difference, in terms of amplitude and phase, between the drive signal applied to the sensor cell 110 and the signal across the sensor cell 110 due to the fluid. A processing stage 165 determines properties of the fluid. Stage 165 determines capacitance (dielectric constant) of the fluid using the I & Q values of the difference signal. Stage 165 can also determine resistance (conductivity) of the fluid using the I & Q values of the difference signal.

The output of stage 164 represents the measured impedance at the ADC 150, subject to a transformation caused by parasitic properties of the system. The output consists of two numbers corresponding to the real (in-phase, I) and imaginary (quadrature, Q) outputs of the Fourier analysis. There are several sources of parasitic properties of the system. Lead inductance $L_s$ (FIG. 2) is present as a property of wires connecting to the sensor. It has the effect of introducing an imaginary component which is a function of both frequency and conductivity. Its contribution to the imaginary components of the measurements is larger than the changes in capacitance (due to fluid) that are being measured. The ADC 150 has parasitic input capacitance that also causes a finite phase shift. The phase shift caused by the ADC will be a function of the output impedance of SENSE.

Figure 5:
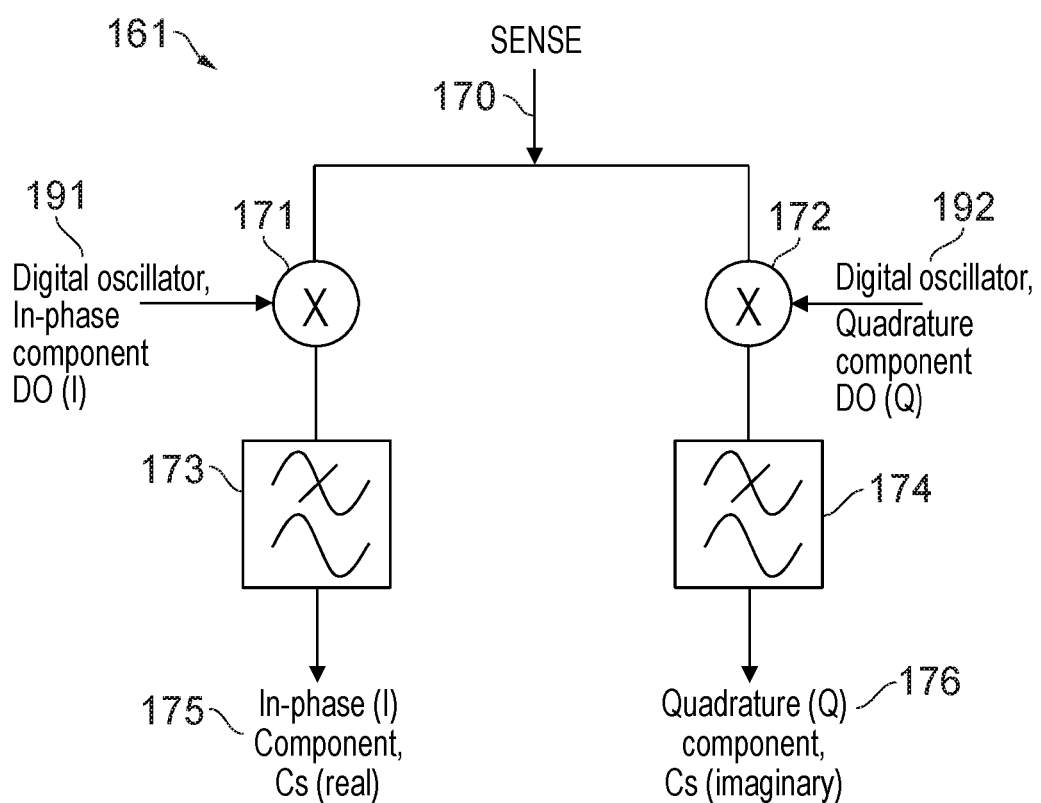
FIG. 5 shows a signal processing stage for the sensed signal.

FIG. 5 shows stage 161 of the digital-domain processing 160 in more detail. Samples of the digitised signal SENSE are received at an input 170. The processing proceeds in two arms: an in-phase arm and a quadrature arm. In the in-phase arm, SENSE is multiplied 171 with an in-phase (I) output of a digital oscillator, DO (I). An output of the multiplication is applied to a low-pass filter 173. An output 175 of the low-pass filter 173 provides an in-phase (I) component of the signal SENSE relative to the digital oscillator 181, called Cs(I). In the quadrature arm, SENSE is multiplied 172 with a quadrature (Q) component of a digital oscillator, DO (Q). An output of the multiplication is applied to a low-pass filter 174. An output 176 of the low-pass filter 174 provides a quadrature (Q) component of the signal SENSE relative to the digital oscillator 181, called Cs(Q). Each of the low-pass filters 173, 174 may be implemented as an Infinite Impulse Response (IIR) digital filter. Each of the low-pass filters 173, 174 has a time-averaging function on sample values applied to an input of the filter. As an example, the filter can perform a 'rolling' average on input values. Consider that the filter has an input x and an output x0. At each computation cycle:

$$x0=(previous\ x0)*0.999+0.001*x$$

In this simple example, the filter coefficient values are 0.999 and 0.001, with the two coefficients summing to 1. It will be understood that the digital filter can perform a different algorithm with different coefficient values and/or a higher number of computation stages. The low-pass filters 173, 174 can make it possible to determine a value of the I or Q component with a high degree of accuracy, by computing a value over a significant number of computations. For example, the output value of the filter may be computed over several thousand cycles of the drive signal SENSE. Stage 161 allows the circuit to tune in to the input signal within a very narrow frequency band and produces two output results representing the size of the in-phase (real) and quadrature (imaginary) components of the input signal. Reducing the bandwidth gives very accurate sub-quantisation level resolution.

Referring back to the example system of FIG. 1, the microcontroller 200 and the drive signal generator 120 can be implemented as separate integrated circuits. This means the drive signal generator 120 and the microcontroller 200 will each have a separate local oscillator (clock) which operates at a different rate and/or accuracy. This also means that the drive signal is asynchronous to the signal processing 130. The amplitude and phase of DRIVE is initially treated as unknown by the signal processing 130.

It is to be understood that the ADC 150 may be provided on one or more chips that are separate from the microcontroller 200 and which communicate digitally with the microcontroller 200. Alternatively, the ADC 150 may be provided in the same integrated circuit package as the microcontroller 200.

Figure 6:
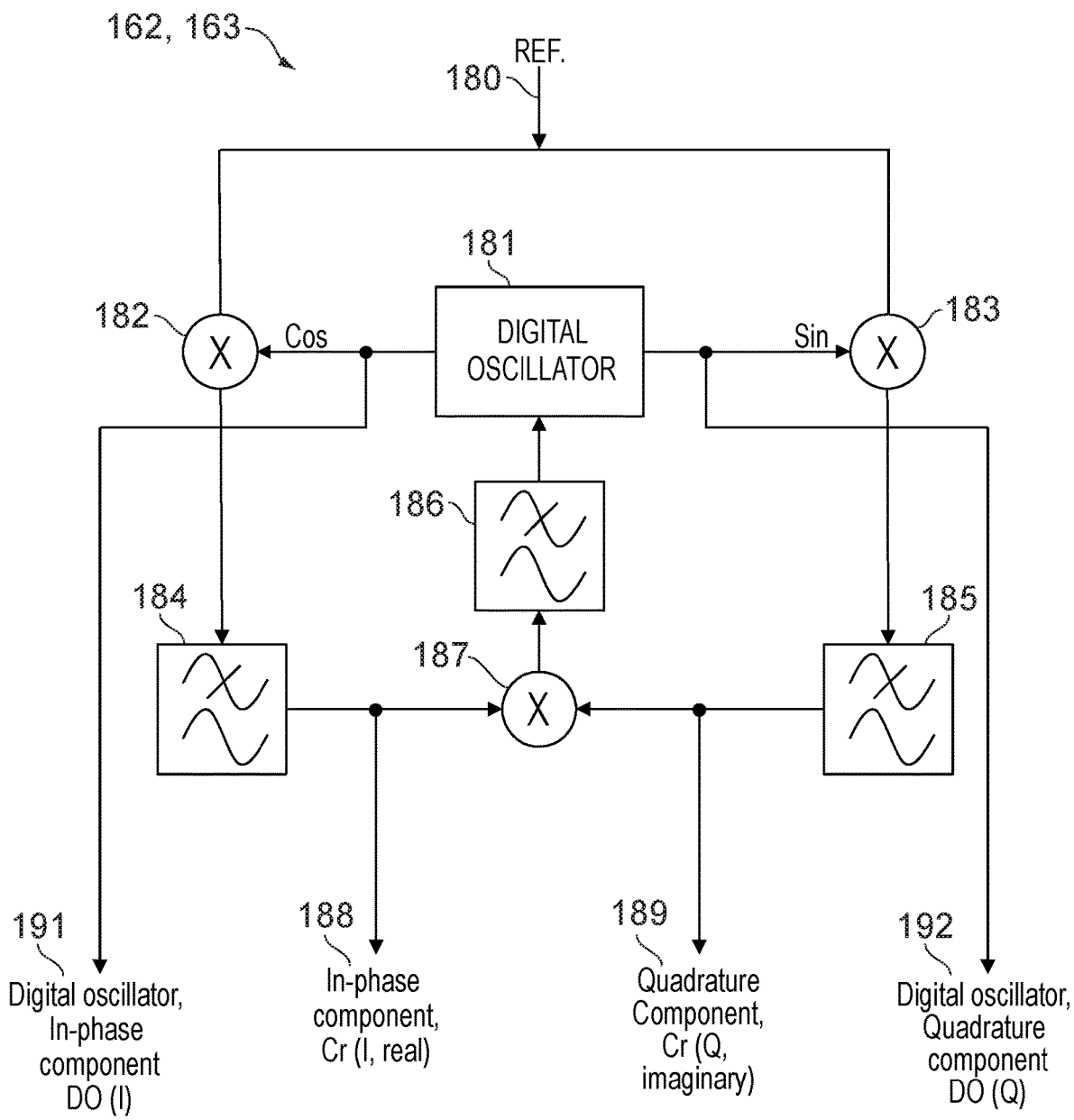
FIG. 6 shows a signal processing stage for the reference signal, and for synchronisation.

FIG. 4 and FIG. 6 show an additional stage 163 which can synchronise to REF. Referring to FIG. 6, the circuit 163 is a Costas loop. A Costas loop is a form of phase-locked loop which can digitally lock onto the drive signal (DRIVE or REF). An input 180 receives signal DRIVE representing the drive signal. A digital oscillator 181 outputs two data streams representing two sine waves: one in phase (Cos) and one in quadrature (Sin) to the drive signal. Each signal is multiplied 182, 183 with REF. Outputs of the multiplication are low-pass filtered 184, 185. Respective outputs of each low-pass filter 184, 185 are multiplied together 187 and applied to a low-pass filter 186. An output of low-pass filter 186 is applied as a control signal to the oscillator 181. The circuit of FIG. 6 performs two functions: (i) it achieves synchronisation between the digital oscillator and drive/reference signal REF; (ii) it determines in-phase component and a quadrature component of the drive/reference signal REF relative to the digital oscillator 181.

Multiplying both real and imaginary parts of the digital oscillator signal with the incoming drive signal REF and integrating over a number of samples yields the real and imaginary Fourier coefficients of the drive signal at that frequency. If the drive signal is in-phase and of equal frequency (i.e. a lock condition) then the real Fourier coefficient should be 0.5 and the imaginary coefficient should be 0. In practice, there is usually a difference between the signals, such as the drive signal leading or lagging the digital oscillator. It is possible to determine whether the drive/reference signal REF is leading or lagging the digital oscillator by looking at the value of the imaginary part. An appropriate correction is applied to the digital oscillator 181 (i.e. advancing or retarding the digital oscillator 181) until a lock condition is achieved. So, the digital oscillator 181 tracks the incoming drive/reference signal REF and automatically makes adjustments due to clock drift. Once locked, the same control loop maintains a locked condition. Outputs 191, 192 of the digital oscillator 181 are used as the DO (I) and DO (Q) inputs to the processing stage 161. An output of the low-pass filter 184 provides an in-phase component of drive/reference signal REF relative to the digital oscillator 181, called Cr (I). An output of the low-pass filter 185 provides a quadrature component of drive/reference signal REF relative to the digital oscillator 181, called Cr (Q).

Figure 7:
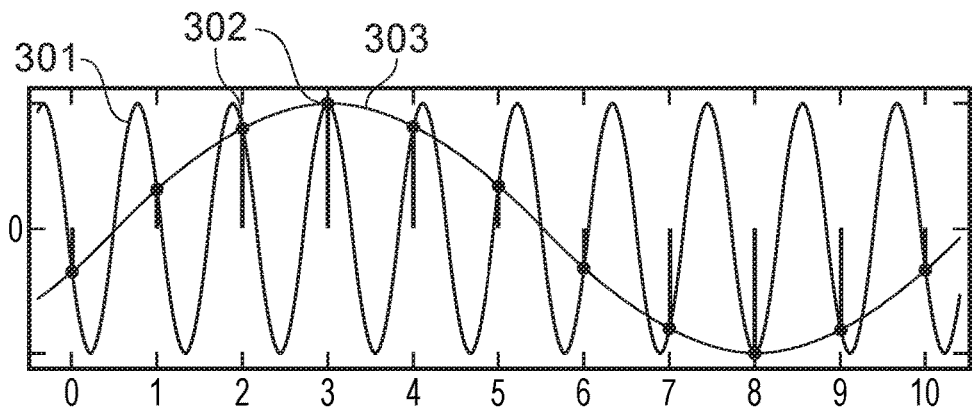
FIG. 7 shows analogue-to-digital sampling.

FIG. 7 shows operation of the ADC 150. In an example of the present invention, the ADC operates at a sampling frequency which is lower than a frequency of the drive/reference signal REF, and therefore lower than a frequency of the signal SENSE received from the sensor cell. FIG. 7 shows signal SENSE 301 and sampling points 302. The resulting signal, after sampling, has a frequency which is a difference between the input signal and the sampling frequency. For example, if the signal 301 has a frequency of 1.05 MHz and the sampling frequency is 1.0 MHz, the sampled signal has a frequency of 50 kHz. Conventional sampling theory recommends a sampling frequency which is at least twice the highest frequency in the sampled signal to avoid aliasing. In the illustrated example, aliasing occurs, as the signal in the sampled/converted data will appear as a much lower sine wave. However, the phase and amplitude of the original signal is preserved in the sampled signal and corresponds to the phase and amplitude of the drive signal. By using an output signal which has a lower frequency than the original signal (e.g. 50 kHz compared to 1.05 MHz) it is possible to process the signal in the digital domain using less computational resources.

Three alternative ways of digital-domain processing will now be described. In a first method, a mathematical model of the apparatus is used to directly calculate values of capacitance (dielectric constant) and resistance (conductivity) from the measured in-phase and quadrature values of the difference signal. In a second method, the measured in-phase and quadrature values of the difference signal are applied to a look-up table to obtain output values of capacitance (dielectric constant) and resistance (conductivity). In a third method, measured in-phase and quadrature values are mapped to a stored set of curves representing capacitance (dielectric constant) and resistance (conductivity). A best fit between the measured I, Q values and one of the curves represents the capacitance (dielectric constant) and resistance (conductivity).

Each of the methods can use the same initial stages of signal processing. The signal processing stages 161, 162 output values representing two complex numbers:
- $c_s$ representing the phase and magnitude of the sense signal, SENSE. $c_s$ comprises an in-phase (real) component $c_s$ (I) and a quadrature (imaginary) component $c_s$ (Q).
- $c_r$ representing the phase and magnitude of the reference signal (i.e. the drive signal, DRIVE/REF). $c_r$ comprises an in-phase (real) component $c_r$ (I) and a quadrature (imaginary) component $c_r$ (Q).

Dividing the two complex measurements [$c_s/c_r$] gives a quantity which is independent of supply voltage or ADC reference voltage variation. Performing this operation also has an effect that if the digital oscillator 181 lags or leads the drive signal by even a small amount, resulting phase shifts are eliminated. This is because the error would apply equally to both drive and sense signals, i.e. a common mode error.

Processing stage 164 determines the difference signal. Performing the division [$c_s/c_r$] gives:
(i) the phase difference between the sense signal and the drive/reference signal;
(ii) a magnitude equal to a ratio of the magnitudes of the sense signal and the drive/reference signal.

It should also be noted that the apparatus shown in FIG. 4 with a single ADC 150 and a multiplexer 140 means that the sense and reference signals are not sampled simultaneously. Therefore, it is necessary to multiply the ratio $c_s/c_r$ by another complex quantity to correct for this phase misalignment:

$$c_p = e^{i\omega T}$$

where:
- the angular frequency of the drive signal $\omega = 2\pi * 5{,}050{,}000$ Hz;
- the sampling frequency=2 MHz and the time between sampling channels T=0.5 µs.

The 'output' of the sensor is now a complex quantity A calculated thus:

$$A = \frac{c_p \cdot c_s}{c_r}$$

A is the value that is used in all further analysis.

The following section provides detail of the mathematical model of the apparatus.

Model-Based Method

Input Impedance and Parasitic Properties of the ADC

The input impedance of the ADC 150 will modify the input signal both in amplitude and phase and so its effects need to be calibrated out. The input impedance of the ADC channels is treated as unknown, but it is possible to assume that they are approximately equal since the same ADC is used for measuring both channels, and the inputs are multiplexed.

Figure 8:
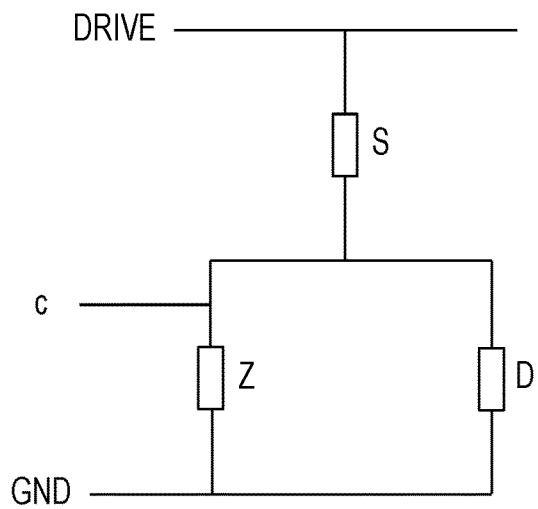
FIG. 8 and FIG. 9 show impedances in the system.

The input impedance of the ADC 150 can be deduced from a process called 'bare-board' calibration. The PCB alone (i.e. the sensor cell is not connected) is powered up and the open-circuit signal measured can be analysed. FIG. 8 shows how the impedances combine generally for both channels, where:
- Z is the input impedance of the ADC;
- S is a 200 ohm resistor ($R_S = R_{c1}$);
- D is a load (to be measured) connected in parallel to the ADC.

Without the cell connected, $D \to \infty$ for the sense channel $c_s$, and $D = R_{c2}$ for the reference channel $c_r$. As an example, D=220 resistor for a cell filled with cutting fluid. This makes the drive/ref signal and sensor cell have roughly the same impedance when presented to the ADC. It will be understood that D can be set to a value appropriate to the application.

It can be assumed that Z is the same for both channels, and raw sensor output value A can deduce the value of Z.

Network analysis of the above gives:

$$c = \frac{[Z^{-1} + D^{-1}]^{-1}}{[Z^{-1} + D^{-1}]^{-1} + S}$$

which simplifies to:

$$c = \frac{1}{1 + SZ^{-1} + SD^{-1}}$$

Now turn this general form into an expression for $c_s$ and $c_r$:

$$c_s = \frac{1}{1 + SZ^{-1}}$$

since $D \to \infty$ and $$c_r = \frac{1}{1 + SZ^{-1} + SD^{-1}}$$

After rearranging and simplification, $c_s/c_r$ can be written as:

$$A = \frac{c_s}{c_r} = \frac{Z + S + ZSD^{-1}}{Z + S}$$

and solved for Z.

$$Z = \frac{S(1 - A)}{A - 1 - SD^{-1}}$$

The value of Z is calculated from the bare-board measurement for each sensor and stored in non-volatile memory for use with all further calculations. This complex quantity represents both the resistive and capacitive loads at the operating frequency.

Deducing the Cell Impedance

Now that the ADC impedance is fully characterised, it is then possible to deduce the impedance of the connected sensor load from further network analysis. The cell impedance is denoted by L. During operation, with the sensor cell connected, the sensor channel output can be written (analogously to our expression for $c_r$) as:

$$c_s = \frac{1}{1 + SZ^{-1} + SL^{-1}}$$

Using the previously derived expression for $c_r$ we can state that:

$$A = \frac{c_s}{c_r} = \frac{1 + SZ^{-1} + SD^{-1}}{1 + SZ^{-1} + SL^{-1}}$$

This can be solved for L to give:

$$L^{-1} = \frac{1}{AS} + \frac{Z^{-1}}{A} + \frac{D^{-1}}{A} - \frac{1}{S} - Z^{-1}$$

This expression combines all of the known resistor values and the calibration value for ADC impedance to give the impedance of the cell and parasitic properties associated with connections to it.

Figure 9:
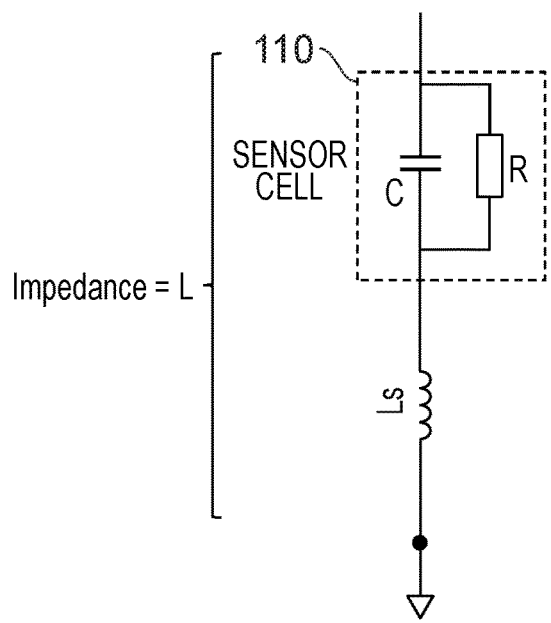

It is assumed now that L represents the impedance of the network shown in FIG. 9 comprising the sensor cell 110 and the lead inductance $L_s$. The contribution of lead inductance $L_s$ is very significant, but it is assumed that its value is constant and it can be determined empirically.

$$L = i\omega L_s + \frac{1}{R^{-1} + i\omega C}$$

Where R is the resistance of the cell and C is its capacitance. R and C can both be deduced from this equation when the value of $L_s$ is known. This is most easily achieved by calculating the cell admittance:

$$Y = \frac{1}{L - i\omega L_s} = R^{-1} + i\omega C$$

$$C = \frac{\text{Im}(Y)}{\omega} \text{ from the imaginary part of the admittance, and:}$$

$$R = \frac{1}{\text{Re}(Y)} \text{ from the real part.}$$

Calculating Conductivity and Relative Permittivity

The resistance of the cell is determined theoretically by the cell geometry and the resistivity of the fluid as follows:

$$R = \rho \cdot \frac{\ln(b/a)}{2\pi L}$$

where:
$\rho$ is the resistivity of the fluid;
b is the internal diameter of the outer pipe of the cell (e.g. $26.9 \times 10^{-3}$ m);
a is the external diameter of the co-axial rod (e.g. $7 \times 10^{-3}$ m);
L is the length of the rod exposed to the fluid (e.g. $75 \times 10^{-3}$ m).

The cell factor is the ratio of resistance to resistivity. This is calculated to be around 2.85, and measured to be around 2.76 from lab testing with saline fluids of known concentrations.

Conductivity=1/$\rho$.

Therefore:

Conductivity=2.76/R (Equation 1)

The capacitance of the cell is calculated to be:

$$C = \frac{2\pi L}{\ln(b/a)} \epsilon_0 \epsilon_r$$

where $\epsilon_0$ is the dielectric permittivity of free space and $\epsilon_r$ is the relative permittivity (dielectric constant) of the fluid.

All of the other dimensions are the same. Hence the experimentally determined cell factor of 2.76 can also be used to develop the relationship between $\epsilon_r$ and capacitance in a similar way such that:

$\epsilon_r = 2.76 \, C/\epsilon_0$ (Equation 2)

From the above description, it will be understood that the measured values $c_s$, $c_r$ (converted to the complex difference signal quantity A) are input to a mathematical model of the apparatus which includes at least one parasitic component, to provide an output value of conductivity (Equation 1) and dielectric constant (Equation 2). Another possible property is complex permittivity.

Determination of Lead Inductance and Other Parasitic Elements

The lead inductance can be determined empirically. If the expression for L is rewritten using discrete real and imaginary parts, it can be seen that the contribution of $L_s$ to the final measurement is small when cell resistance is high, and plays a significant part when the cell resistance is low. By passing de-ionised water through the cell, it is possible to measure a value for the cell capacitance by assuming lead-inductance to be zero in the above analysis.

Passing saline solutions of varying concentrations through the sensor at a constant temperature should give a constant value for capacitance and varying values of conductivity. A value of lead inductance was chosen to give the flattest possible response for capacitance over this range.

However, the response is not perfect, as it is likely that there are additional parasitic components yet to be identified and the network analysis needs further refinement.

Figure 10:
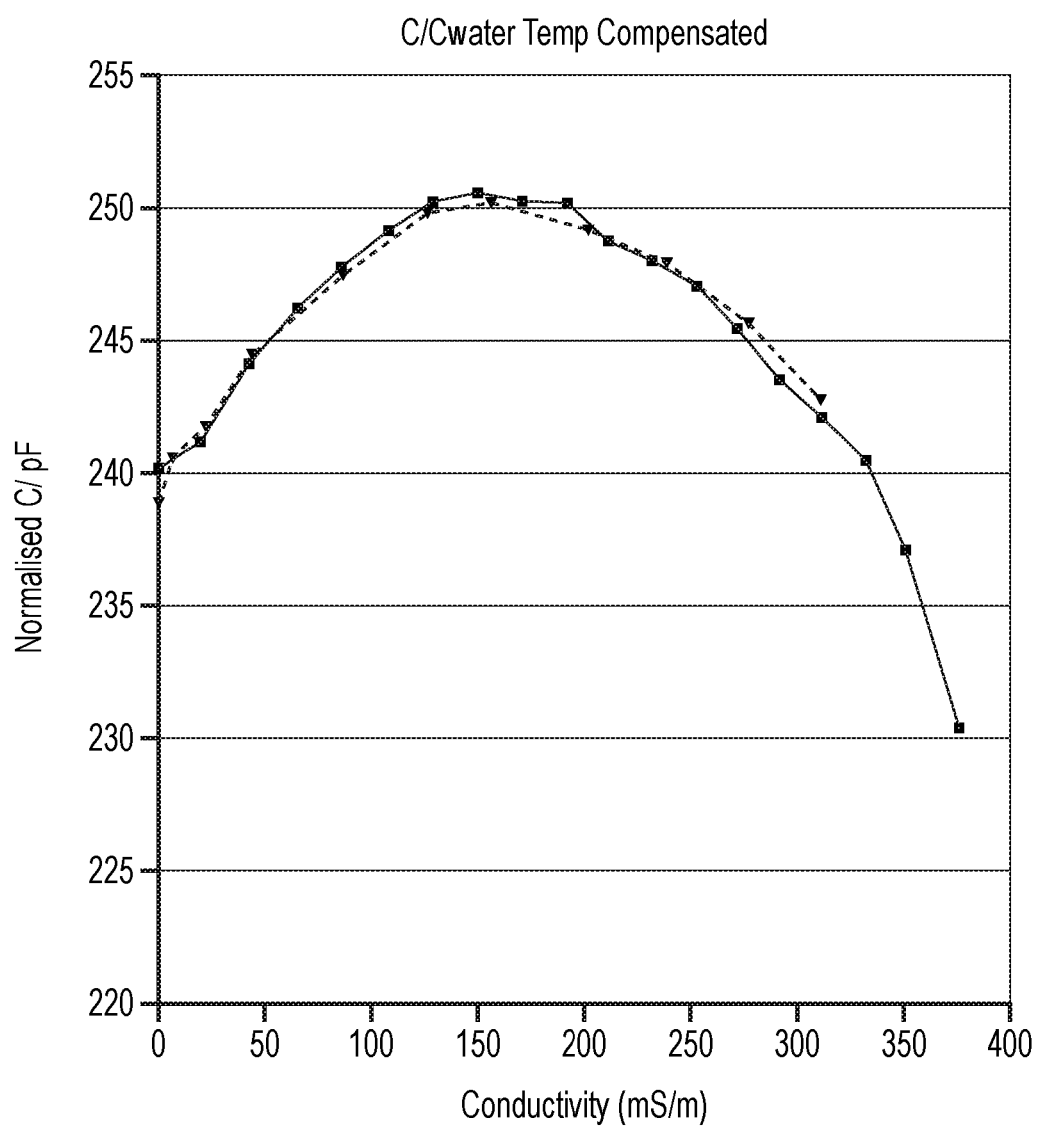
FIG. 10 shows a graph of capacitance versus conductivity for a test fluid.

FIG. 10 shows two sets of measurements performed on varying concentrations of saline. It can be seen that there are deviations from the ideal flat horizontal line even when lead inductance is considered. Therefore, for practical applications, it is possible to store a map of this saline data and interpolate these values to provide calibration information for different conductivities.

Look-Up Table Method

The look-up table method uses the difference signal determined by stage 164. As described above, the quantity A can be used:

$$A = \frac{c_p \cdot c_s}{c_r}$$

where:
$c_s$ represents the phase and magnitude of the sense signal, SENSE. $c_s$ comprises an in-phase (real) component $c_s$ (I) and a quadrature (imaginary) component $c_s$ (Q).
$c_r$ represents the phase and magnitude of the reference signal (i.e. the drive signal, DRIVE/REF). $c_r$ comprises an in-phase (real) component $c_r$ (I) and a quadrature (imaginary) component $c_r$ (Q).
$c_p$ is a correction factor to compensate for the different times at which $c_s$ and $c_r$ are sampled.

Processing stage 165 then uses the in-phase and quadrature components of the complex difference signal quantity A to look up corresponding values of C (dielectric constant) and R (conductivity) in a stored set of data, i.e. a look-up table.

Data Mapping Method

The data mapping method uses the difference signal determined by stage 164. As described above, the quantity A can be used:

$$A = \frac{c_p \cdot c_s}{c_r}$$

where:
- $c_s$ represents the phase and magnitude of the sense signal, SENSE. $c_s$ comprises an in-phase (real) component $c_s$ (I) and a quadrature (imaginary) component $c_s$ (Q).
- $c_r$ represents the phase and magnitude of the reference signal (i.e. the drive signal, DRIVE/REF). $c_r$ comprises an in-phase (real) component $c_r$ (I) and a quadrature (imaginary) component $c_r$ (Q).
- $c_p$ is a correction factor to compensate for the different times at which $c_s$ and $c_r$ are sampled.

Figure 11:
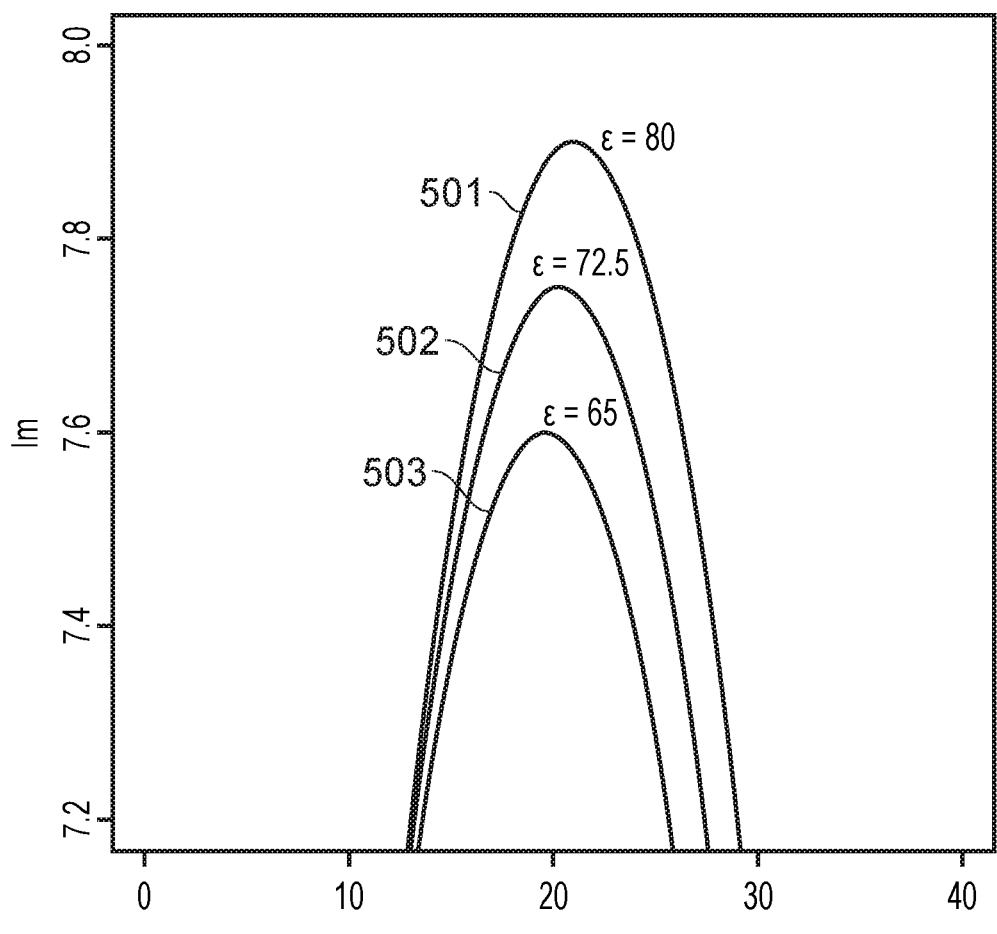
FIG. 11 shows a set of curves which can be used to map in-phase and quadrature components to dielectric constant and conductivity.

Processing stage 165 then maps the in-phase and quadrature components of the complex difference signal quantity A to (or compares it to) a stored set of data. The stored data may be in the form of a set of curves. FIG. 11 shows a set of curves 501, 502, 503 representing fluids of three different dielectric constants and varying conductivity. All values are approximate and are to represent the concept only. A 'measurement' in the form of a pair of values I, Q will be represented by a point on this map of data. To deduce the emulsion concentration therefore it is possible to empirically deduce concentration and dielectric constant from the position of a point on this map. For a given measurement (I, Q) it is possible by extrapolation to work out the dielectric constant to within enough precision for monitoring emulsion cutting fluid concentration with varying amounts of ionic contamination.

Figure 12:
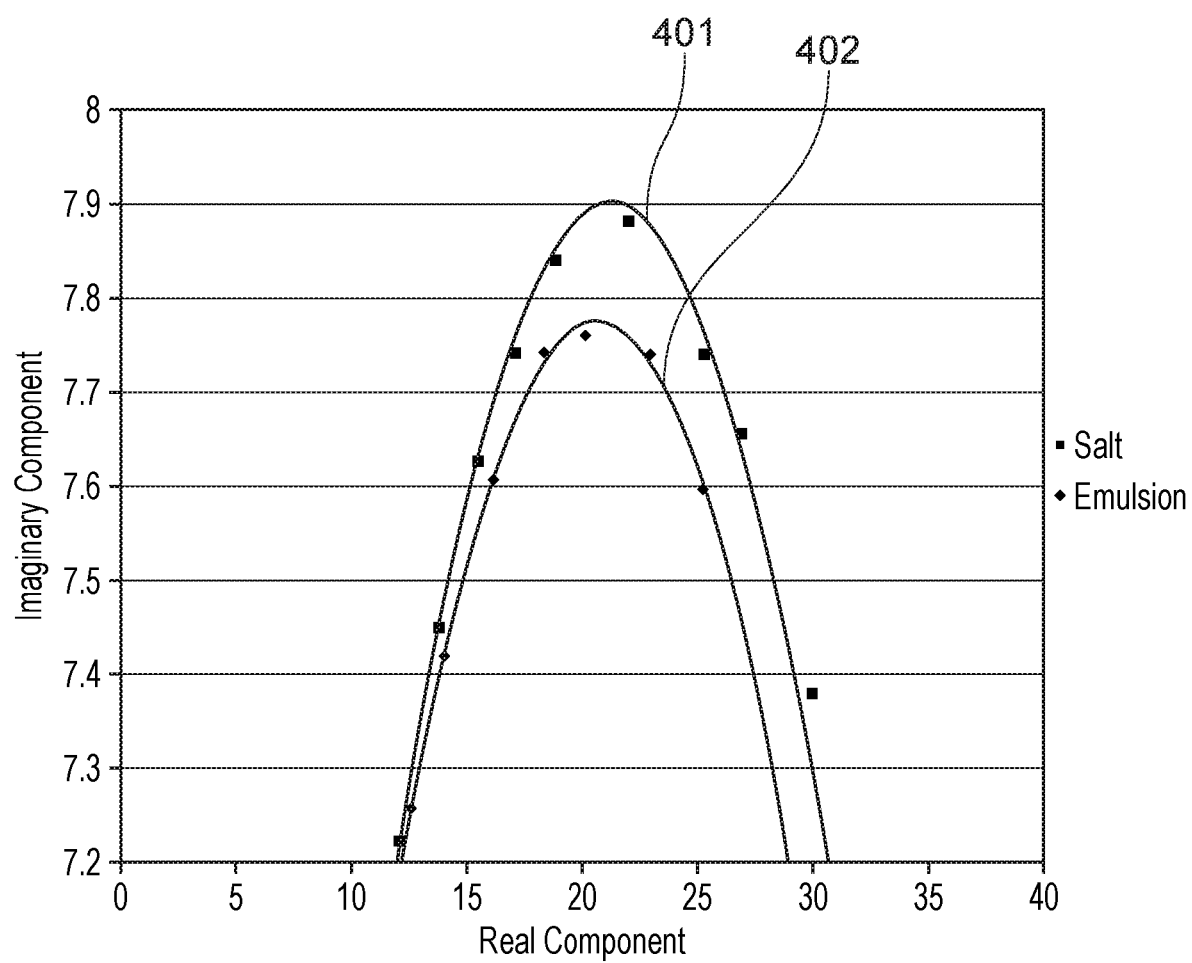
FIG. 12 shows data to illustrate in-phase and quadrature components vary with fluid properties.

FIG. 12 shows experimental data from measurements at 5.05 MHz at 20 degrees Celcius of various solutions of brine (dielectric constant assumed to be unchanged) 401 and emulsion (with varying conductivity and dielectric constant) 402. The data illustrates the transformation effect of the parasitic circuit elements. Curve 401 represents a fluid which has unchanging dielectric constant, but varying conductivity. This curve can be considered as a type of control which shows how the parasitic effects 'warp' the mapping of the real and imaginary components away from a perfect theoretical straight horizontal line. Curve 402 represents fluids with both variations in dielectric constant and conductivity. A test fluid was formed by adding varying amounts of cutting fluid emulsion mixture to deionised water. In this case, the emulsion concentration is varied between 2.5 and 20%. The conductivity is seen to increase with increasing concentration (right to left), but also the dielectric constant is reduced from an expected value of ~77.5 at 2.5% to ~60 at 20%.

The convergence of the data on the left hand side is due to the mathematical effect of increasing conductivity causing a reduction of the sensitivity of the system to the effects being measured.

Accurate Conductivity Measurements

Using a drive signal of 1.05 MHz or lower, the reactive (capacitive and parasitic components) of the signal are significantly reduced. Under these conditions the real part of the signal can be used to deduce conductivity without making assumptions about the parasitic effects of the circuit. For a system where it is not expected that temperature or fluid composition changes quickly, this measurement can be made near simultaneously to the high frequency measurement.

Reference Signal (REF)

A refinement of the design is the use of a reference signal REF. This design uses Rc1 and Rc2 to represent a 'virtual' purely resistive cell. It will have an amplitude in phase with the drive signal. REF can provide a better reference signal than DRIVE, as it is designed to have a similar output impedance to SENSE. The thinking behind this is that if the phase shift caused by the ADC input capacitance was identical for each channel, its effect would cancel out. This ideal situation is unlikely to be achieved, but this approach will help to reduce the effect of the input capacitance.

Example Fluids

An example application of the apparatus is to control the mixture and composition of emulsion cutting fluids. The proportion of oil to water is to be controlled. The ratio of oil to water can be determined by measuring the dielectric constant of the fluid. Water has a dielectric constant of around 80 at 20 degrees Celsius, and the oil component has a dielectric constant <10. Evaporation of water from the fluid causes the oil to water ratio to increase, and so it is necessary to add water to keep the emulsion concentration within the required limits.

Dielectric constant of the fluid is approximately equal to the average by volume of the two components, so for a 10% mix we would expect to see a dielectric constant of around 72. The surfactant used to keep the oil droplets in suspension is conductive as it has ionic components. Conductivity alone cannot be used to determine the emulsion concentration, as conductivity is affected by other factors such as water hardness and other ionic contamination.

The dielectric constant of water varies with temperature. Therefore, it is also desirable to measure temperature and make an appropriate compensation. FIG. 1 shows a temperature sensor 105 located with the fluid sensor cell 110. An output indicative of temperature is provided to the signal processing 130.

Other possible applications are monitoring the proportion of water in any chemical mixture (flowing or static), such as: beer/whiskey manufacturing (e.g. to determine alcohol content); bio-fuel manufacture (e.g. to monitor for water contamination); gearbox oil and lubricant monitoring.

Another possible application is measuring humidity of a gas.

Other Alternatives

The apparatus may use a single ADC and a multiplexer to time multiplex input signals to the single ADC, as shown in FIG. 4. Alternatively, the apparatus may comprise two separate ADCs, with one ADC per input signal.

The frequency of the drive signal may be selected based on the type of fluid under test. In other examples, the drive signal generator may generate a plurality of drive signals at different frequencies, or there may be a plurality of drive signal generators.

Figure 13:
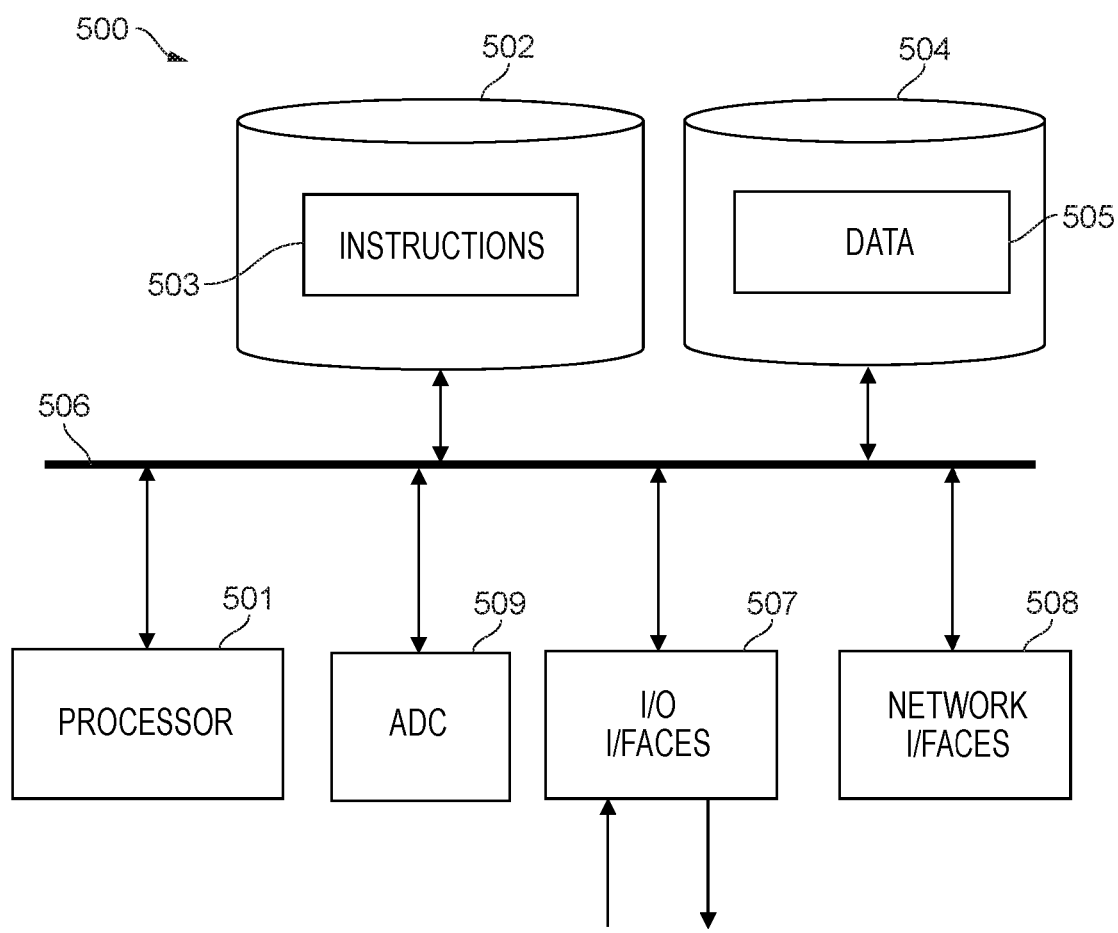
FIG. 13 show a processing apparatus.

FIG. 13 shows an example of processing apparatus 500 which may be implemented as any form of a computing and/or electronic device, and in which embodiments of the system and methods described above may be implemented. Processing apparatus may implement all, or part of, any of the methods described above. Processing apparatus 500 comprises one or more processors 501 which may be microcontrollers, microprocessors, controllers or any other suitable type of processors for executing instructions to control the operation of the device. The processor 501 is connected to other components of the device via one or more buses 506. Processor-executable instructions 503 may be provided using any computer-readable media, such as memory 502. The processor-executable instructions 503 can comprise instructions for implementing the functionality of the described methods. The memory 502 is of any suitable type such as read-only memory (ROM), random access memory (RAM), a storage device of any type such as a magnetic or optical storage device. Additional memory 504 can be provided to store data 505 used by the processor 501. The processing apparatus 500 comprises input/output (I/O) interfaces 507. The I/O interfaces 507 can receive the input signals from the sensor cell. The I/O interfaces 507 can output signals indicating the measured properties of the fluid. The processing apparatus 500 comprises one or more ADCs to sample analogue input signals, as described above. The processing apparatus 500 comprises one or more network interfaces 508 for interfacing with other network entities. The processing apparatus 500 may be implemented as a microcontroller with a processor 501, memory 502, I/O interfaces 507 and ADC 509 integrated onto a single integrated circuit.

Figure 14:
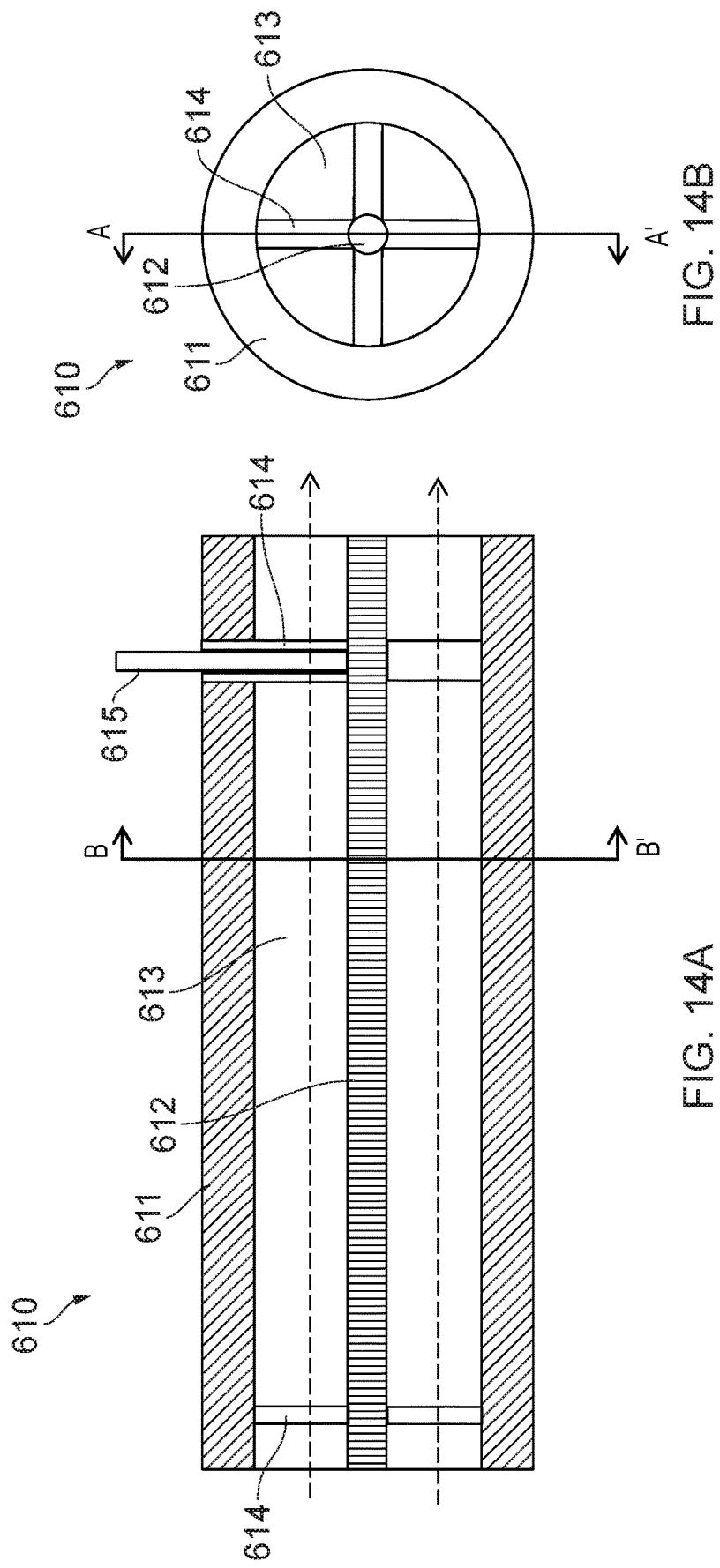
FIG. 14 shows an example fluid sensor.

FIGS. 14A and 14B show an example of a fluid sensor 610 which can be used as the fluid sensor cell 110 in any of the examples or embodiments described above. FIG. 14A shows the fluid sensor 610 in cross-section along a longitudinal axis (A-A' in FIG. 14B). FIG. 14B shows the fluid sensor 610 in cross-section along line B-B' of FIG. 14A. The fluid sensor 610 is configured for monitoring a flowing fluid. The fluid sensor 610 is a form of capacitive sensor. The sensor has a first, outer, electrode 611 and a second, inner, electrode 612. The outer electrode 611 is tubular. The inner electrode 612 is a cylindrical rod. The electrodes 611, 612 are coaxial. A fluid flow channel 613 is defined in the region between the electrodes 611, 612. Fluid can flow along the fluid flow channel 613. This allows measurements to be made without a need to interrupt a process which uses the fluid. For example, in the application of measuring a cutting fluid, the cutting fluid (or a portion of the cutting fluid) can be routed via the flow channel 613. A feed through conductor 615 connects the inner electrode 612 to a drive signal generator located outside the fluid sensor. The conductor 615 is insulated. A plurality of supports 614, shown here in the form of a cross-shaped array, support the inner electrode 612 within the outer electrode. The supports 614 are formed of an insulating material. The flow channel 613 extends through apertures between the supports 614. A set of supports 614 may be located near to each longitudinal end of the fluid sensor, as shown in FIG. 14A. As shown in FIG. 14A, one of the sets of supports 614 may incorporate the feed through conductor 615. The support 614 around the feed through conductor 615 provides a fluid-tight seal to prevent fluid loss from the sensor 610. This configuration avoids the need for a set of supports 614 and a separate tubular element for the feed through conductor 615. The fluid sensor 610 can have any suitable length and diameter.

Contaminant Concentration Determination

As described above, the system 100 may be employed to make high resolution complex impedance measurements of fluids from which both the dielectric constant of the fluid may be determined (using the I & Q values of the difference signal as described above in respect of stage 165) and conductivity of the fluid (using the I & Q values of the difference signal as also described above in respect of stage 165).

The conductivity of some fluids may be affected at least in part by the presence of one or more ionic contaminants. Accordingly, measurements of conductivity of liquids containing ions such as aqueous ionic solutions may be employed to determine the level or concentration of ions in the liquid. For low concentrations of ionic contaminants in an otherwise substantially non-conducting fluid, the conductivity may be considered to be the sum of 'conductivities' due to each ionic species.

The system 100 of FIG. 1 may be employed to measure the concentration of ions in a liquid by measuring the conductivity of the liquid and converting the conductivity to an ion concentration. This may be done, for example, by means of a look up table or by reference to an equation linking conductivity and ionic concentration. However, it is known that the conductivity of some liquids such as water varies with temperature. Consequently, it may be important in some applications to take into account the temperature of the liquid when using conductivity measurements to determine ion concentration. In some embodiments, therefore, the temperature of the liquid may also be measured and taken into account when calculating ionic concentration. For example, a formula may be employed that generates a value of ionic concentration for given values of liquid temperature and conductivity.

For example, in some embodiments a measured value of conductivity at a given temperature may be converted to an 'effective' value at a reference temperature such as 22 C and conductivity determined by reference to an equation (or a look up table or other method) linking conductivity at 22 C with ionic concentration.

In some applications, rather than obtaining an absolute measurement of ionic concentration, it is sufficient to know when the concentration difference between a liquid under inspection (the 'inspection liquid') and a reference liquid (such as local town water) is less than a critical value, such as a critical value below which the water is considered potable. In some examples of use of the present apparatus, conductivity measurements made using the system 100 in respect of a given inspection liquid may be compared (by the system 100 in some embodiments) with equivalent conductivity values obtained by measurement of a sample of local town water. The difference in conductivity values may then be considered to be an indication of the difference in ionic concentration between the liquids. In order to allow account to be taken of variations in conductivity with temperature, the temperature of the inspection liquid may be measured and the measured conductivity of the inspection liquid compared with a value of conductivity of the reference liquid at the same temperature. The conductivity of the reference liquid at a given temperature may be determined by the system 100 from a look up table or from an equation linking temperature and conductivity of the reference liquid. The equation may be obtained for example by fitting a line or curve such as a polynomial expression to data in respect of conductivity of the reference liquid as a function of temperature obtained previously using the system 100 in a calibration operation.

By way of example of an application of the system 100, we consider the case of cleaning of debris and residue from internal surfaces in industrial processing plants which process liquids, such as plants processing chemicals, foodstuffs, beverages and other fluids. Such cleaning processes may be referred to as 'clean in place' (CIP) processes. Sodium hydroxide solution is often employed in CIP processes, an aqueous solution of sodium hydroxide being pumped through pipework of the plant to clean the internal surfaces. However, it is important to thoroughly cleanse the internal surfaces of sodium hydroxide (or other cleaning substance) following treatment with sodium hydroxide so as to avoid contamination of liquids subsequently passed through the plant with sodium hydroxide. Removal of sodium hydroxide may be performed by flushing of the internal surfaces of the plant with local town water. Flushing with town water is typically performed until the concentration of sodium hydroxide in the town water that has been flushed through the plant is at a sufficiently low value to permit the plant to resume operations.

It is to be understood that the system 100 of FIG. 1 may be employed to determine when the concentration of sodium hydroxide in water that has been flushed through the plant is below a critical value. This may be achieved, for example, by measuring the temperature and conductivity of the water that has passed through the plant and comparing it to a measured value of conductivity of fresh town water (that has not been passed through the plant) at that same temperature. As described above, temperature of the liquid flowing through the sensor cell 110 may be measured by means of a temperature sensor 105.

It is to be understood that in some embodiments the conductivity of the town water prior to flushing through the system may be measured using another sensor cell 110 located upstream (with respect to the direction of flow of town water) of surfaces of the plant to be cleaned, prior to being flushed through the system, and compared with a value of conductivity measured using a sensor cell 110 located downstream of the surfaces of the plant to be cleaned. If the temperature of the local town water is assumed to be the same at each location, compensation for the temperature of the water does not need to be performed, and the system 100 may determine that the water that has been flushed through the plant is sufficiently clean if the difference in conductivity measured by the respective upstream and downstream values is sufficiently low, e.g. below a critical difference value.

However, in order to take into account the possibility of differences in temperature of the water upstream and downstream of the plant, in some embodiments the temperature of liquid passing through the respective sensor cells 110 may be measured.

In one embodiment a calibration operation is performed in which the conductivity of a given sample of local town water is determined as a function of temperature in advance of the cleaning operation. The measured values are stored for later comparison with measurements of conductivity of water that has been flushed through the plant. These measurements may be stored, for example in a look up table. Alternatively, a line or curve (such as a polynomial expression) may be fitted to the measured data and an equation determined by means of which the conductivity of local town water at a given temperature may be obtained. Other arrangements may be useful in some embodiments.

In some embodiments, the system 100 may be employed to measure both the temperature and conductivity of liquid flowing through the sensor cell 110 based on measurements of capacitance of the sensor cell 110 and conductivity of the liquid in the cell 110. In such embodiments the temperature sensor 105 is not required for the determination of the temperature of the liquid.

Figure 15:
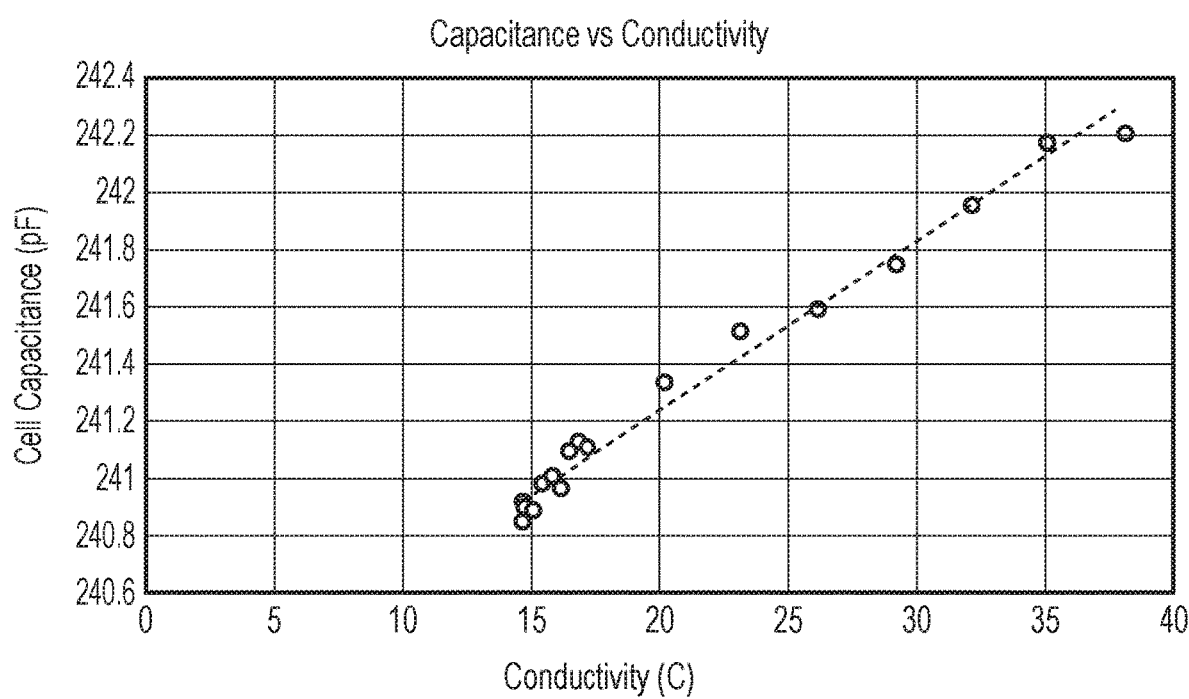
FIG. 15 is a plot of capacitance as a function of conductivity for water as the concentration of dissolved sodium hydroxide increases for a dilute aqueous solution as measured by the system of FIG. 1.

FIG. 15 is a plot of cell capacitance (pF) as a function of conductivity (mS/m) of an aqueous solution of sodium hydroxide in a sample of deionised water at 22 C obtained using the system 100 of FIG. 1. The conductivity of the aqueous solution was increased by increasing the concentration of dissolved sodium hydroxide in a sample of local town water. The conductivity of the liquid may be considered to be that of town water at 22 C plus additional conductivity due to the presence of sodium hydroxide.

Figure 16:
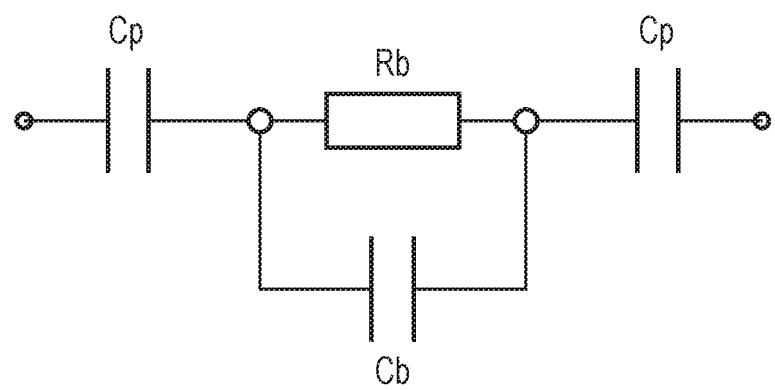
FIG. 16 is an equivalent circuit for a capacitive fluid sensor in which electrode polarisation is occurring due concentration of ions in the solution near the surface of electrodes of the sensor.

The increase in capacitance of the cell with increasing sodium hydroxide concentration is understood to be due to electrode polarisation and effects associated with parasitic inductance and capacitance within the system 100. Electrode polarisation occurs when ions in the solution concentrate near the surface of the electrodes giving rise to the equivalent circuit illustrated in FIG. 16. Cp can be very large when compared to Cb but at higher frequencies (>10 MHz) becomes a second order effect and ultimately vanishingly small.

For the data plotted in FIG. 15, the measurements for which were made at 11.24 MHz, linear regression of the data gives a gradient of 0.0582 pF·mS$^{-1}$ m (0.0582 nFΩm). This correction factor can be subtracted from the measured capacitance to compensate for the effects of electrode polarisation. This may be done by extrapolating the value of capacitance to substantially zero conductivity, and calculating the dielectric constant ($\varepsilon_r$) based on this value of capacitance. It is assumed that, for low concentrations of ions in the aqueous solution, $\varepsilon_r$ is substantially independent of ion concentration. Whilst the data shown in this example relates to an aqueous solution of sodium hydroxide, a similar methodology can be used with other aqueous solutions and other liquids in order to compensate for the effects of electrode polarisation and/or effects associated with parasitic inductance and/or capacitance within the system 100.

Figure 17:
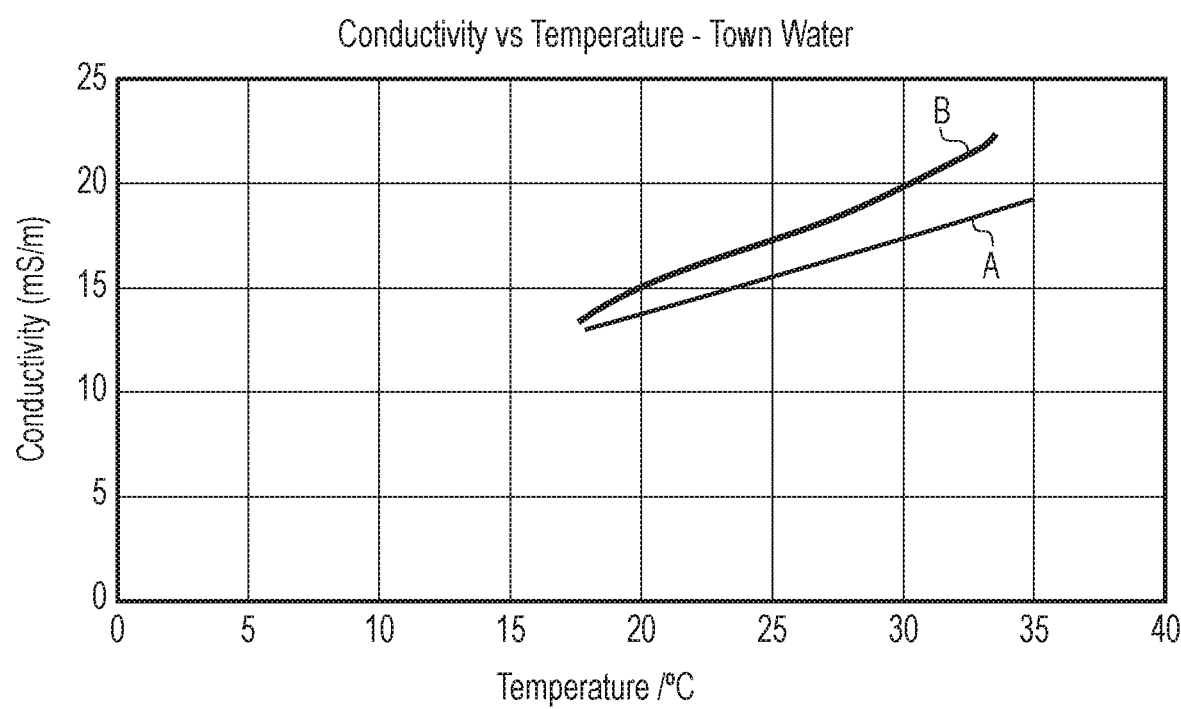
FIG. 17 is a plot of conductivity (mS/m) as a function of temperature (Celsius) for a sample of town water (trace A) and town water with a few parts per million (ppm) of dissolved sodium hydroxide as measured by the system of FIG. 1.
Figure 18:
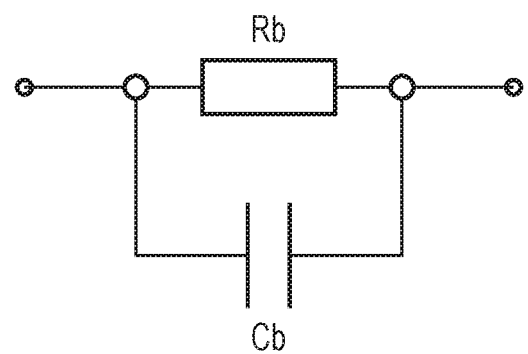
FIG. 18 is an equivalent circuit in respect of a capacitive fluid sensor as used to obtain the data of FIG. 17 in which a resistor of resistance $R_b$ is connected in parallel with a capacitor of capacitance $C_b$.

FIG. 17 is a plot of conductivity (mS/m) as a function of temperature (Celsius) for a sample of town water (Birmingham, UK) (trace A) as measured by the system 100. The fluid may be considered to be a conductive medium having a resistance with a parallel capacitance equal to a cell-factor (associated with the geometry of the fluid sensor cell 110) multiplied by the relative dielectric permittivity $\varepsilon_r$ of the medium. An equivalent circuit is illustrated in FIG. 18 in which a resistor of resistance $R_b$ is connected in parallel with a capacitor of capacitance $C_b$.

Trace B of FIG. 17 illustrates the expected variation in conductivity (as a function of temperature) following the introduction of a few ppm of sodium hydroxide.

In the case of CIP systems, when flushing cleaning fluid from a system that has been cleaned with cleaning fluid (such as hot sodium hydroxide solution), we consider the fluid medium to be primarily water with additional components that typically constitute less than 0.1% of the total weight, at least in the latter stages of the flushing process.

The value of capacitance measured by the system 100 can be considered to be:

$$C_{meas} = (F \times \varepsilon_r) + (\alpha \times \sigma)$$

where:

F is the cell factor (a constant that is determined by the geometry of the electrodes)

$\varepsilon_r$ is the dielectric constant of water

α is the gradient of the plot of cell capacitance (pF) as a function of conductivity (mS/ms) shown in FIG. 15 as discussed above σ is the measured conductivity.

Hence an estimate of $\varepsilon_r$ can be derived:

$$\varepsilon_r = \frac{c_{meas} - (\alpha \times \sigma)}{F} \quad (1)$$

By obtaining data in respect of cell capacitance of town water (i.e. measured capacitance of the sensor cell 610 when filled with town water) as a function of temperature (temperature being measured for example using a temperature sensor such as a thermometer of infra-red (IR) temperature sensor device) and knowing the value of dielectric constant (relative dielectric permittivity of water, $\varepsilon_r$) as a function of temperature (e.g. from the literature), it is possible subsequently to deduce the temperature of liquid in the sensor cell based solely on a measurement of the cell capacitance. This is because the measured value of cell capacitance can be used to calculate the dielectric constant $\varepsilon_r$ of the liquid, from which temperature can be deduced by linear interpolation of (say) literature values of data in respect of dielectric constant $\varepsilon_r$ as a function of water.

Figure 19:
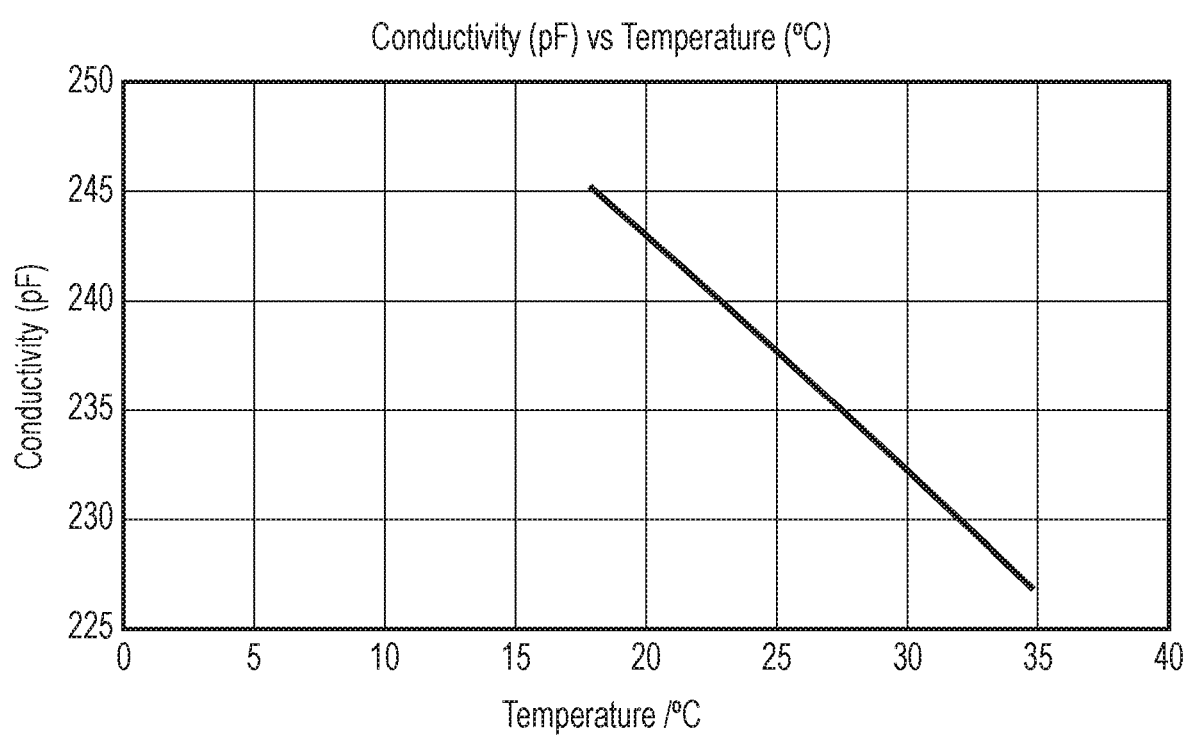
FIG. 19 is a plot of cell capacitance as a function of temperature (measured using a temperature sensor in the form of an infra-red (IR) temperature sensor device) obtained using the system of FIG. 1 with a similar sample of town water to that used to obtain trace (A) of FIG. 17.

By way of example, FIG. 19 is a plot of cell capacitance as a function of temperature (measured using a temperature sensor in the form of an infra-red (IR) temperature sensor device) obtained using the system 100 with a similar sample of town water to that used to obtain trace (A) of FIG. 17. Table 1 below shows values of dielectric constant at 20 C and 35 C (obtained from literature as described below), together with the measured values of cell capacitance (pF) and cell factor for town water (Birmingham, UK) at 20 C and 35 C (obtained from the data represented in FIG. 19). The values of dielectric constant listed in Table 1 were obtained from Malmberg and Maryott (J Res Natl Bur Stand 56(1), January 1956, Res Pap 2641, page 6) who made the measurements using distilled water.

TABLE 1

| Temperature (° C.) | Relative Dielectric Permittivity ($\varepsilon_r$) (Malmberg and Maryott) | Measured cell capacitance (pF) | Cell factor (pF) = Cell cap/$\varepsilon_r$ |
|---|---|---|---|
| 20 | 80.103 | 243.0 | 3.034 |
| 35 | 74.828 | 226.8 | 3.030 |

The following equation may be employed to determine temperature of the liquid based on measurements of $\varepsilon_r$:

$$T = a \cdot \varepsilon_r + b \quad (2)$$

Where a is the gradient of a plot of $\varepsilon_r$ as a function of temperature and b is the intercept of a best fit line to a plot of $\varepsilon_r$ as a function of temperature. It is to be understood that this equation is valid for water with less than around 0.1% dissolved solids, at least, since account has been taken of the effects of electrode polarisation as described above with respect to FIG. 15.

In this particular case, based on the data in Table 1:

$$T = 20 + \frac{(\varepsilon_r - 80.103) \times 15}{74.828 - 80.103} \quad (3)$$

The variation of $\varepsilon_r$ as a function of temperature is approximated to be linear over the range from 20 to 35 C and can be seen to vary approximately at a rate of $-0.3516$ K$^{-1}$. This corresponds to a change in capacitance of $-1.0668$ pF·K$^{-1}$. The cell factor is determined by the geometry of the cell 110 as noted above, but can be calculated here as the ratio of cell capacitance to the literature value of dielectric permittivity of distilled water. The value of cell factor should be substantially constant as a function of temperature. The resolution of the instrument is approximately 0.1 pF, hence in this particular case a temperature resolution of around 0.1K may be obtained. It will be appreciated that this is a very high resolution, high speed measurement of fluid temperature rivalling some of the most expensive alternative technologies such as resistance temperature detectors (RTDs). It is to be understood that alternative technologies typically measure the temperature of surfaces in contact with fluid whereas embodiments of the present invention enable direct measurements to be made on the fluid itself.

Thus, it is to be understood that the system 100 may be employed to measure the temperature of a fluid directly, based on measurements of conductivity and dielectric constant of the fluid. This feature is advantageous in that a separate temperature sensor may not be required to be provided (such as sensor 105 in the embodiment of FIG. 1), reducing the cost and enhancing reliability of the system 100. Furthermore, accuracy of the measurement of temperature is improved since the temperature of the fluid itself is measured directly, rather than indirectly by means of a temperature sensor which relies on the temperature of the sensor equilibrating with that of the fluid. Thus, some embodiments of the present invention may be capable of measuring fluid temperature more quickly and more reliably. The effect of environmental changes in temperature may also be reduced.

It is to be understood that, in some embodiments, a separate temperature sensor such as sensor 105 may be provided in order to facilitate calibration of the system 100, 600. Thus the temperature sensor 105 may be used to obtain data in respect of cell capacitance of town water (i.e. measured capacitance of the sensor cell 110, 610 when filled with town water) as a function of temperature instead of a separate temperature sensor such as an IR temperature sensor device. It is to be understood that, whilst such temperature sensors may have lower resolution in terms of temperature measurements than can be obtained by means of the system 100, 600 when measuring temperature based on measurements of cell capacitance, the output of the sensor 105 may be averaged over a period of time and the averaged value used to determine the temperature of liquid in the cell 110, 610.

Once the temperature of the liquid is known, the concentration of sodium hydroxide ions in the water may be deduced based on measurements of the conductivity of the liquid. For example, the measured value of conductivity (and temperature) may be compared with stored data relating temperature and conductivity to ion concentration. Linear interpolation may be employed to determine the ion concentration at temperatures and conductivity values for which direct measurements are not available. The system may for example store an algorithm relating temperature and conductivity to ion concentration. For example, it might be found that the addition of (say) 1 ppm (part per million) of NaOH to town water increases the conductivity of the water by (say) 0.2 mS/m at room temperature. The increase in conductivity of water as a function of temperature might be assumed to be 2 mS/m per K based on the data shown in FIG. 17 and assumed to be approximately this value at low ionic concentrations (i.e. with or without the addition of NaOH). The concentration of ions in an aqueous solution, at relatively low ion concentrations (e.g. less than around 0.1 weight percent) can then be determined based on measurements of conductivity and temperature of liquid in the sensor cell 110, 610.

In some embodiments, the measured value of conductivity may be converted to an effective value at a reference temperature, being a temperature for which values of conductivity as a function of sodium hydroxide concentration are available, and the concentration of sodium hydroxide determined from this data.

It is to be understood that a determination of the concentration of ions in an aqueous solution has been described in which measurements of conductivity are employed to determine ion concentration. A method of taking into account the effects of temperature on conductivity has also been described, since conductivity of an aqueous solution typically increases with increasing temperature (for a given ion concentration) as well as with increasing ion concentration (at a given temperature). Temperature may be measured by means of the sensor cell, or by means of a separate temperature sensor.

However, it is to be understood that it is possible to calculate a temperature-corrected value of concentration of ions in an aqueous solution without actually calculating the temperature of the liquid. This may be achieved by:

(a). Correcting a measurement of capacitance for electrode polarisation to obtain a 'corrected' value of capacitance related to the bulk dielectric constant as previously; and (b). Comparing the measured value of conductivity of the aqueous solution with a plot of conductivity versus the corrected value of capacitance obtained from (a).

For any given reported corrected capacitance (as opposed to a value of temperature deduced from the measurements in the manner described above), the difference between measured and stored conductivity values provides an indication of the concentration of sodium hydroxide in the aqueous solution.

Figure 20:
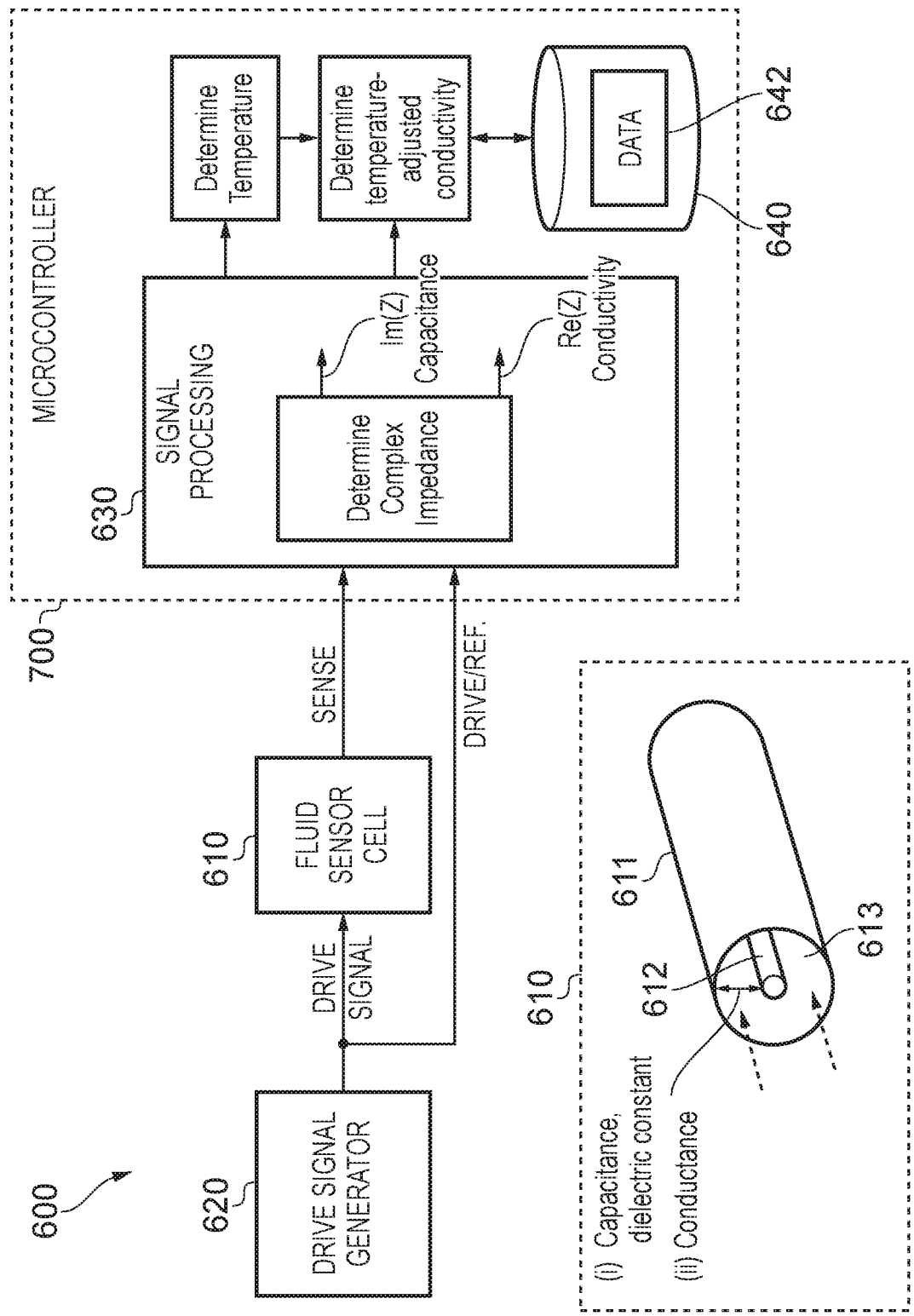
FIG. 20 illustrates a system according to an embodiment of the present invention adapted for use in beverage transport lines in an industrial plant.

FIG. 20 illustrates a system 600 according to an embodiment of the present invention adapted for use in liquid transport lines in an industrial plant. The system 600 is configured to determine when the concentration of sodium hydroxide in water is below a critical (safe) value following a cleaning operation using aqueous sodium hydroxide solution. Like features of the system 600 of FIG. 20 to that of the system 100 of FIG. 1 are shown with like reference signs incremented by 500. Although not shown for clarity, the microcontroller/processing apparatus 700 may comprise the signal processing functions shown in FIG. 4.

The system 600 includes the fluid sensor cell 610 of FIG. 14A and FIG. 14B in combination with a drive signal generator 620 and microcontroller 700 that includes signal processing stage 630. In contrast to the system 100 of FIG. 1, the system 600 of FIG. 20 does not include a temperature sensor 105. This is because the system 600 is configured to determine fluid temperature based on measurements of conductivity of the fluid and capacitance of the cell 610 with fluid therein in the manner described above.

The processing apparatus 700 is configured to determine a complex impedance of the fluid sensor 610 based on the sense signal and the drive/REF signal. This can be performed as described in detail above, such as by using a ratio Cs/Cr and an algorithmic model of the apparatus to determine the complex impedance. The complex impedance comprises an in-phase component indicative of a conductivity quantity of a fluid in the sensing region 613 and a quadrature component indicative of a capacitance quantity of the fluid sensor. The processing apparatus 700 is configured to determine a temperature of the fluid in dependence on at least the determined capacitance quantity of the fluid sensor 610.

The processing apparatus 700 uses data 642 stored in a memory 640. The system 600 is configured to be calibrated by inputting to a memory 640 of the microcontroller 700 two parameters, being the values of gradient (g) and intercept (h) of a best-fit line to a plot of conductivity of a sample of local town water as a function of temperature over the temperature range from 5 C to 35 C:

$$\sigma_{town} = g \cdot T_{meas} + h \tag{3}$$

where:

$\sigma_{town}$ is the conductivity of local town water as received at the plant before flushing through the plant; and $T_{meas}$ is the temperature of local town water that has been flushed through the plant as measured by the sensor cell 610 at the point at which conductivity (and capacitance) is measured.

The values of gradient (g) and intercept (h) are sufficient to enable subsequent calculation of the conductivity of the local town water for a given temperature value. The range 5 to 35 C was selected in respect of the present embodiment in order to cover substantially the entire range of temperatures of local town water in the particular region in which the system 600 is operated. Best fit lines to other temperature ranges may be employed instead if desired, for example depending on the expected range of variation of local water temperature.

It is to be understood that, in some alternative embodiments, best-fit lines other than linear best-fit lines may be employed, including polynomial expressions such as second order polynomial expressions.

In addition to the values of gradient and intercept described above, the calibration operation also involves storing values of parameters F (cell factor) and a (gradient of the plot of cell capacitance (pF) as a function of conductivity (mS/ms) shown in FIG. 15) described with respect to equation (1) above.

Furthermore, the calibration operation involves obtaining the gradient a and intercept b of equation (2) above describing the rate of change of $\varepsilon_r$ with temperature over the range from 5 C to 35 C (gradient a being in units of $K^{-1}$ whilst intercept b is dimensionless). Values of a and b for best fit lines to plots of $\varepsilon_r$ as a function of temperature over other temperature ranges such as 100 to 30 C, 100 to 25 C or any other suitable temperature range covering the expected temperature ranges of liquids encountered by the sensor cell 610 may be employed in some other embodiments. As described above, appropriate values of $\varepsilon_r$ of water as a function of temperature may be obtained from the literature, and taken as an approximation to the value of $\varepsilon_r$ of local town water as a function of temperature.

The value of $\varepsilon_r$ of a given sample of liquid in the sensor cell 610 may be determined by means of equation (1) above. The linear equation relating $\varepsilon_r$ and temperature (equation 3 above) may then be employed to calculate the temperature of the liquid in the sensor cell 610 based on measurements of $\varepsilon_r$ (made using the apparatus). As noted above, equation (3) is presented by way of example of such an empirically determined equation. In some alternative embodiments, $\varepsilon_r$ of liquid at a given temperature may be obtained based on stored measurements of $\varepsilon_r$ as a function of temperature, $\varepsilon_r$ at a given temperature then being determined directly from the data or by interpolation between data points.

FIG. 21 is a flow diagram illustrating the manner in which the system 600 is able to determine whether the flushing fluid (town water), and therefore the internal surfaces of the plant, are sufficiently clean (with respect to sodium hydroxide contamination following cleaning with hot sodium hydroxide solution) to permit the plant to be returned to service in one example embodiment.

At step S201 the system 600 determines values of conductivity $\sigma_{meas}$ and capacitance $C_{meas}$ of a liquid flowing through the sensor cell 610.

At step S203, equation (1) above is employed to determine the value of $\varepsilon_r$ of the liquid flowing through the sensor cell 610 based on the measured values of conductivity $\sigma_{meas}$ and capacitance $C_{meas}$.

At step S205, equation (2) (with empirically determined values of a and b) is employed to calculate the temperature $T_{curr}$ of the liquid currently flowing through the sensor cell 610.

At step S207 the value of $T_{curr}$ is employed to determine the conductivity $\sigma_{town}$ of local town water prior to flushing through the plant using equation (3).

At step S209 the system 600 calculates the difference am between measured conductivities $\sigma_{meas}$ and $\sigma_{town}$, $\sigma_{meas} - \sigma_{town} = \sigma_{diff}$.

At step S211 the system 600 determines whether the difference $\sigma_{diff}$ is greater than a threshold difference value, $\sigma_{thresh}$. If the difference $\sigma_{diff}$ is greater than threshold difference value $\sigma_{thresh}$, the system displays a message 'cleaning in progress' to a user. The system 600 then continues at step S201. If the difference $\sigma_{diff}$ is not greater than threshold difference value $\sigma_{thresh}$, then the system continues at step S213.

At step S213, the system 600 displays a message 'cleaning complete'. Alternatively, or in addition, the system 600 may generate an audible output to indicate that cleaning is complete, such as an alarm or other alert sound.

It is to be understood that other methods of operation may be employed. For example, in some embodiments, at step S209 the system 600 may calculate the modulus of the difference between measured conductivities, $|\sigma_{diff}|$.

In some embodiments, at step S213 the system may, in addition or instead, perform one or more other actions such as notifying an operator by means of the transmission of a message by a wired or wireless communications link, close or open one or more valves controlling fluid flow, or one or more alternative actions. The actions may be part of the operation of an automated plant control system.

Figure 22:
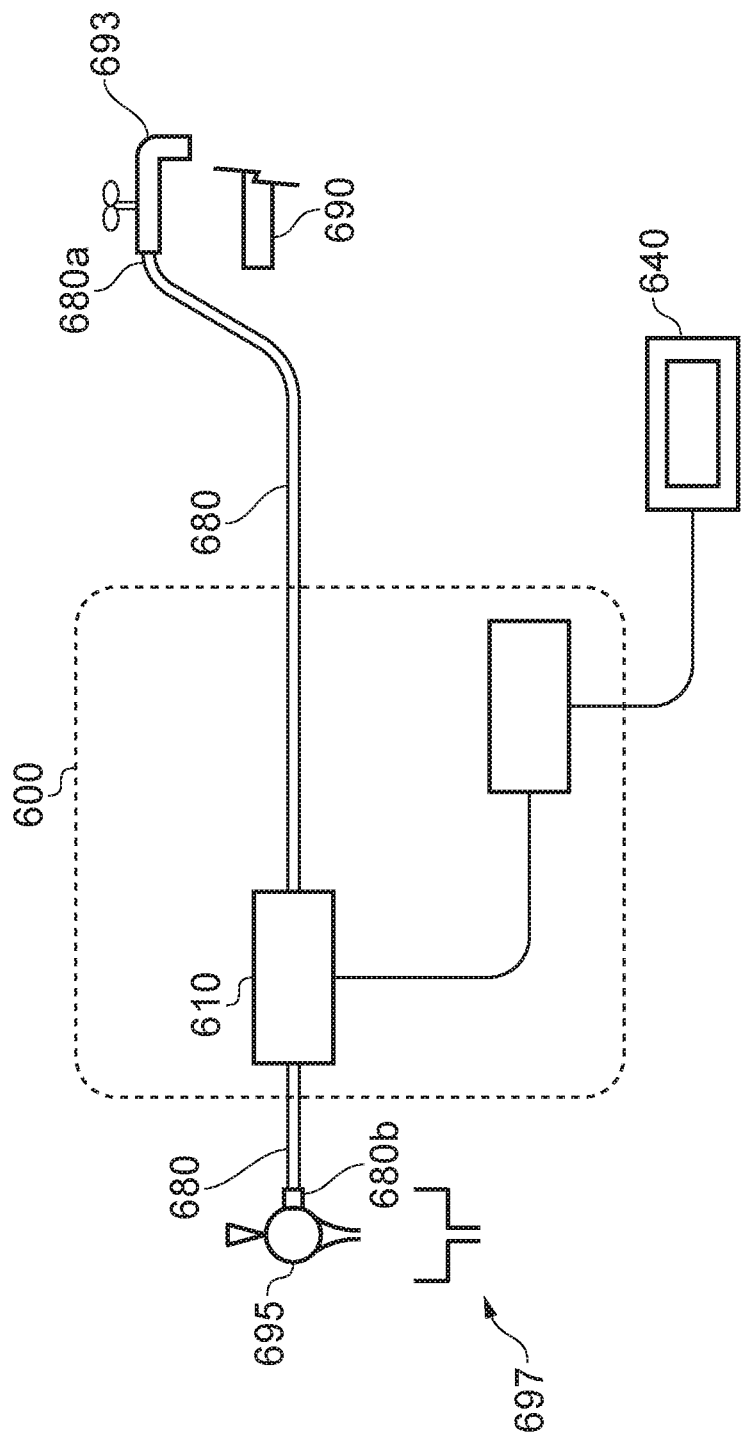
FIG. 22 illustrates a system according to an embodiment of the present invention connected in-line in a beverage dispense line situated in a retail establishment during a cleaning operation.

FIG. 22 illustrates the system 600 connected in-line in a beverage dispense line 680 situated in a retail establishment during a cleaning operation in which the dispense line 680 has been filled with hot sodium hydroxide solution in order to clean the line 680. At the stage shown in FIG. 22, the dispense line 680 is in the process of being flushed with town water from a tap (faucet) 693 that is connected to the mains water supply. As shown in FIG. 22, water from the tap 693 is being fed into the dispense line 680 at first end 680a and is being drained from the dispense line 680 at second end 680b via a user-operated dispense tap 695 located at the point of service of beverage from the line 680. The dispense tap 695 may for example be located in a restaurant of a retail outlet and used by staff or customers to dispense a beverage. Water flowing out from the dispense tap 695 falls into a catch tray 697 which is in turn connected to a mains water drain of the retail outlet.

It is to be understood that during normal beverage dispense operations the first end 680a of the dispense line 680 would be connected to a beverage source 690.

During the flushing operation, the system 600 monitors the conductivity of the liquid flowing through the sensor cell 610 and follows the process shown in the flow diagram of FIG. 21. A human machine interface (HMI) 640 displays the message 'cleaning in progress' or 'cleaning complete' on the HMI 640 in dependence on the difference $\sigma_{diff}$ between measured conductivities $\sigma_{meas}$ and $\sigma_{town}$ as set out at steps S209, S211 and S213 of FIG. 21. The system 600 provides both the visual alert to the user via the HMI 640 and an audible alert to an operator to inform them that the concentration of sodium hydroxide remaining in liquid in the dispense line 680 is no longer above the threshold value, and that dispensing of beverage may recommence.

The operator may then reconnect the first end 680a of the beverage dispense line 680 to the beverage source 690 and commence dispensing of beverage from the source 690. It is to be understood that the operator may first clear the dispense line 680 of tap water by opening the dispense tap 695 to cause beverage to flow from the source 690 until beverage flows out from the dispense tap 695. The operator may then proceed to serve beverage to customers. It is to be understood that in some embodiments the beverage may be diluted by the presence of town water in the dispense line 680 when beverage first flows through the line 680 following the flushing operation. The system 600 may be employed, if desired, to determine when the level of dilution of beverage by town water is sufficiently low to permit dispensing of beverage to customers. In other words, the system 600 may be employed to determine when the concentration of beverage in liquid flowing through the sensor cell 610 is sufficiently high to permit dispensing of beverage to customers. It is to be understood that this may be done, again, by comparing the conductivity of liquid as measured by the sensor cell, $\sigma_{meas}$, with a stored reference value of the conductivity of the beverage in substantially undilute form, $\sigma_{bev}$, determining a difference between the values, $\sigma_{diff}$, and determining that the beverage is sufficiently undilute when the difference value $\sigma_{diff}$ is sufficiently small. Other arrangements may be useful. It is to be understood that the system 600 may take into account variations in $\sigma_{bev}$ as a function of temperature by measuring the temperature of the beverage, either by means of measurement of a property of the liquid such as relative dielectric constant $\varepsilon_r$, or by means of a separate temperature sensor such as sensor 105 which may be installed in the sensor cell 610.

Figure 23:
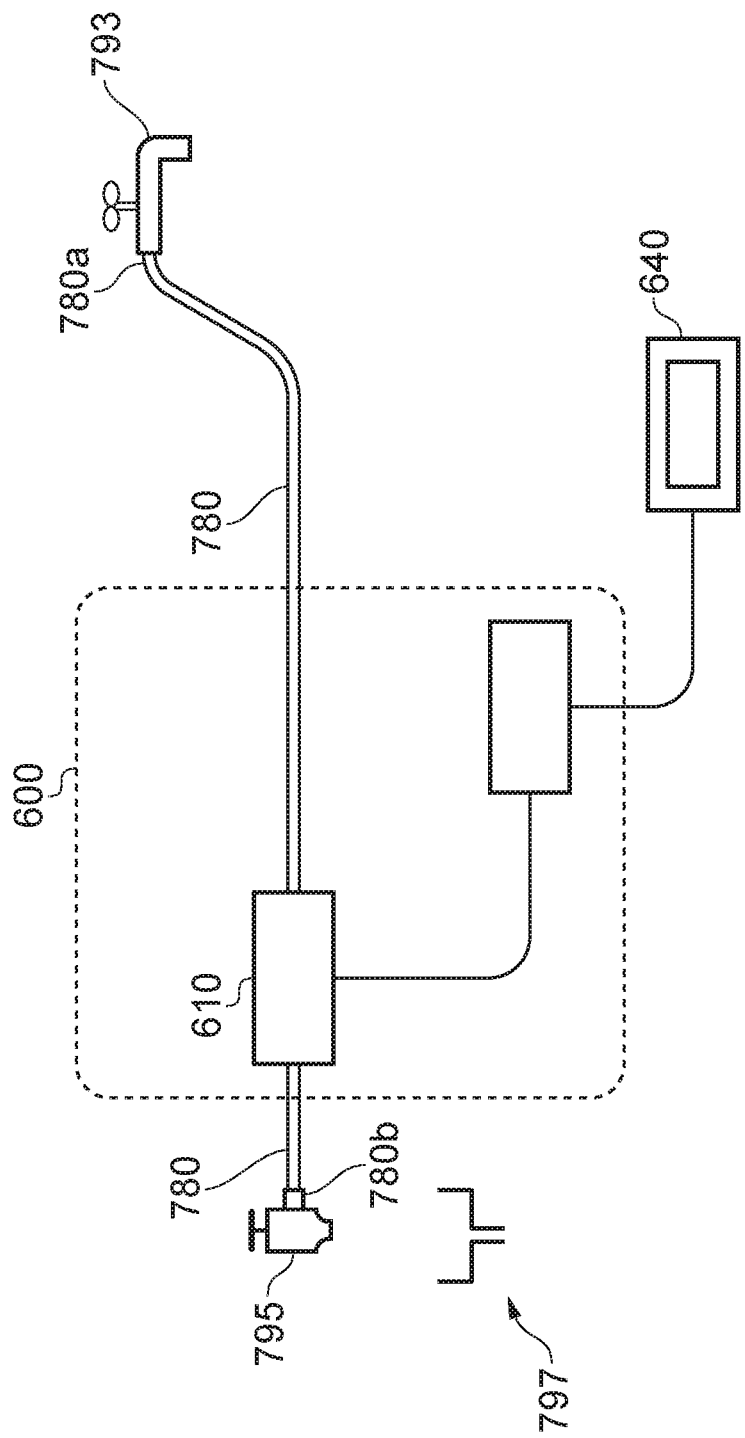
FIG. 23 illustrates use of a system according to an embodiment of the present invention in an industrial process in a processing plant.

FIG. 23 illustrates use of the system 600 of FIG. 20 in another industrial process in which sodium hydroxide has again been used to clean residue from within a product flow line 780 in a processing plant. As described above, in some embodiments a flushing substance such as town water may be used to flush a fluid in the plant from the plant. The fluid in the plant that is to be flushed may be a cleaning fluid that has been used to clean internal surfaces of the plant or an industrial product or other product. By way of example, the product may be a beverage or foodstuff such as fruit juice, milk, a soft drink, a beer, a wine, a spirit or any other suitable beverage or foodstuff. Similarly the product may be an emulsion such as a paint, a glue or any other suitable product.

Thus, in some examples it may be required to flush a liquid of a first type such as a particular type or brand of fruit juice from pipework in a bottling plant using a liquid of a second type such as another fruit juice in order to allow bottling of the second type of liquid instead of the first type. This may be accomplished by flushing the first type of liquid from the pipework 780 by pumping liquid of the second type through the pipework (e.g. from tap 793) until traces of residue of the first type of liquid in the pipework 780 have been substantially removed. The apparatus 600 may be employed to compare data indicative of at least one property of the flushing liquid (e.g. liquid of the second type) such as a conductivity of the flushing liquid as it passes through the sensor cell 610 with corresponding data in respect of a sample of the flushing liquid before flushing through the plant (in the present example, liquid of the first type) and to determine that the flushing operation is complete when a difference between the data (conductivity values in the present example) is less than a threshold amount. The threshold amount may be determined empirically, being an amount corresponding (in the present example) to a sufficiently dilute (trace) amount of liquid of the first type in liquid of the second type passing through the sensor cell 610. In some embodiments the acceptable level may be set to a level where substantially no liquid of the first type is detectable in liquid of the second type (e.g. any amount is below the limit of detectability). It is to be understood that the data indicative of at least one property of the first and second liquids may be referred to as a 'fingerprint', or 'product fingerprint'. Data corresponding to a 'fingerprint' of a given product may be obtained empirically using systems according to embodiments of the present invention or by other means and used in methods and apparatus according to embodiments of the present invention. Data in respect of a variation of data indicative of the at least one property as a function of a parameter such as temperature may be obtained and employed to compensate for changes in temperature of liquid inspected by means of systems according to embodiments of the invention.

End Point Prediction

In some embodiments, the system 600 may use the calculated values of $\sigma_{diff}$ or $|\sigma_{diff}|$ to predict when the difference $\sigma_{diff}$ between measured conductivities meas and a town will no longer be greater than threshold difference value $\sigma_{thresh}$. The system 600 may do this, for example, by periodically storing values of $\sigma_{diff}$ or $|\sigma_{diff}|$ and extrapolating the measured values to determine the time at which $\sigma_{diff}$ or $|\sigma_{diff}|$ will no longer be greater than $\sigma_{thresh}$. Extrapolation may be performed by fitting a mathematical expression to the measured data values, such as an exponential decay function, a polynomial expression such as a second or third (or higher) order expression, or any other suitable mathematical function.

It is to be understood that predictive functionality in terms of the time at which the plant is expected to be clean ('end point prediction') may be helpful in applications where industrial processes may be stopped or paused in order to facilitate cleaning of (say) product outlet lines for the product(s) of one or more processes. Knowing the time remaining before cleaning will be complete can be helpful in enabling processes to be restarted before cleaning is complete so that product is ready to flow through the outlet lines when or soon after cleaning is complete. Other scenarios may benefit from advance knowledge of the time remaining before cleaning is complete. It is to be understood that, in some embodiments, the system 600 may provide a display indicating the local time at which cleaning is expected to be complete, e.g. "Cleaning expected complete at 11:30 am" or in terms of time remaining before cleaning is complete, with a timer countdown feature, e.g. "Time remaining before cleaning is complete: 0 h:23 mins". Other arrangements may be useful. In some environments such as automated environments, no visual or audible output may be provided in some embodiments.

In an embodiment implementing end point prediction, the system 600 may measure and store values corresponding to the conductivity of the liquid passing through the sensor cell 610 as a function of time. The system 600 may use the stored data to predict when the conductivity will be at or below the safe threshold value. The system 600 may then provide an output indicative of the time at which the conductivity will be at or below the safe threshold value. For example, as noted above, in some embodiments the system 600 may provide an indication of the time remaining before the conductivity will be at or below the safe threshold value (e.g. in hours, minutes and/or seconds), or the time (e.g. local time) at which the conductivity will be at or below the safe threshold value. Other arrangements may be useful in some embodiments.

The system 600 may be configured to predict when the conductivity will be at or below the safe threshold value by fitting a curve to the stored data and extrapolating the data forward in time. The system 600 may be configured to fit the stored data to a predetermined curve type such as an exponential curve, polynomial equation such as a second order, third order or any other suitable order of polynomial equation, or any other suitable predetermined curve type including in some embodiments a substantially straight line.

FIG. 24 is a flow diagram illustrating the prediction of the end point of a flushing process in which a flushing fluid is flushed through plant in order to remove a contaminant fluid being a fluid that it is required to be removed from within the plant.

At step S301 the system 600 measures the conductivity meas and capacitance $C_{meas}$ of flushing fluid flowing through cell 610. It is to be understood that in the present embodiment the system 600 measures the conductivity meas and capacitance $C_{meas}$ repeatedly at a frequency of around two readings per second. However other frequencies may be useful including higher or lower frequencies depending on the rate of flow of liquid through the sensor cell 610 and rate of change of liquid composition/conductivity as a function of time. In the case that an average value of multiple readings over a period of time is calculated, the choice of rate at which readings are taken may also be influenced by the number of readings that are to be used to obtain an average value.

At step S303 the system 600 determines the value of $\varepsilon_r$ of the flushing fluid using equation (1) and the measured values of conductivity $\sigma_{meas}$ and capacitance $C_{meas}$.

At step S305 the system 600 determines the current temperature $T_{curr}$ of fluid in cell 610 by inserting the value of $\varepsilon_r$ calculated at step S303 into equation (2).

At step S307 the system 600 determines the conductivity $\sigma_{flush}$ of flushing fluid at $T_{curr}$ by means of a stored equation (equation (3) above) linking conductivity and temperature of flushing fluid as introduced to the plant. This equation is determined empirically before use of the system 600 in a calibration operation as described above in respect of the flow chart of FIG. 21.

At step S309 the system 600 calculates the magnitude of a difference $|\sigma_{diff}|$ between measured conductivities $\sigma_{meas}$ and $\sigma_{flush}$, $|\sigma_{meas} - \sigma_{flush}| = |\sigma_{diff}|$.

At step S311 the system 600 stores the value of $|\sigma_{diff}|$ in a memory of the system 600 together with an indication of the time at which the measurement was made (e.g. local time or time elapsed since the flushing operation began). In some embodiments the system 600 may simply store values such that a chronological order in which the values were obtained by means of the sensor cell 610 is known. The system 600 then checks how many stored values of $|\sigma_{diff}|$ in respect of the current flushing operation are in the memory. If the number exceeds 10 the system moves to step S313 else the system moves to step S301. It is to be understood that in the present embodiment 10 readings corresponds to an elapsed time of approximately 5 s from the first to the last readings. Other numbers of readings may be used to determine when to first move to step S313 at the start of a flushing operation in alternative embodiments such as 5, 20, 50, 100 or any other suitable number.

At step S313 the system 600 compares the value of $|\sigma_{diff}|$ with a threshold difference value $\sigma_{delta}$. If $|\sigma_{diff}|$ is greater than threshold difference $\sigma_{delta}$ then the system 600 moves to step S315 else the system moves to step S317. It is to be understood that, in some embodiments, the system 600 may calculate an average value of $|\sigma_{diff}|$, $|\sigma_{diff}|_{av}$ over a prescribed number of measurements of $|\sigma_{diff}|$ such as 10 measurements or more, and compare the value of $|\sigma_{diff}|_{av}$ with a threshold difference value $\sigma_{delta}$ in order to determine which step to execute next. This is so as to reduce the risk that an incorrect determination that the cleaning process has ended occurs due to an anomalous measurement. Such a measurement may be obtained due, for example, to noise or a local unexpected variation in composition of fluid being inspected.

At step S315 the system 600 displays a message 'cleaning in progress'. The system 600 also calculates a best-fit polynomial expression to the stored data points in respect of $|\sigma_{diff}|$ (or $|\sigma_{diff}|_{av}$) as a function of time. The system 600 employs the polynomial to obtain an estimate of the amount of time remaining before the value of $|\sigma_{diff}|$ (or $|\sigma_{diff}|_{av}$) is expected to be substantially equal to or less than $\sigma_{delta}$. The system then displays the message, "Time remaining before cleaning is complete: Xh:Ymins", where the calculated expected time to completion is X hours and Y minutes. The system then continues at step S301. Other ways of displaying the time remaining may be useful, such as the number of seconds.

At step S317 the system 600 displays the message 'cleaning complete' and generates an audible alert to inform an operator that cleaning is now complete.

It is to be understood that systems according to embodiments of the present invention may be used in applications where a fluid of one conductivity value is to be purged or flushed or otherwise replaced by a fluid of a second conductivity, and it is desirable to know when the residual amount of any of the first fluid in the second fluid (as measured with respect to conductivity of a given sample of second fluid that may contain the first fluid) is below a threshold amount. Example applications include those where the first and second fluids are respective different beverages or foodstuffs or any other suitable products such as paints, pharmaceuticals, waste waters or any other suitable fluid. Optionally, as discussed herein, the first fluid may be a cleaning fluid for cleaning internal surfaces of the fluid handling plant and the second fluid may be a flushing fluid such as water or any other suitable flushing fluid. Other arrangements may be envisaged.

Some embodiments of the invention may be employed to determine the concentration of one or more contaminants in a given fluid. Some embodiments may be employed, in addition or instead, to compare one or more parameters (such as the conductivity) of a fluid passing through the system with one or more corresponding parameters of a reference fluid and to perform an action in dependence on the result of the comparison. For example if the difference in conductivities is below a threshold value, the system may provide an indication that such is the case, for example by providing an indication that a flushing, cleaning or purging operation is complete.

Other applications of the system and apparatus may be envisaged.

One embodiment of the present invention provides processing apparatus configured to receive a sense signal from a capacitive fluid sensor comprising a first electrode and a second electrode with a sensing region between the electrodes. The processing apparatus is configured to receive an alternating drive signal applied to the capacitive fluid sensor. The processing apparatus is configured to determine a complex impedance of the fluid sensor based on the sense signal and the drive signal, the complex impedance comprising an in-phase component indicative of a conductivity quantity of a fluid in the sensing region and a quadrature component indicative of a capacitance quantity of the fluid sensor. The processing apparatus is configured to determine a temperature of the fluid in dependence on at least the determined capacitance quantity of the fluid sensor.

Identifying a Fluid

There are various applications where it is desirable to identify if a fluid composition is the same as, or similar to, an expected fluid composition.

Figure 25:
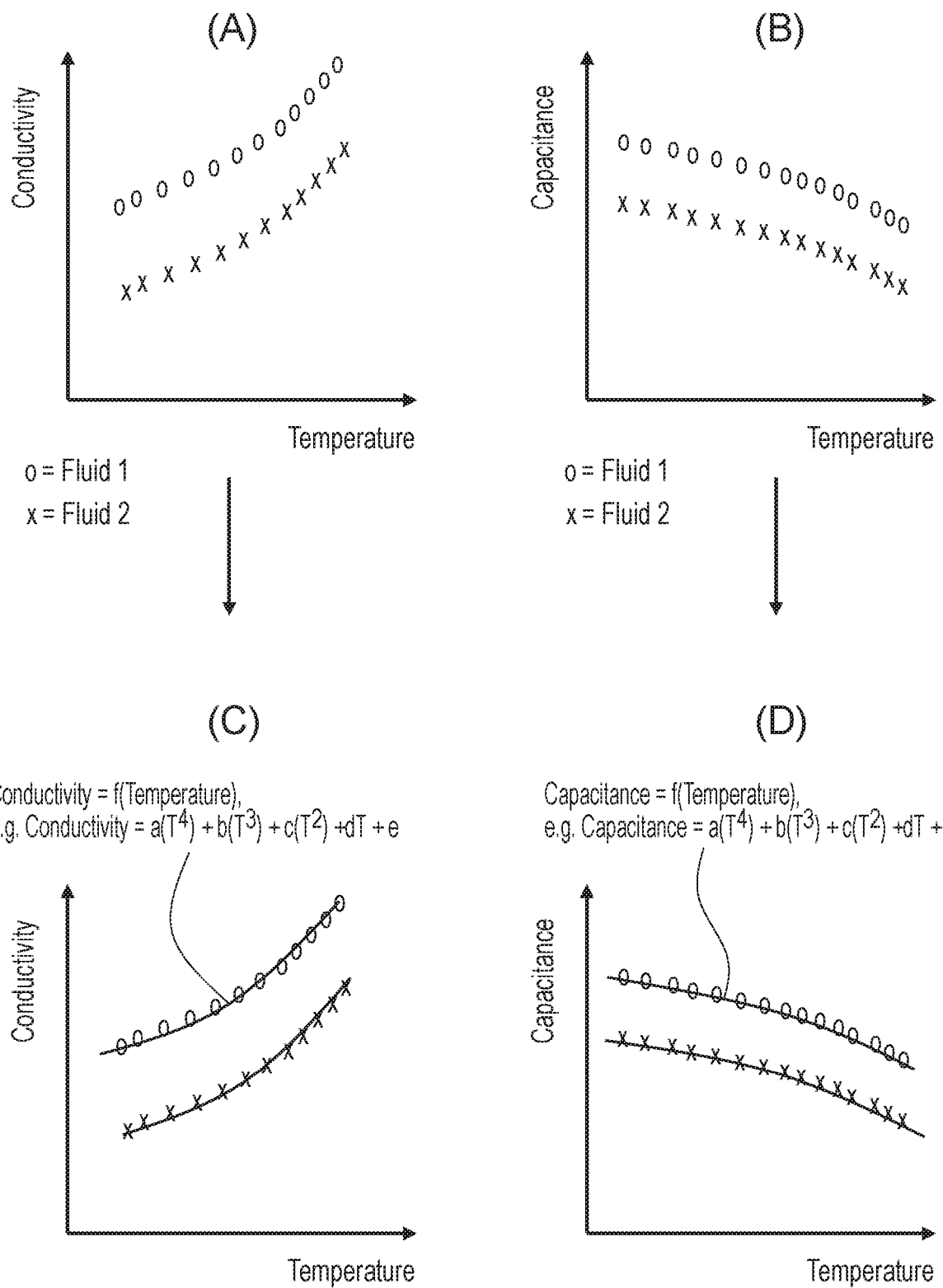
FIG. 25 shows data acquired for a plurality of reference fluids.

An overview of the technology will be given before describing how to acquire data about reference fluid(s) and how to compare a fluid against stored data for the reference fluid(s). FIG. 25 shows a set of data acquired for two reference fluids: Fluid 1, Fluid 2. Data for conductivity against temperature is presented as a first graph A. Data for capacitance against temperature is presented as a second graph B. It can be seen that conductivity and capacitance varies with temperature. The response of each fluid is different. Data for a larger number of fluids can be acquired in this way. This data can be acquired from measurements performed on samples of the reference fluids. A process and apparatus for acquiring the data is described below.

Optionally, the data set shown in graph A can be approximated by a mathematical function in the form of a function of which expresses conductivity as a function of temperature. This is shown in graph C. An example quartic function (i.e. a polynomial of degree four) has the generalised form:

$$\text{Conductivity} = a(T^4) + b(T^3) + c(T^2) + dT + e$$

where: T is temperature; and a, b, c, d, e are coefficients.

The data set for each fluid is represented by a separate mathematical function.

Similarly, the data set shown in graph B can be approximated by a mathematical function in the form of a function of which expresses capacitance as a function of temperature. This is shown in graph D. An example quartic function (i.e. a polynomial of degree four) has the generalised form:

$$\text{Capacitance} = f(T^4) + g(T^3) + h(T^2) + iT + j$$

where: T is temperature; and f, g, h, i, j are coefficients.

The data set for each fluid is represented by a separate mathematical function. The mathematical function may be a polynomial function of any desired power. The mathematical function can be derived in various ways. One suitable method is polynomial regression. Another suitable method is curve fitting. The aim is to find a function which best approximates, or fits, the data set.

An alternative to finding functions which approximate the data is to store the actual set of data values which relate conductivity and temperature and to store the actual set of data values which relate capacitance and temperature.

Figure 26:
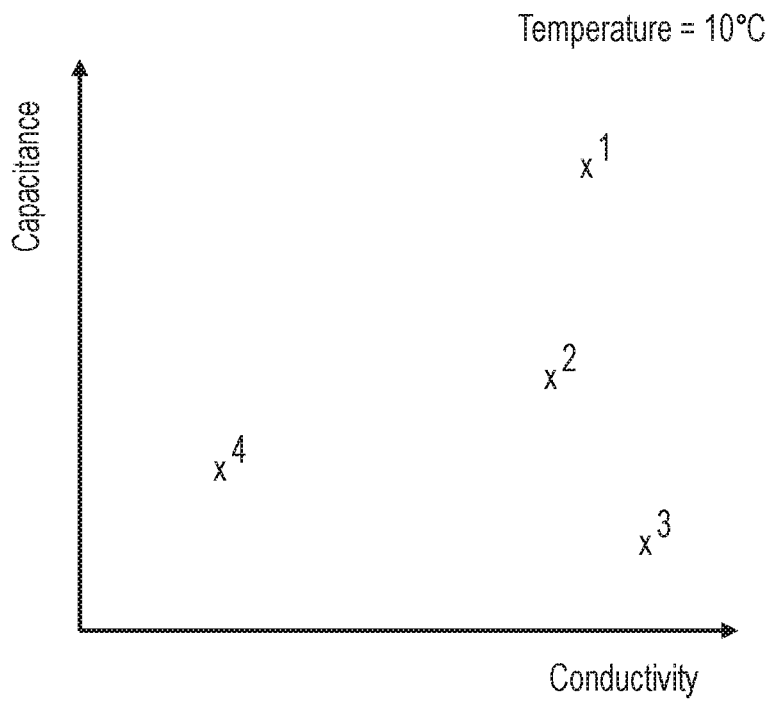
FIG. 26 shows capacitance and conductivity values for each of a plurality of reference fluids at a particular temperature.

FIG. 26 shows a plot of capacitance and conductivity values for four example reference fluids 1-4 at a particular temperature. Each fluid has a different "fingerprint" in terms of an expected value of capacitance and an expected value of conductivity. This pair of capacitance and conductivity values can be considered as a position in a two-dimensional space, where the dimensions are capacitance and conductivity. The fluid under test will also have a fingerprint in terms of a measured value of capacitance and a measured value of conductivity. This can also be considered as a position in the same two-dimensional space. This "fingerprint" can be used to identify the fluid under test. Note that, at a different temperature, the position of the fingerprint (in the 2D capacitance-conductivity space) may be different for one or more of the fluids. In FIG. 25 the conductivity and capacitance vary with temperature so the position of the fingerprint in the two-dimensional space will vary with temperature. In the case of fluids in the form of beverages, conductivity varies with dissolved salts and ions and capacitance varies with the dielectric permittivity of ingredients and emulsified particles. These may include water, alcohol and other electrically polarisable substances or particles in the fluid.

Figure 27:
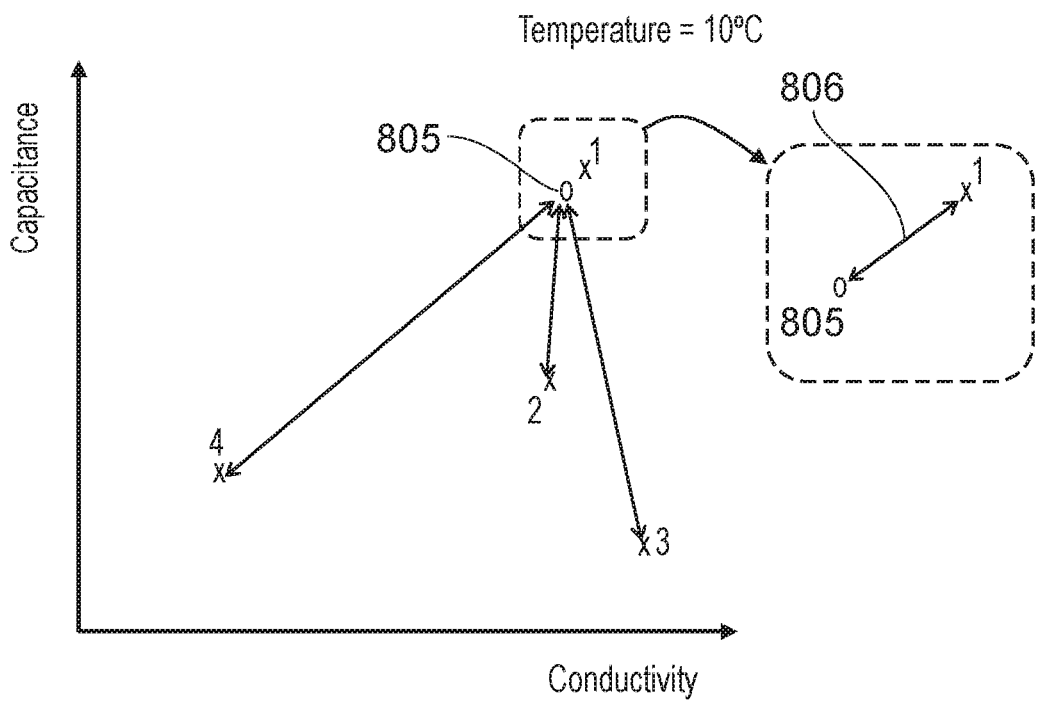
FIG. 27 shows comparison of a capacitance value and a conductivity value for a fluid under test with the reference fluid data of FIG. 26.

FIG. 27 shows measured values of capacitance and conductivity of a fluid under test plotted as a point 805 on the same 2D capacitance-conductivity space. A distance between: (i) the point 805 representing the measured values of capacitance and conductivity of the fluid under test; and (ii) the points 1-4 representing the measured values of capacitance and conductivity of the reference fluids represents the similarity between the fluid under test and the reference fluids. A distance can be computed for each of the points 1-4. That is: a distance between point 805 and point 1; a distance between point 805 and point 2; and so on for each of the reference fluids. In this example, there is a close match between the fluid under test and Fluid 1. A Euclidean distance 806 is shown between the points representing the fluid under test and Fluid 1. The Euclidean distance represents the shortest distance between the two points. Other metrics/measures may be used to determine the best match between the fluid under test and the reference fluids. It will be understood that the distance will vary according to the scale applied to each dimension.

Figure 28:
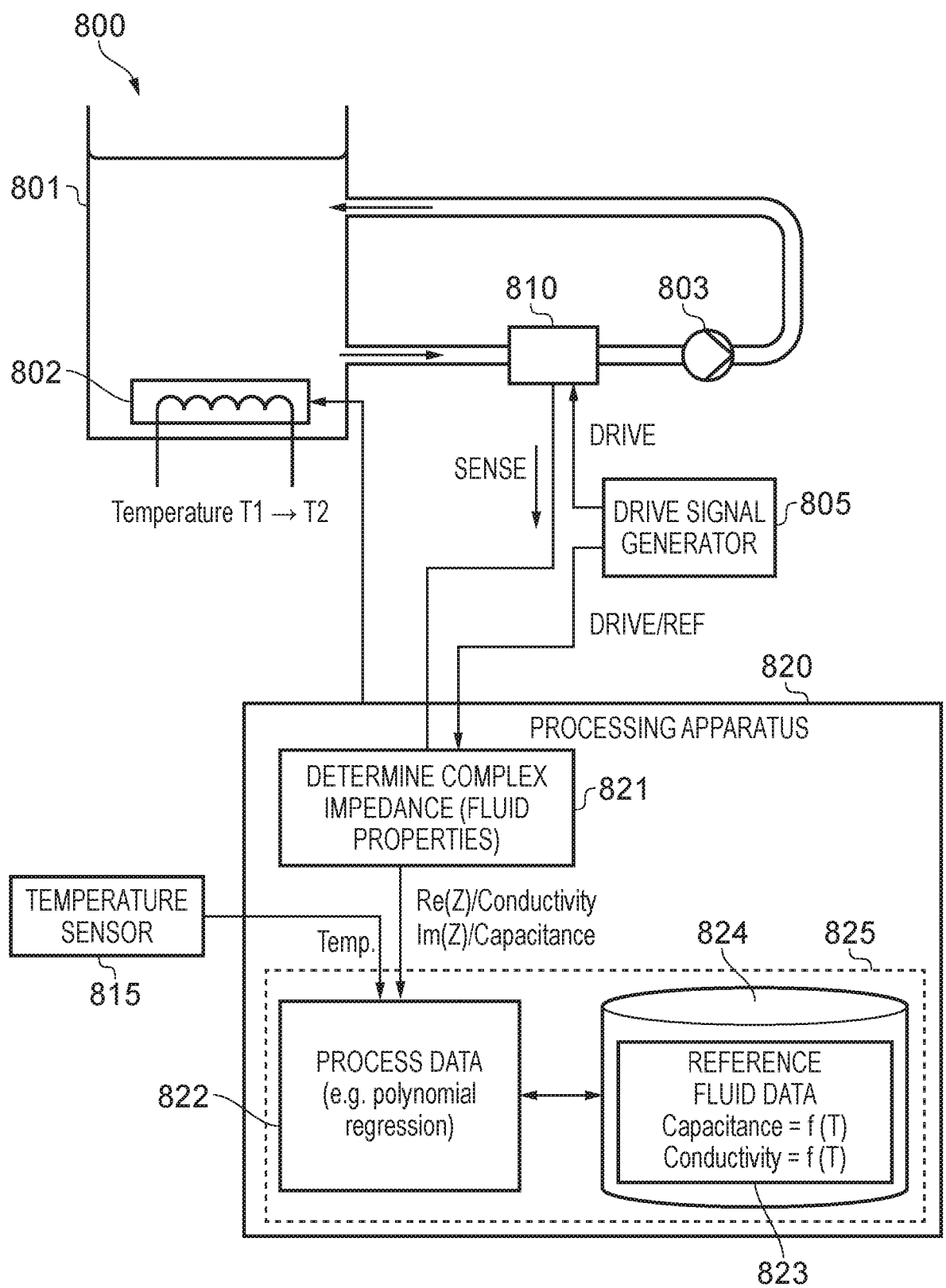
FIG. 28 shows an example of apparatus for acquiring data about a reference fluid.

FIG. 28 shows an example of apparatus 800 to acquire data about a reference fluid. In this example the fluid is a liquid. A tank 801 holds a quantity of the fluid to be measured. A heater 802, such an electrical heater, is configured to heat the fluid. The heater 802 is shown positioned within the tank 801. Temperature of the heater 802 may be controlled by processing apparatus 820, or a different processing apparatus. A conduit connects the tank 801 to a fluid sensor 810. A pump 803 causes fluid to flow along the conduit and then back to the tank 801. A temperature sensor 815 may be co-located with the fluid sensor 810, or at some other position within the overall apparatus. The temperature sensor may be located within the fluid flow path, or may monitor a wall of the conduit. In use, the fluid sensor 810 obtains measurements of the fluid as it flows along the conduit. Fluid sensor 810 may be the same as, or similar to, the fluid sensor cell 110 described previously. Similar to the apparatus shown in FIG. 1 and FIG. 2, a drive signal generator 805 is configured to output an alternating drive signal DRIVE to the fluid sensor 810. Processing apparatus 820 may be similar to the processing apparatus 130 described previously. Processing apparatus 820 receives an alternating sense signal SENSE from the fluid sensor 810. Processing apparatus 820 receives the alternating drive signal DRIVE or a reference signal REF which is derived from the drive signal (e.g. see FIG. 2). Processing apparatus 820 may determine a measured value indicative of a conductivity quantity of the fluid based on the sense signal from the fluid sensor 810 and the drive signal (DRIVE/REF). Processing apparatus 820 may determine a measured value indicative of a capacitance quantity of the fluid under test based on a sense signal from the fluid sensor and a drive signal applied to the fluid sensor. Functional block 821 is configured to determine properties of the fluid under test, i.e. a measured value indicative of a conductivity quantity of the fluid under test and a measured value indicative of a capacitance quantity of the fluid sensor. Block 821 may determine a complex impedance of the fluid sensor in a similar way as described previously. A first output of block 821 may be a real (in-phase) component which is indicative of conductivity of the fluid under test or a conductivity derived from the real (in-phase) component. A second output of block 821 may be an imaginary (quadrature) component which is indicative of capacitance of the fluid sensor, or a capacitance or dielectric constant/relative permittivity derived from the imaginary (quadrature) component. Measurements are obtained at a range of temperatures. For example, over a range of temperatures from a lower temperature T1 to a higher temperature T2. Processing apparatus 820 also receives a temperature from temperature sensor 815.

Functional block 822 is configured to process the measured data. Block 822 may perform polynomial regression, or some other process, to obtain a function expressing capacitance as a function of temperature and a function expressing conductivity as a function of temperature. Data 823 about the fluid is stored in a data store 824. The stored data 823 may be: a function expressing capacitance as a function of temperature and a function expressing conductivity as a function of temperature; or a data set for capacitance versus temperature and a data set for conductivity versus temperature. The apparatus shown in FIG. 28 is used to acquire measurement data for each of the reference fluids.

The processing apparatus 820 may be a single processing apparatus, or multiple processing apparatuses. For example, a first processing apparatus may determine the measured values and a second processing apparatus 825 may process the measured data to obtain the reference fluid data. For example, the first processing apparatus may be co-located with the fluid sensor and the second processing apparatus may be located separately or remotely from the fluid sensor, such a server or cloud-based processing apparatus. This can simplify processing apparatus required at, or near, the fluid sensor.

Figure 29:
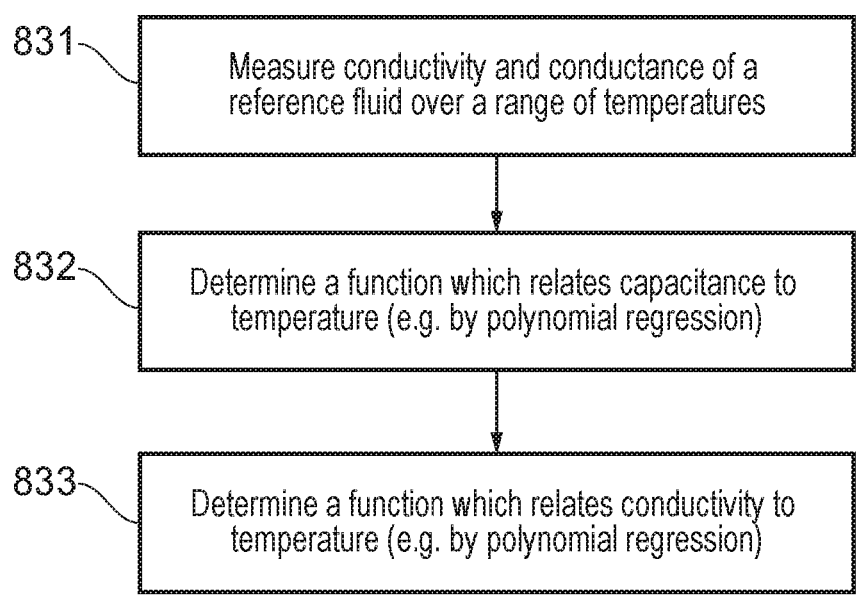
FIG. 29 is a flow diagram of a method for acquiring data about a reference fluid.

FIG. 29 shows an example of a method which can be performed by the processing apparatus 820. At block 831 the method measures values indicative of a conductance quantity and of a capacitance quantity over a range of temperatures. Optionally, at block 832 the method determines data relating the capacitance quantity to temperature. Optionally, at block 833 the method determines a function which relates the conductivity quantity to temperature (e.g. by polynomial regression).

Figure 30:
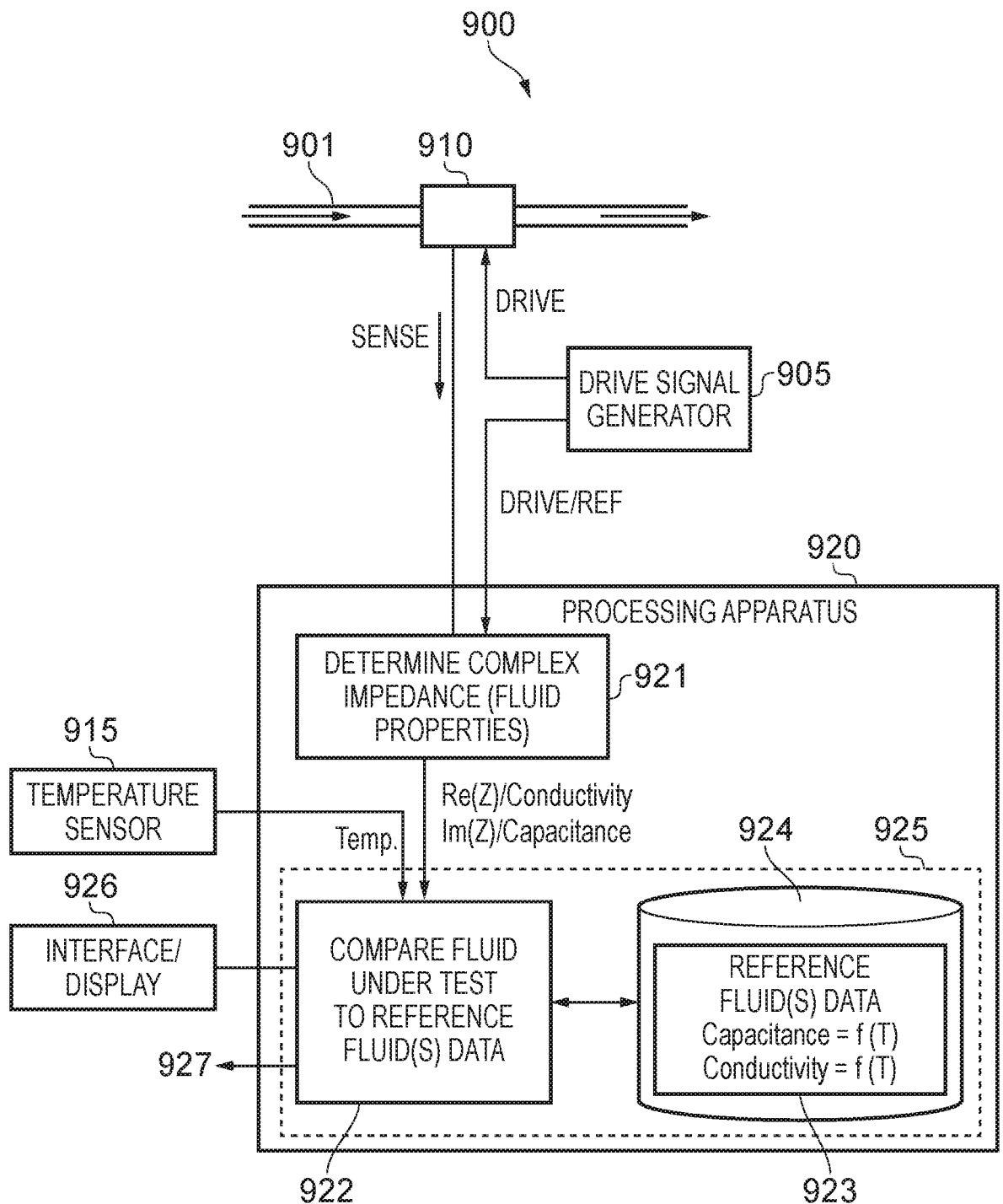
FIG. 30 shows an example of apparatus for measuring a property of a fluid under test.

FIG. 30 shows an example of apparatus 900 to acquire data about a fluid under test. A fluid sensor 910 is connected to a fluid-carrying conduit 901. In use, the fluid sensor 910 obtains measurements of the fluid as it flows along the conduit 901. Fluid sensor 910 may be the same as, or similar to, the fluid sensor cell 110, 810 described previously. Similar to the apparatus shown in FIG. 1 and FIG. 2, a drive signal generator 905 is configured to output an alternating drive signal DRIVE to the fluid sensor 810. Processing apparatus 920 may be similar to the processing apparatus 130, 820 described previously. Processing apparatus 920 receives an alternating sense signal SENSE from the fluid sensor 910. Processing apparatus 920 receives the alternating drive signal DRIVE or a reference signal which is derived from the drive signal. Processing apparatus 920 may determine a measured value indicative of a conductivity quantity of the fluid based on the sense signal from the fluid sensor 910 and the drive signal (DRIVE/REF). Processing apparatus 920 may determine a measured value indicative of a conductivity quantity of the fluid based on a sense signal from the fluid sensor and a drive signal applied to the fluid sensor. Processing apparatus 920 may determine a measured value indicative of a capacitance quantity of the fluid under test based on a sense signal from the fluid sensor and a drive signal applied to the fluid sensor. Functional block 921 is configured to determine properties of the fluid under test, i.e. a measured value indicative of a conductivity quantity of the fluid under test and a measured value indicative of a capacitance quantity of the fluid sensor. A first output of block 921 may be a real (in-phase) component which is indicative of conductivity of the fluid under test or a conductivity derived from the real (in-phase) component. A second output of block 921 may be an imaginary (quadrature) component which is indicative of capacitance of the fluid sensor, or a capacitance or dielectric constant/relative permittivity derived from the imaginary (quadrature) component. Functional block 922 is configured to compare the fluid under test with reference fluid(s) and identify a best match. Block 922 is configured to use stored data 923 about a reference fluid, or a plurality of reference fluids, stored in a data store 924. The stored data 923 may be: a function expressing capacitance as a function of temperature and a function expressing conductivity as a function of temperature; or a data set for capacitance versus temperature and a data set for conductivity versus temperature. A temperature sensor 915 may be co-located with the fluid sensor 910. One possibility for the temperature sensor is an infra-red (IR) temperature sensor which measures a surface temperature of an outside wall of the sensor cell (611, FIG. 14) in a non-contact manner. Another possibility is a temperature sensor which is in contact with the sensor cell, or within the fluid channel of the sensor cell, e.g. a thermocouple, a thermistor, or a resistance temperature detector (RTD).

The processing apparatus may be connected to an interface and/or a display 926 to provide an indication of which reference fluid matches the fluid under test. The processing apparatus may provide an output signal 927 to control an external apparatus, or to communicate with an external apparatus (e.g. a control system of a processing plant).

The processing apparatus 920 may be a single processing apparatus, or multiple processing apparatuses. For example, a first processing apparatus may determine the measured values and a second processing apparatus 925 may compare the fluid under test to one or more of the reference fluid(s). For example, the first processing apparatus may be co-located with the fluid sensor and the second processing apparatus may be located separately or remotely from the fluid sensor, such as a server or cloud-based processing apparatus. This can allow easier updating of the reference fluid data and simplify processing apparatus required at the fluid sensor.

Figure 31:
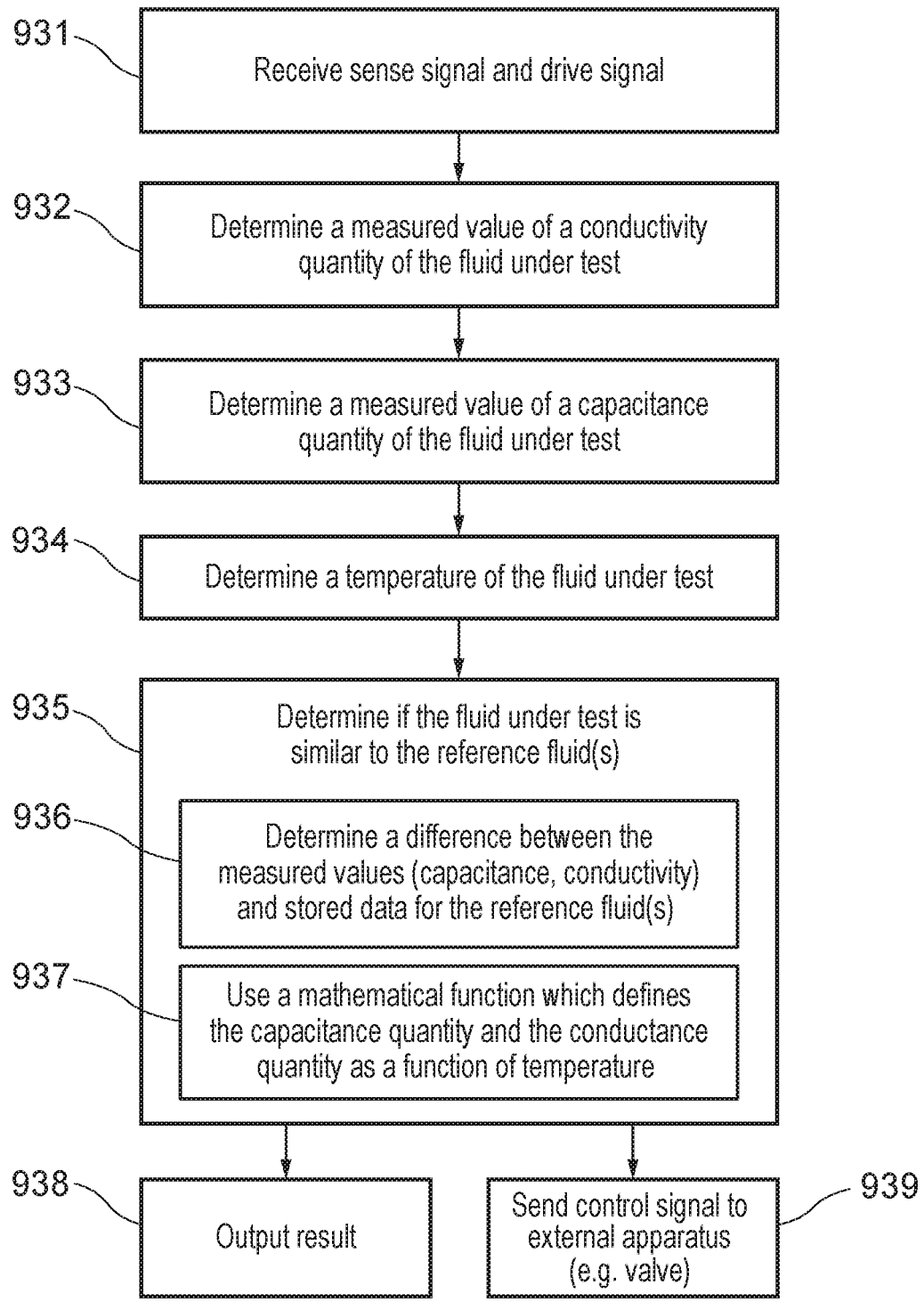
FIG. 31 is a flow diagram of a method for measuring a property of a fluid under test.

FIG. 31 shows an example of a method which can be performed by the processing apparatus 920. At block 931 the method receives a sense signal from the fluid sensor and a drive signal. Block 932 determines a measured value of a conductivity quantity of the fluid under test. Block 933 determines a measured value of a capacitance quantity of the fluid sensor. Block 934 determines a temperature of the fluid under test. Block 935 determines if the fluid under test is similar to the reference fluid(s). The functions are similar to what have already been described for FIG. 26 and FIG. 27. Block 936 determines a difference between the measured values (capacitance, conductivity) and stored data for the reference fluid(s). As a preliminary step, the method may determine expected values for the capacitance and conductivity at the measured temperature. A first possible way of determining the expected values is by using the stored mathematical function which expresses capacitance as a function of temperature and the stored mathematical function which expresses conductivity as a function of temperature. The functions are computed using the measured temperature value. A second possible way of determining the expected values is by using the stored set of actual data which relates capacitance and conductivity to temperature. An expected value of capacitance and conductivity is obtained by performing a look up operation (using the measured value of temperature) in the set of data, or by interpolating between values in the set of data values. As described with reference to FIG. 27, determining if the fluid under test is similar to the reference fluid(s) may compute a Euclidean distance between the capacitance and conductivity of the fluid under test with the expected values of capacitance and conductivity for each of the reference fluids.

There are various possible actions after determining a closest match to the fluid. One possible next step is shown at block 938. An indication of which reference fluid matches the fluid under test can be reported to a user via a digital interface or a display, or sent via a communications link or network to a remote device. Additionally, or alternatively, a control signal may be output to an external apparatus. For example, a valve may be opened if a match is found with an expected fluid (block 939).

It is possible that the fluid under test is not a good match to any of the reference fluids. Block 935 may use a threshold value (such as a threshold value of Euclidean distance) to determine when a fluid under test is a match. If the difference (or differences) determined at block 936 exceed the threshold value, then block 935 may determine that the fluid under test is not a good match to any of the reference fluids. This can be reported to a user (block 938) and a suitable control signal can be sent, such as a control signal to close a valve.

Measuring a Fluid Property Independently of Temperature

As explained above, a value of a measured quantity can vary with temperature. One way of addressing this issue is to measure temperature and then adjust a measured property of the fluid based on the measured temperature. However, it is more desirable to measure a property of a fluid without a need to measure temperature.

Figure 32:
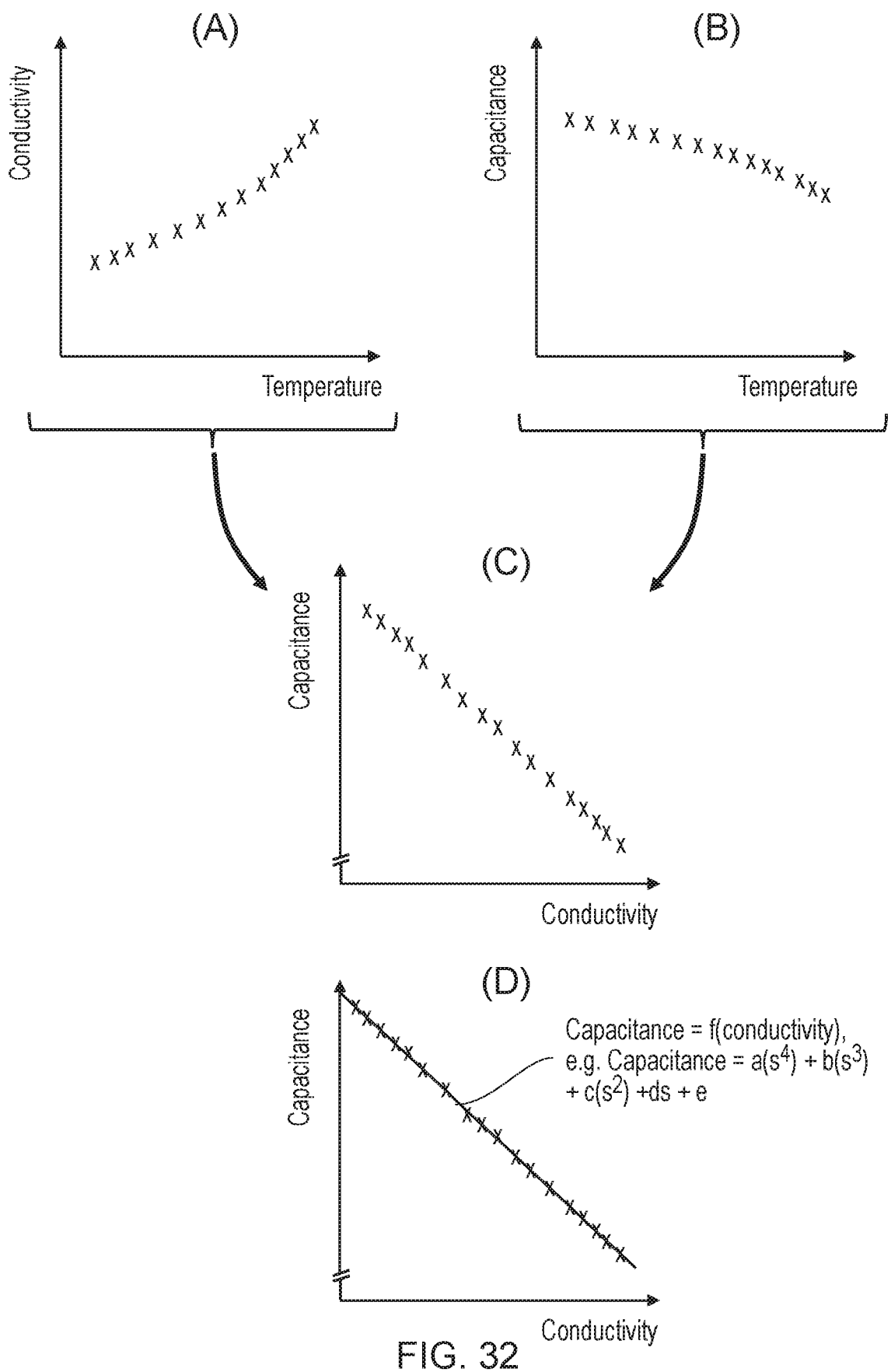
FIG. 32 shows data acquired for a reference fluid.

An overview of the technology will be given before describing how to acquire the reference fluid data and how to test a fluid against the reference fluid data. FIG. 32 shows a set of data for conductivity against temperature, presented as a first graph A. FIG. 32 also shows a set of data for capacitance against temperature, presented as a second graph B. This data can be acquired from measurements performed on a reference fluid. A process and apparatus for acquiring the data is described below. These two separate sets of data can be combined into a single set of data which relates capacitance to conductivity. For any temperature shown in both graph A and B, there is a corresponding value of conductivity (graph A) and a corresponding value of capacitance (graph B). For example, if the conductivity at temperature T1 is Cond_1 and the capacitance at temperature T1 is Cap_1, then conductivity value Cond_1 maps to capacitance Cap_1. Graph C shows a graph relating capacitance to conductivity. Graph C shows the expected relationship between capacitance and conductivity for the reference fluid, independently of temperature. For any value of conductivity in the range covered by the data set, it is possible to find a corresponding value of capacitance. Similarly, for any value of capacitance in the range covered by the data set, it is possible to find a corresponding value of conductivity. Graph D relates capacitance to conductivity without the need to measure, or compensate for, temperature. Graph C represents the expected relationship between capacitance and conductance for the reference fluid.

Optionally, the data set shown in graph C can be approximated by a mathematical function in the form of a function of which expresses capacitance as a function of conductivity. This is shown in D. An example quartic function (i.e. a polynomial of degree four) has the generalised form:

$$Capacitance = a(s^4) + b(s^3) + c(s^2) + ds + e$$

where: s is conductivity; and a, b, c, d, e are coefficients.

The mathematical function may be a polynomial function of any desired power. The mathematical function can be derived in various ways. One suitable method is polynomial regression. Another suitable method is curve fitting. The aim is to find a function which best approximates, or fits, the data set. An advantage of approximating the relationship between capacitance and conductivity as a mathematical function is reduced data storage requirements. To obtain an expected value of capacitance, it is only necessary to store the mathematical function. The expected value of capacitance is obtained by computing the function with the quantity "s" equal to a measured value of conductivity.

An alternative method is to store the actual set of data which relates capacitance and conductivity. An expected value of capacitance is obtained by performing a look up operation (using a measured value of conductivity) in the set of data. Typically, a required value will not equal one of the stored values of conductivity. Therefore, it is possible to interpolate between stored values of conductivity to find a required value of capacitance. Similarly, an expected value of conductivity is obtained by performing a look up operation (using a measured value of capacitance) in the set of data, or by interpolating between stored values of conductivity.

The mathematical function described above expresses capacitance as a function of conductivity. As an alternative, it is possible to derive a mathematical function which expresses conductivity as a function of capacitance. An example quartic function (i.e. a polynomial of degree four) has the generalised form:

$$Conductivity = f(z^4) + g(z^3) + h(z^2) + iz + j$$

where: z is capacitance; and f, g, h, i, j are coefficients.

The mathematical function may be a polynomial function of any desired power. The mathematical function can be derived in various ways. To obtain an expected value of conductivity, it is only necessary to store the mathematical function. The expected value of conductivity is obtained by computing the function with a measured value of capacitance.

The data relating capacitance to conductivity can subsequently be used when measuring a fluid under test. One of the measured values (i.e. the measured value indicative of the capacitance quantity or the measured value indicative of the conductance quantity) is used to find the expected value of the corresponding quantity. If the measured value is indicative of the conductance quantity, then this is used to find the expected value of the capacitance quantity. Any difference between the expected value and the measured value of the capacitance quantity indicates a deviation from the expected value of the capacitance quantity of the reference fluid. Similarly, if the measured value is indicative of the capacitance quantity, then this is used to find the expected value of the conductance quantity. Any difference between the expected value and the measured value of the conductance quantity indicates a deviation from the expected value of the conductance quantity of the reference fluid.

Figure 33:
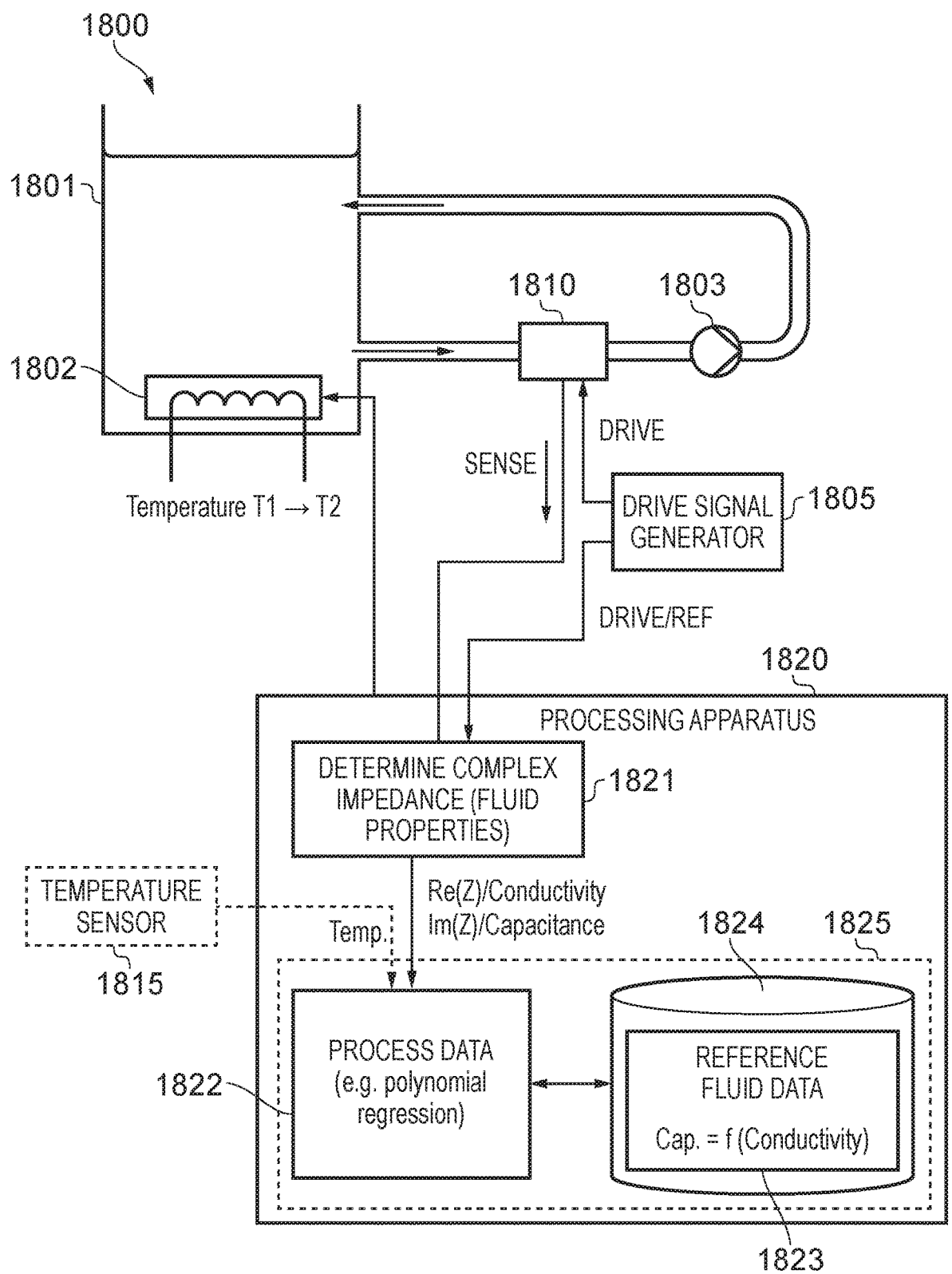
FIG. 33 shows an example of apparatus for acquiring data about a reference fluid.

FIG. 33 shows an example of apparatus 1800 to acquire data about a reference fluid. In this example the fluid is a liquid. A tank 1801 holds a quantity of the fluid to be measured. A heater 802, such an electrical heater, is configured to heat the fluid. The heater 1802 is shown positioned within the tank 1801. Temperature of the heater 802 may be controlled by processing apparatus 1820, or a different processing apparatus. A conduit connects the tank 1801 to a fluid sensor 1810. A pump 1803 causes fluid to flow along the conduit and then back to the tank 1801. A temperature sensor 1815 may be co-located with the fluid sensor 1810, or at some other position within the overall apparatus. The temperature sensor may be located within the fluid flow path, or may monitor a wall of the conduit. In use, the fluid sensor 1810 obtains measurements of the fluid as it flows along the conduit. Fluid sensor 1810 may be the same as, or similar to, the fluid sensor cell 110 described previously. Similar to the apparatus shown in FIG. 1 and FIG. 2, a drive signal generator 805 is configured to output an alternating drive signal DRIVE to the fluid sensor 1810. Processing apparatus 1820 may be similar to the processing apparatus 130 described previously. Processing apparatus 1820 receives an alternating sense signal SENSE from the fluid sensor 1810. Processing apparatus 1820 receives the alternating drive signal DRIVE or a reference signal which is derived from the drive signal. Processing apparatus 1820 may determine a measured value indicative of a conductivity quantity of the fluid based on the sense signal from the fluid sensor 1810 and the drive signal (DRIVE/REF). Processing apparatus 1820 may determine a measured value indicative of a conductivity quantity of the fluid based on a sense signal from the fluid sensor 1810 and a drive signal applied to the fluid sensor. Processing apparatus 1820 may determine a measured value indicative of a capacitance quantity of the fluid under test based on a sense signal from the fluid sensor and a drive signal applied to the fluid sensor. Functional block 1821 is configured to determine properties of the fluid under test, i.e. a measured value indicative of a conductivity quantity of the fluid under test and a measured value indicative of a capacitance quantity of the fluid sensor. A first output of block 1821 may be an in-phase component which is indicative of conductivity of the fluid under test or a conductivity derived from the in-phase component. A second output of block 1821 may be a quadrature component which is indicative of capacitance of the fluid sensor, or a capacitance or dielectric constant/relative permittivity derived from the quadrature component. Measurements are obtained at a range of temperatures. For example, over a range of temperatures from a lower temperature T1 to a higher temperature T2. Processing apparatus 1820 also receives a temperature from temperature sensor 1815. Functional block 1822 is configured to process the measured data. Block 1822 may perform polynomial regression, or some other process, to obtain a function expressing capacitance as a function of conductivity, or a function expressing conductivity as a function of capacitance. Data 1823 about the fluid is stored in a data store 1824. The stored data 1823 may be: a function expressing capacitance as a function of conductivity; a function expressing conductivity as a function of capacitance; or a data set relating capacitance to conductivity.

The processing apparatus 1820 may be a single processing apparatus, or multiple processing apparatuses. For example, a first processing apparatus may determine the measured values and a second processing apparatus 1825 may process the measured data to obtain the reference fluid data. For example, the first processing apparatus may be co-located with the fluid sensor and the second processing apparatus may be located separately or remotely from the fluid sensor, such as a server or cloud-based processing apparatus. This can simplify processing apparatus required at, or near, the fluid sensor.

Figure 34:
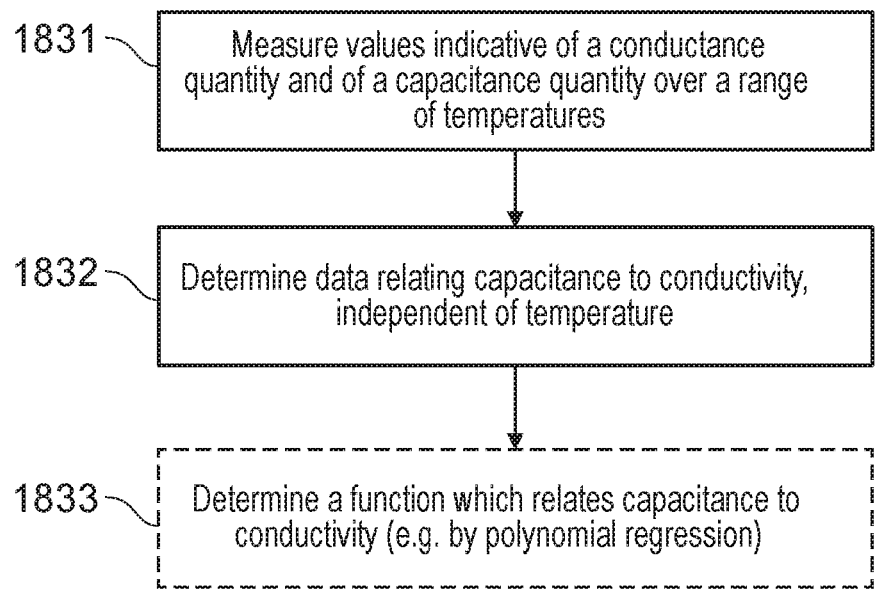
FIG. 34 is a flow diagram of a method for acquiring data about a reference fluid.

FIG. 34 shows an example of a method which can be performed by the processing apparatus 1820. At block 1831 the method measures values indicative of a conductance quantity and of a capacitance quantity over a range of temperatures. At block 1832 the method determines data relating the capacitance quantity to the conductivity quantity, independently of temperature. Optionally, at block 1833 the method determines a function which relates the capacitance quantity to the conductivity quantity (e.g. by polynomial regression).

It will be understood that temperature is measured when acquiring the reference data. During subsequent measurements of a fluid under test, temperature does not have to be measured.

Figure 35:
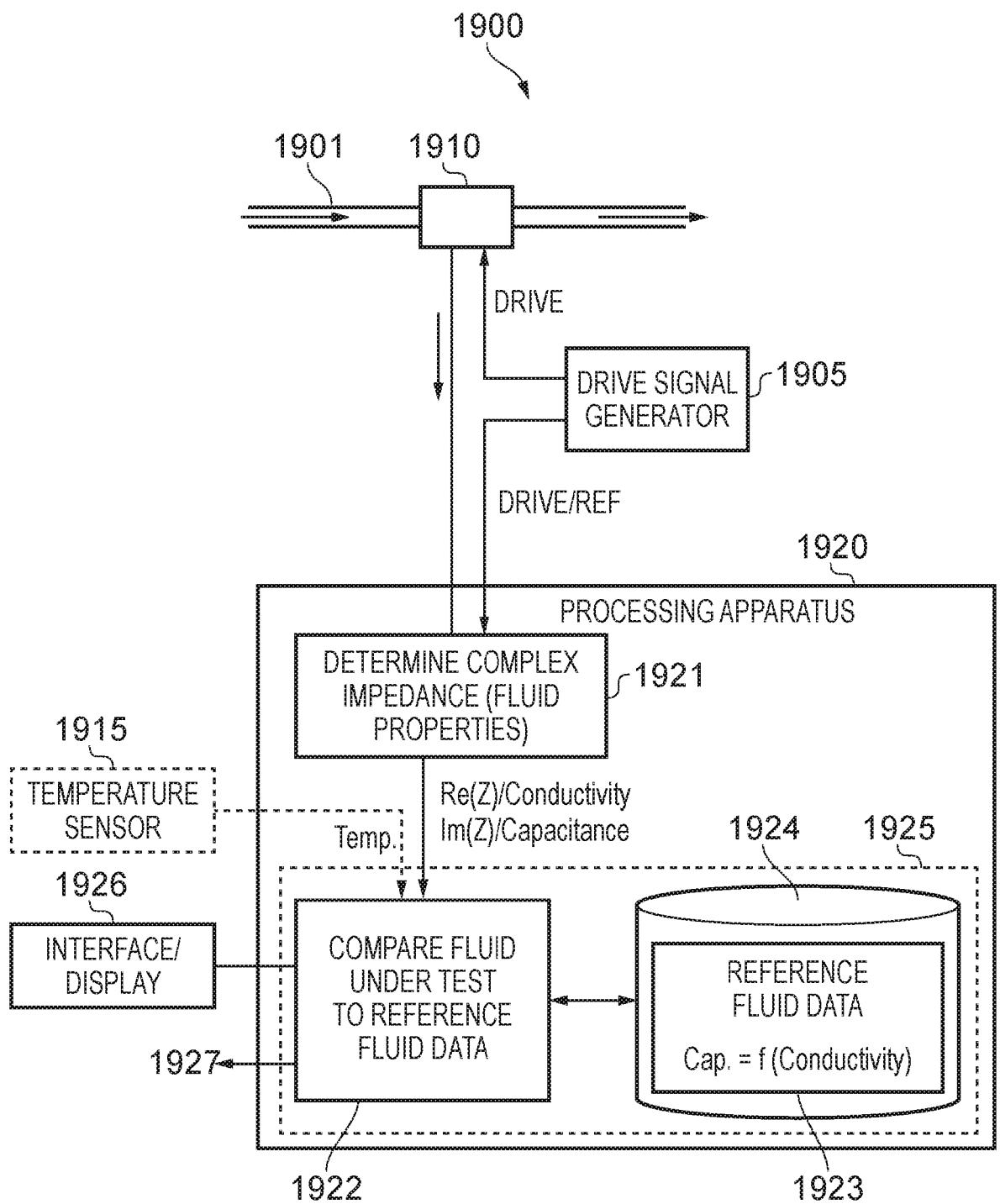
FIG. 35 shows an example of apparatus for measuring a property of a fluid under test.

FIG. 35 shows an example of apparatus 1900 to acquire data about a fluid under test. A fluid sensor 1910 is connected to a fluid-carrying conduit 1901. In use, the fluid sensor 1910 obtains measurements of the fluid as it flows along the conduit 1901. Fluid sensor 1910 may be the same as, or similar to, the fluid sensor cell 110, 1810 described previously. Similar to the apparatus shown in FIG. 1 and FIG. 2, a drive signal generator 1905 is configured to output an alternating drive signal DRIVE to the fluid sensor 810. Processing apparatus 1920 may be similar to the processing apparatus 130, 1820 described previously. Processing apparatus 1920 receives an alternating sense signal SENSE from the fluid sensor 1910. Processing apparatus 1920 receives the alternating drive signal DRIVE or a reference signal which is derived from the drive signal. Processing apparatus 1920 may determine a measured value indicative of a conductivity quantity of the fluid based on the sense signal from the fluid sensor 1910 and the drive signal (DRIVE/REF). Processing apparatus 1920 may determine a measured value indicative of a capacitance quantity of the fluid under test based on a sense signal from the fluid sensor and a drive signal applied to the fluid sensor. Functional block 1921 is configured to determine properties of the fluid under test, i.e. a measured value indicative of a conductivity quantity of the fluid under test and a measured value indicative of a capacitance quantity of the fluid under test. A first output of block 1921 may be a real (in-phase) component which is indicative of conductivity of the fluid under test or a conductivity derived from the real (in-phase) component. A second output of block 1921 may be an imaginary (quadrature) component which is indicative of capacitance of the fluid sensor, or a capacitance or dielectric constant/relative permittivity derived from the imaginary (quadrature) component. Functional block 1922 is configured to compare the fluid under test with the reference fluid data. Block 1922 is configured to use stored data 1923 about a reference fluid stored in a data store 1924. The stored data 1923 may be: a function expressing capacitance as a function of conductivity; a function expressing conductivity as a function of capacitance; or a data set relating capacitance to conductivity. The processing apparatus may be connected to an interface and/or a display 1926 to provide an indication of which reference fluid matches the fluid under test. The processing apparatus may provide an output signal 1927 to control an external apparatus, or to communicate with an external apparatus (e.g. a control system of a processing plant). Optionally, a temperature sensor 1915 may be co-located with the fluid sensor 1910. A temperature sensor 1915 is not required for normal operation, but it could be used to check accuracy of the fluid sensor 1910 and/or check that the processing apparatus 1920 is operating correctly.

The processing apparatus 1920 may be a single processing apparatus, or multiple processing apparatuses. For example, a first processing apparatus may determine the measured values and a second processing apparatus 1925 may compare the fluid under test to the reference fluid data. For example, the first processing apparatus may be co-located with the fluid sensor and the second processing apparatus may be located separately or remotely from the fluid sensor, such as a server or cloud-based processing apparatus. This can allow easier updating of the reference fluid data and simplify processing apparatus required at the fluid sensor.

Figure 36:
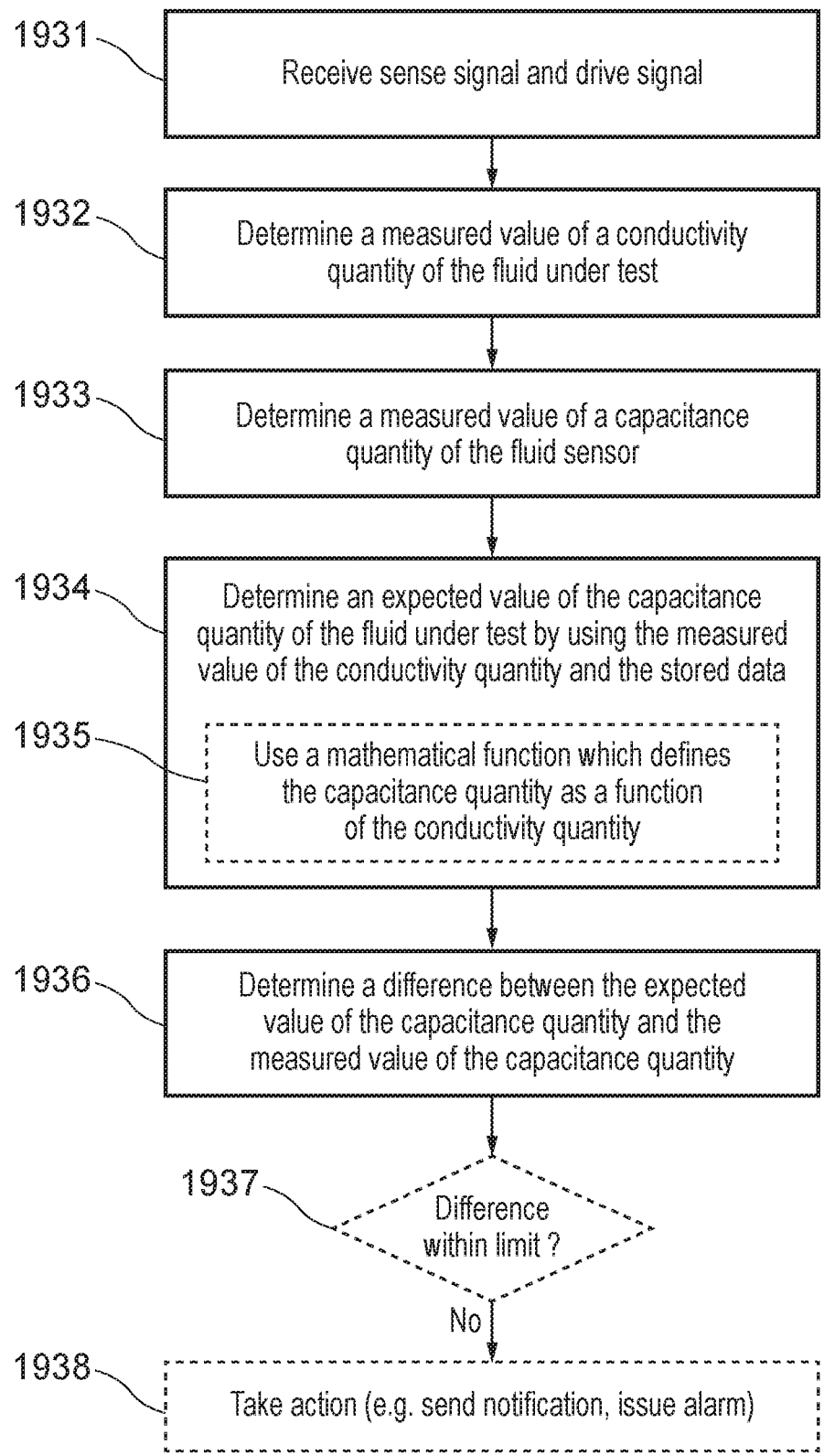
FIG. 36 is a flow diagram of a method for measuring a property of a fluid under test.

FIG. 36 shows an example of a method which can be performed by the processing apparatus 1920. At block 1931 the method receives a sense signal from the fluid sensor and a drive signal. Block 1932 determines a measured value of a conductivity quantity of the fluid under test. Block 1933 determines a measured value of a capacitance quantity of the fluid sensor. Block 1934 determines an expected value of the capacitance quantity of the fluid under test by using the measured value of the conductivity quantity and the stored data. Block 1934 may use a mathematical function which defines the capacitance quantity as a function of the conductivity quantity (or a mathematical function which defines the conductivity quantity as a function of the capacitance quantity), as shown by optional block 1935. Alternatively, block 1934 may use a stored set of actual data which relates capacitance and conductivity. An expected value of capacitance is obtained by performing a look up operation (using a measured value of conductivity) in the set of data, or by interpolating between values in the set of data values. Block 1936 determines a difference between the expected value of the capacitance quantity and the measured value of the capacitance quantity. This indicates a difference, or a deviation, between the expected value of a property of a fluid and the measured value of that property of the fluid.

There are various possibilities for how to use the output of block 1936. In some applications, there may be a requirement to record values output by block 1936. Outputs values may be recorded continuously or periodically (e.g. at fixed time intervals) regardless of their value. Alternatively, output values may be recorded only when they exceed a threshold value. Block 1937 compares the difference (as determined by block 1936) with a threshold value. In some applications, there may be a requirement to know when a threshold value is exceeded. Block 1938 takes action when a threshold value of difference is exceeded. An example of a possible action is sending a notification (e.g. sending a message to a predetermined destination via a communications link). Another example of a possible action is issuing an alarm, such as a visual alarm and/or an audible alarm. The notification can be reported to a user via a digital interface or a display, or sent via a communications link or network to a remote device. Additionally, or alternatively, a control signal may be output to an external apparatus. For example, a valve may be closed if the difference is greater than the threshold value.

Figure 37:
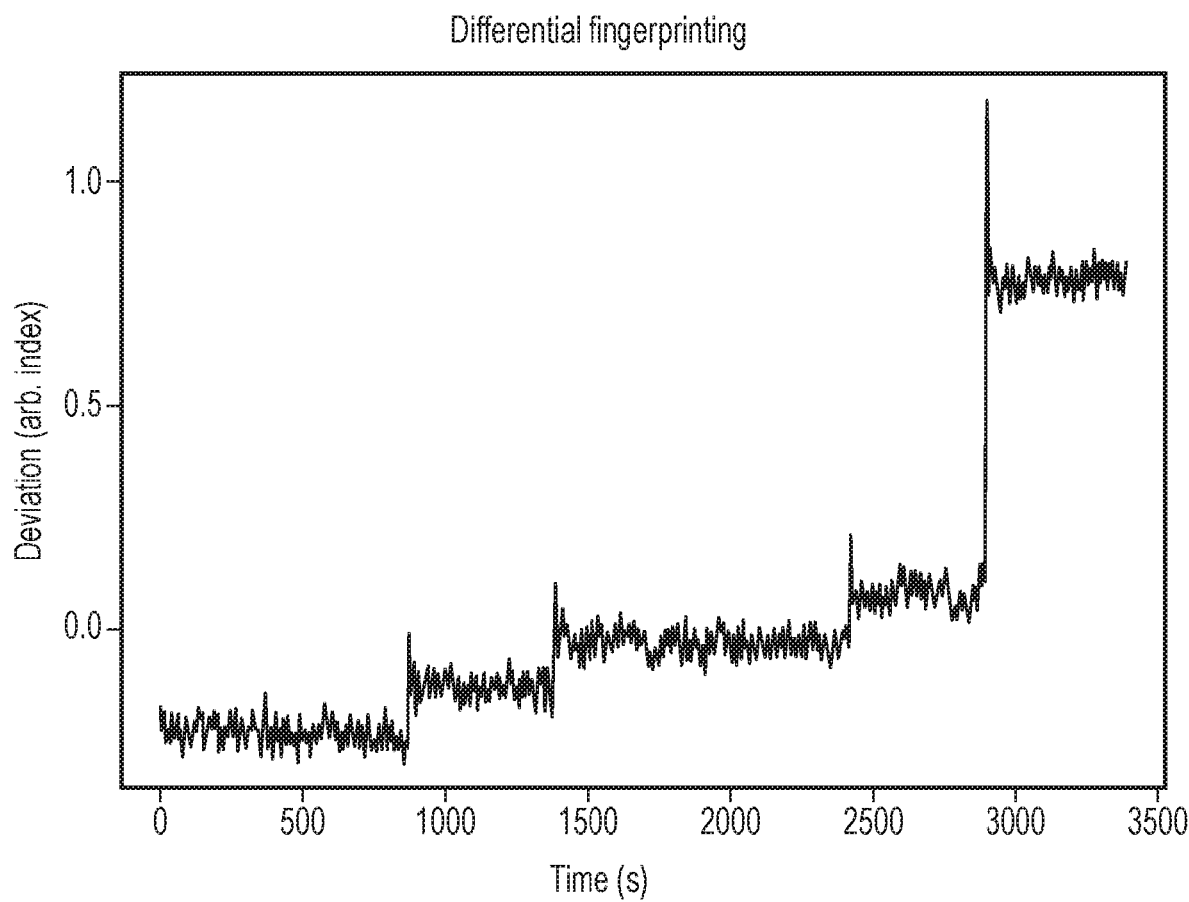
FIG. 37 shows an example of data output during operation of the apparatus of FIG. 35 or the method of FIG. 36.

FIG. 37 shows an example of output data using the method shown in FIG. 36. The trace shown in FIG. 37 is a difference, or a deviation, between the expected value of a property of a fluid and the measured value of that property of the fluid. For example, the difference may represent a deviation in the alcohol content of a beverage measured by the fluid sensor. The method and apparatus may process the output of block 1936 by filtering. The amount of filtering can be tailored to the particular application. For example, some applications may require a quick indication of a deviation. Other applications may permit a (relatively) slower indication of a deviation, which allows a larger degree of filtering/integration on the output of block 1936 and a slower-varying output.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. An apparatus for monitoring a fluid under test, the apparatus comprising:
a processing apparatus comprising a processor and a memory configured to store data indicative of at least one reference fluid, wherein the stored data for the at least one reference fluid comprises data indicative of a capacitance quantity and a conductivity quantity over a range of temperatures, the processing apparatus configured to:
receive a sense signal from a capacitive fluid sensor;
receive an alternating drive/reference signal;
determine a measured value indicative of a conductivity quantity of the fluid under test based on the sense signal and the drive/reference signal;
determine a measured value indicative of a capacitance quantity of the fluid under test based on the sense signal and the drive/reference signal;
determine a measured temperature of the fluid under test;
determine whether the fluid under test is similar to the at least one reference fluid based on:
(i) the measured value indicative of the conductivity quantity, the measured value indicative of the capacitance quantity; and
(ii) the stored data indicative of the conductivity quantity for the at least one reference fluid at the measured temperature and the stored data indicative of the capacitance quantity for the at least one reference fluid at the measured temperature,
wherein the processing apparatus is configured to, for the at least one reference fluid:
determine an expected value of the conductivity quantity for the at least one reference fluid at the measured temperature from the stored data;
determine an expected value of the capacitance quantity for the at least one reference fluid at the measured temperature from the stored data;
determine whether the fluid under test is similar to the at least one reference fluid based on:
(iii) the measured value indicative of the conductivity quantity and the measured value of the capacitance quantity;
(iv) the expected value indicative of the conductivity quantity and the expected value indicative of the capacitance quantity for the at least one reference fluid at the measured temperature, and
wherein the processing apparatus is configured to determine whether the fluid under test is similar to the at least one reference fluid by determining a difference in a two-dimensional space having the capacitance quantity and the conductivity quantity as dimensions between:
(v) a first point representing the measured value indicative of the conductivity quantity and the measured value indicative of the capacitance quantity; and
(vi) at least one second point representing the expected value indicative of the conductivity quantity and the expected value indicative of the capacitance quantity for the at least one reference fluid at the measured temperature.

2. The apparatus according to claim 1 wherein the processing apparatus is configured to determine a Euclidean distance between the first point and the at least one second point.

3. The apparatus according to claim 1 wherein the stored data comprises a set of data values indicative of the capacitance quantity and indicative of the conductivity quantity at different temperatures and the processing apparatus is configured to determine an expected value indicative of the conductivity quantity and to determine an expected value indicative of the capacitance quantity by look up operation in, or by interpolating between, the set of data values indicative of the capacitance quantity and indicative of the conductivity quantity at the measured temperature.

4. The apparatus according to claim 1 wherein the processing apparatus is configured to determine a complex impedance of the fluid sensor based on the sense signal and the drive/reference signal, the complex impedance comprising a real (in-phase) component indicative of the conductivity quantity of the fluid under test and an imaginary (quadrature) component indicative of the capacitance quantity of the fluid under test.

5. The apparatus according to claim 1 further comprising a capacitive fluid sensor having a first electrode and a second electrode with a sensing region between the electrodes.

6. The apparatus according to claim 1 which is also configured to acquire the stored data for the at least one reference fluid,
wherein the processing apparatus is configured to:
(i) receive a sense signal from a capacitive fluid sensor;
(ii) receive an alternating drive/reference signal;
(iii) determine a measured value indicative of a conductivity quantity of the at least one reference fluid based on the sense signal and the drive/reference signal;
(iv) determine a measured value indicative of a capacitance quantity of the at least one reference fluid based on the sense signal and the drive signal;
repeat (i)-(iv) over a range of temperatures;
store data indicative of a relationship between the measured values indicative of the capacitance quantity and the measured values indicative of conductivity quantity for the at least one reference fluid over a range of temperatures.

7. The apparatus according to claim 1 wherein the at least one reference fluid is at least one of: a plurality of beverages with differing alcohol content; a plurality of beverages having different ingredients or compositions.

8. An apparatus for monitoring a fluid under test, the apparatus comprising:
a processing apparatus comprising a processor and a memory configured to store data indicative of at least one reference fluid, wherein the stored data for the at least one reference fluid comprises data indicative of a capacitance quantity and a conductivity quantity over a range of temperatures, the processing apparatus configured to:
receive a sense signal from a capacitive fluid sensor;
receive an alternating drive/reference signal;
determine a measured value indicative of a conductivity quantity of the fluid under test based on the sense signal and the drive/reference signal;
determine a measured value indicative of a capacitance quantity of the fluid under test based on the sense signal and the drive/reference signal;
determine a measured temperature of the fluid under test;
determine whether the fluid under test is similar to the at least one reference fluid based on:
(i) the measured value indicative of the conductivity quantity, the measured value indicative of the capacitance quantity; and
(ii) the stored data indicative of the conductivity quantity for the at least one reference fluid at the measured temperature and the stored data indicative of the capacitance quantity for the at least one reference fluid at the measured temperature,
wherein the processing apparatus is configured to, for the at least one reference fluid:
determine an expected value of the conductivity quantity for the at least one reference fluid at the measured temperature from the stored data;
determine an expected value of the capacitance quantity for the at least one reference fluid at the measured temperature from the stored data;
determine whether the fluid under test is similar to the at least one reference fluid based on:
(iii) the measured value indicative of the conductivity quantity and the measured value of the capacitance quantity; and
(iv) the expected value indicative of the conductivity quantity and the expected value indicative of the capacitance quantity for the at least one reference fluid at the measured temperature, and
wherein the stored data comprises a mathematical function which approximates the expected value indicative of the conductivity quantity as a function of temperature and the processing apparatus is configured to determine an expected value indicative of the conductivity quantity for the at least one reference fluid at the measured temperature by using the measured value of the temperature in the mathematical function.

9. An apparatus for monitoring a fluid under test, the apparatus comprising:
a processing apparatus comprising a processor and a memory configured to store data indicative of at least one reference fluid, wherein the stored data for the at least one reference fluid comprises data indicative of a capacitance quantity and a conductivity quantity over a range of temperatures, the processing apparatus configured to:
receive a sense signal from a capacitive fluid sensor;
receive an alternating drive/reference signal;
determine a measured value indicative of a conductivity quantity of the fluid under test based on the sense signal and the drive/reference signal;
determine a measured value indicative of a capacitance quantity of the fluid under test based on the sense signal and the drive/reference signal;
determine a measured temperature of the fluid under test;
determine whether the fluid under test is similar to the at least one reference fluid based on:
(i) the measured value indicative of the conductivity quantity, the measured value indicative of the capacitance quantity; and
(ii) the stored data indicative of the conductivity quantity for the at least one reference fluid at the measured temperature and the stored data indicative of the capacitance quantity for the at least one reference fluid at the measured temperature,
wherein the processing apparatus is configured to, for the at least one reference fluid:
determine an expected value of the conductivity quantity for the at least one reference fluid at the measured temperature from the stored data;
determine an expected value of the capacitance quantity for the at least one reference fluid at the measured temperature from the stored data;
determine whether the fluid under test is similar to the at least one reference fluid based on:
(iii) the measured value indicative of the conductivity quantity and the measured value of the capacitance quantity; and
(iv) the expected value indicative of the conductivity quantity and the expected value indicative of the capacitance quantity for the at least one reference fluid at the measured temperature, and
wherein the stored data comprises a mathematical function which approximates the expected value indicative of the capacitance quantity as a function of temperature and the processing apparatus is configured to determine an expected value indicative of the capacitance quantity for the at least one reference fluid at the measured temperature by using the measured value of the temperature in the mathematical function.

10. An apparatus for measuring at least one property of a fluid under test, the apparatus comprising:
a processing apparatus comprising a processor and a memory configured to store data indicative of a relationship between an expected value indicative of a capacitance quantity and an expected value indicative of a conductivity quantity for a reference fluid over a range of temperatures, the processing apparatus configured to:
receive a sense signal from a capacitive fluid sensor;
receive an alternating drive/reference signal;
determine a measured value indicative of a conductivity quantity of the fluid under test based on the sense signal and the drive/reference signal;
determine a measured value indicative of a capacitance quantity of the fluid under test based on the sense signal and the drive/reference signal; and
determine an expected value indicative of the capacitance or conductivity quantity of the fluid under test by using the measured value indicative of the conductivity or capacitance quantity, respectively, and the stored data; and determine a difference between the expected and measured values indicative of the capacitance or conductivity quantity respectively.

11. The apparatus according to claim 10, wherein the data indicative of a relationship between an expected value indicative of a capacitance quantity and an expected value indicative of a conductivity quantity comprises a mathematical function which approximates the expected value indicative of the capacitance quantity as a function of the conductivity quantity and wherein the processing apparatus is configured to determine an expected value of the capacitance quantity of the fluid under test by using the actual value indicative of the conductivity quantity in the mathematical function.

12. The apparatus according to claim 10, wherein the data indicative of a relationship between the expected value indicative of the capacitance quantity and the expected value indicative of the conductivity quantity for the reference fluid over the range of temperatures comprises a set of data values relating the expected value indicative of the capacitance quantity to the expected value indicative of the conductivity quantity at different temperatures and the processing apparatus is configured to determine an expected value indicative of the capacitance quantity of the fluid under test by performing a look up operation in, or by interpolating between, the set of data values using the actual value indicative of the conductivity quantity.

13. The apparatus according to claim 10, wherein the data indicative of a relationship between an expected value indicative of a capacitance quantity and an expected value indicative of a conductivity quantity comprises a mathematical function which approximates the expected value indicative of the conductivity quantity as a function of the capacitance quantity and wherein the processing apparatus is configured to determine an expected value of the conductivity quantity of the fluid under test by using the actual value indicative of the capacitance quantity in the mathematical function.

14. The apparatus according to claim 10, wherein the data indicative of a relationship between the expected value indicative of the capacitance quantity and the expected value indicative of the conductivity quantity for the reference fluid over the range of temperatures comprises a set of data values relating the expected value indicative of the conductivity quantity to the expected value indicative of the capacitance quantity at different temperatures and the processing apparatus is configured to determine an expected value indicative of the conductivity quantity of the fluid under test by performing a look up operation in, or by interpolating between, the set of data values using the actual value indicative of the capacitance quantity.

15. The apparatus according to claim 10 wherein the processing apparatus is configured to determine a complex impedance of the fluid sensor based on the sense signal and the drive/reference signal, the complex impedance comprising a real (in-phase) component indicative of the conductivity quantity of the fluid under test and an imaginary (quadrature) component indicative of the capacitance quantity of the fluid under test.

16. The apparatus according to claim 10 wherein the processing apparatus is configured to compare the difference with a threshold difference value and to perform an action when the difference exceeds the threshold difference value.

17. The apparatus according to claim 16 wherein the action comprises at least one of: sending a notification; issuing an alarm.

18. The apparatus according to claim 10 further comprising a capacitive fluid sensor having a first electrode and a second electrode with a sensing region between the electrodes.

* * * * *